(12) United States Patent
Govardhan et al.

(10) Patent No.: US 9,376,479 B2
(45) Date of Patent: Jun. 28, 2016

(54) HUMAN GROWTH HORMONE CRYSTALS AND METHODS FOR PREPARING THEM

(75) Inventors: Chandrika Govardhan, Lexington, MA (US); Nazer Khalaf, Worcester, MA (US); Benjamin Paul Simeone, Lexington, MA (US)

(73) Assignee: Anjinomoto Althea, Inc., San Diego, CA (US)

(*) Notice: Subject to any disclaimer, the term of this patent is extended or adjusted under 35 U.S.C. 154(b) by 288 days.

(21) Appl. No.: 10/749,962

(22) Filed: Dec. 31, 2003

(65) Prior Publication Data

US 2004/0209804 A1 Oct. 21, 2004

Related U.S. Application Data

(60) Provisional application No. 60/437,519, filed on Dec. 31, 2002, provisional application No. 60/517,042, filed on Nov. 3, 2003.

(51) Int. Cl.
*C07K 14/61* (2006.01)
*A61K 9/00* (2006.01)
*A61K 38/00* (2006.01)

(52) U.S. Cl.
CPC .............. *C07K 14/61* (2013.01); *A61K 9/0019* (2013.01); *A61K 38/00* (2013.01); *C07K 2299/00* (2013.01)

(58) Field of Classification Search
None
See application file for complete search history.

(56) References Cited

U.S. PATENT DOCUMENTS

| | | |
|---|---|---|
| 2,538,018 A | 1/1951 | Krayenbuhl et al. |
| 4,342,832 A | 8/1982 | Goeddel et al. |
| 4,816,568 A | 3/1989 | Hamilton, Jr. et al. |
| 4,853,218 A | 8/1989 | Yim et al. |
| 4,917,685 A | 4/1990 | Viswanathan et al. |
| 5,070,186 A | 12/1991 | Joergensen |
| 5,084,350 A | 1/1992 | Chang et al. |
| 5,096,885 A | 3/1992 | Pearlman et al. |
| 5,346,903 A | 9/1994 | Ackerman et al. |
| 5,439,643 A | 8/1995 | Liebert |
| 5,547,930 A | 8/1996 | Balschmidt |
| 5,589,167 A | 12/1996 | Cleland et al. |
| 5,633,352 A | 5/1997 | Dalbøge et al. |
| 5,654,010 A | 8/1997 | Johnson et al. |

(Continued)

FOREIGN PATENT DOCUMENTS

| | | |
|---|---|---|
| AU | 686567 | 2/1998 |
| CA | 2086087 | 9/1999 |

(Continued)

OTHER PUBLICATIONS

Weber, Overview of Crystallization Methods. Methods in Enzymology, 1997, vol. 276, pp. 13-22.*

(Continued)

*Primary Examiner* — Alexander Kim
(74) *Attorney, Agent, or Firm* — John Storella; Shirley Recipon

(57) ABSTRACT

The present invention relates to stable, extended release crystals of human growth hormone or a human growth hormone derivative and compositions or formulations comprising such crystals. The invention further provides methods for producing those crystals and compositions. The invention further provides methods for treatment of an individual having disorders associated with human growth hormone deficiency or which are ameliorated by treatment with human growth hormone using those crystals and compositions or formulations.

23 Claims, 21 Drawing Sheets

(56) References Cited

U.S. PATENT DOCUMENTS

| | | | |
|---|---|---|---|
| 5,667,808 | A | 9/1997 | Johnson et al. |
| 5,691,169 | A | 11/1997 | Dalbøge et al. |
| 5,700,459 | A | 12/1997 | Krone et al. |
| 5,705,482 | A | 1/1998 | Christensen et al. |
| 5,734,026 | A | 3/1998 | Florin-Robertsson et al. |
| 5,780,599 | A | 7/1998 | Junker et al. |
| 5,788,959 | A * | 8/1998 | Singh .......................... 424/85.1 |
| 5,840,680 | A | 11/1998 | Balschmidt |
| 5,849,535 | A * | 12/1998 | Cunningham et al. ....... 435/69.4 |
| 5,849,700 | A * | 12/1998 | Sørensen et al. ................ 514/12 |
| 5,849,704 | A | 12/1998 | Sørensen et al. |
| 5,885,960 | A | 3/1999 | Nies |
| 5,932,212 | A | 8/1999 | Khalaf |
| 5,972,331 | A | 10/1999 | Reichert et al. |
| 5,981,485 | A | 11/1999 | O'Connor et al. |
| 6,004,549 | A | 12/1999 | Reichert et al. |
| 6,022,858 | A | 2/2000 | Sørensen et al. |
| 6,066,470 | A | 5/2000 | Nishimura et al. |
| 6,117,984 | A | 9/2000 | Junker et al. |
| 6,180,608 | B1 | 1/2001 | Gefter et al. |
| 6,267,981 | B1 | 7/2001 | Okamoto et al. |
| 6,309,859 | B1 | 10/2001 | Nishimura et al. |
| 6,359,118 | B2 | 3/2002 | Margolin et al. |
| 6,376,461 | B1 | 4/2002 | Igari et al. |
| 6,417,237 | B1 | 7/2002 | Dadey et al. |
| 6,448,225 | B2 | 9/2002 | O'Connor et al. |
| 6,541,606 | B2 | 4/2003 | Margolin et al. |
| 6,828,303 | B2 | 12/2004 | Kim et al. |
| 7,351,798 | B2 | 4/2008 | Margolin et al. |
| 2001/0007858 | A1 | 7/2001 | O'Connor et al. |
| 2002/0009491 | A1 | 1/2002 | Rothbard et al. |
| 2002/0086829 | A1 | 7/2002 | Gefter |
| 2002/0142050 | A1 | 10/2002 | Straub et al. |
| 2002/0197328 | A1 | 12/2002 | Kim et al. |
| 2003/0013653 | A1 | 1/2003 | O'Connor et al. |
| 2003/0099663 | A1 | 5/2003 | Fleitmann et al. |
| 2003/0175239 | A1 | 9/2003 | Margolin et al. |
| 2004/0029777 | A1 | 2/2004 | Ando et al. |
| 2004/0209804 | A1 | 10/2004 | Govardhan |
| 2006/0008532 | A1 * | 1/2006 | Govardhan et al. ........... 424/489 |

FOREIGN PATENT DOCUMENTS

| | | |
|---|---|---|
| CA | 2330476 | 11/1999 |
| CA | 2147482 | 9/2003 |
| EP | 0216485 A1 | 4/1987 |
| EP | 0 303 746 A1 | 2/1989 |
| EP | 0 540 582 B1 | 8/1994 |
| EP | 0926159 A2 | 6/1999 |
| EP | 0 652 766 B1 | 11/2000 |
| EP | 0 779 806 B1 | 11/2000 |
| EP | 1073421 A1 | 2/2001 |
| EP | 1083232 A1 | 3/2001 |
| EP | 1114644 B1 | 7/2001 |
| EP | 1342477 A1 | 9/2003 |
| GB | 643268 | 9/1950 |
| JP | H5-507497 | 10/1993 |
| JP | 2002-512949 | 5/2002 |
| JP | 4686361 | 2/2011 |
| WO | 9118927 A1 | 12/1991 |
| WO | WO 92/00998 | 1/1992 |
| WO | 9211844 A1 | 7/1992 |
| WO | WO 9312812 A | 7/1993 |
| WO | 9325222 A1 | 12/1993 |
| WO | WO 94/03198 | 2/1994 |
| WO | WO 9403198 | 2/1994 |
| WO | WO 9410192 A1 | 5/1994 |
| WO | WO 95/28174 | 10/1995 |
| WO | WO 96/07397 A2 | 3/1996 |
| WO | WO 96/07399 A1 | 3/1996 |
| WO | WO 96/21459 | 7/1996 |
| WO | WO 96/21460 | 7/1996 |
| WO | WO 97/01331 | 1/1997 |
| WO | 9705166 A1 | 2/1997 |
| WO | 9831346 A1 | 7/1998 |
| WO | 9835991 A1 | 8/1998 |
| WO | 99/12959 | 3/1999 |
| WO | 9930731 A1 | 6/1999 |
| WO | WO 9931137 | 6/1999 |
| WO | 9932116 A1 | 7/1999 |
| WO | WO 99/55310 | 11/1999 |
| WO | 0077281 A1 | 12/2000 |
| WO | 0101964 A2 | 1/2001 |
| WO | WO 01/24822 A2 | 4/2001 |
| WO | 0247716 A2 | 6/2002 |
| WO | 02055310 A1 | 7/2002 |
| WO | WO 02/053174 A2 | 7/2002 |
| WO | 02072636 | 9/2002 |
| WO | 03035099 A1 | 5/2003 |
| WO | 03042344 A2 | 5/2003 |
| WO | 2004006092 A2 | 1/2004 |
| WO | 2004060310 A2 | 7/2004 |
| WO | WO 2004060920 | 7/2004 |

OTHER PUBLICATIONS

Drenth, "Principles of Protein X-Ray Crystallography", 2nd Edition, 1999 Springer-Verlag New York Inc., Chapter 1, pp. 1-22.*

DeFelippis et al., 1998, J. Pharm. Sci., vol. 87, pp. 170-176.*

Compute pl Mw of hGH (last viewed on Aug. 17, 2010).*

Branden et al., Introduction to Protein Structure Second Edition, Garland Publishing Inc., New York, 1999, pp. 375, 374 and 382.*

Drenth et al., Principles of X-ray Crystallography, Springer, New York, 1999, pp. 1-21.*

Kierzek et al., Models of protein crystal growth., Biophys Chem, 91:1-20, 2001.*

Wiencek, New Strategies for Protein Crystal Growth., Ann Rev Biomed Eng, vol. 1:505-534, 1999.*

Buts et al., Impact of natural variation in bacterial F17G adhesins on crystallization behaviour., Acta Cryst D61:1149-1159, 2005.*

Skarzynski et al., Industrial persepctive on X-ray data collection and analysis., Acta Cryst D62:102-107, 2006.*

Kundrot et al., Which strategy for a protein crystallization project?., Models of protein crystal growth., Cell. Mol. Life Sci. 2004, 61: 525-536.*

Weber, Methods in Enzymology, 1997, vol. 276, pp. 13-22.*

Cudney, Protein Crystallization and Dumb Luck., Rigaku Journal, 1999, vol. 16, No. 1, pp. 1-7.*

McPherson, Current approaches to macromolecular crystallization., Eur. J. Biochem. 189:1-23, 1990.*

Human growth hormone (last viewed on Jan. 16, 2013).*

Bennani-Baiti et al., "Physical Linkage of the Human Growth Hormone Gene Cluster and the Skeletal Muscle Sodium Channel α-Subunit Gene (SCN4A) on Chromosome 17," *Genomics*, 29, 647-652, 1995.

Chantalat et al., "The Crystal Structure of Wild-Type Growth Hormone at 2.5 Å Resolution," *Protein and Peptide Letters*, vol. 2, 333-340, 1995.

Clark et al., "Long-acting Growth Hormones Produced by Conjugation with Polyethylene Glycol." *The Journal of Biological Chemistry*, vol. 271, No. 36, 21969-21977, 1996.

Clarkson et al., "Crystallization and X-ray Data Collection on Human Growth Hormone." *Journal of Molecular Biology*, vol. 208, 719-721, 1989.

Genentech, "Product Information—Nutropin Depot Full Prescribing Information," http://www.gene.com/gene/products/information/opportunistic/nutropin-depot/insert.jsp, 1999.

Haro et al., "Divalent Metal Cation Chelators Enhance Chromatographic Separation of Structurally Similar Macromolecules: Separation of Human Growth Hormone Isoforms," *Journal of Chromatography B*, vol. 720, 39-47, 1998.

Herberger et al., "Characterization of Prolease® Human Growth Hormone PLGA Microspheres Produced Using Different Solvents," *Proc. Intl. Symp. Controlled Release of Bioactive Materials*, vol. 23, 835-836, 1996.

Human Genome Sciences, "Albutropin," http://www.hgsi.com/products/albutropin.html, 2002.

(56) References Cited

OTHER PUBLICATIONS

Jones et al., "Crystallization of Authentic Recombinant Human Growth Hormone," *Biotechnology*, vol. 5, 499-500, 1987.
Katakam et al., "Controlled Release of Human Growth Hormone in Rats Following Parenteral Administration of Poloxamer Gels," *Journal of Controlled Release*, vol. 49(1), 21-26, 1997.
Kim et al., "Microencapsulation of Dissociable Human Growth Hormone Aggregates within Poly(D,L-lactic-co-glycolic acid)," *International Journal of Pharmaceutics*, vol. 229(1-2), 107-116, 2001.
Lewis et al., "Crystalline Human Growth Hormone," *The Journal of the American Chemical Society*, vol. 80, 4429-4430, 1958.
McPherson et al., "The Growth and Preliminary Investigation of Protein and Nucleic Acid Crystals for X-Ray Diffraction Analysis," *Methods of Biochemical Analysis*, vol. 23, 249-345, 1976.
Webster'S New World Dictionary of Science, Lindley and Moore, Eds., Macmillan, New York, New York, 673, 1998.
Wilhelmi et al., "A New Preparation of Crystalline Anterior Pituitary Growth Hormone," *Journal of Biological Chemistry*, 176, 735-745, 1948.
Wu et al., "Application of High-Performance Hydrophobic-Interaction Chromatography to the Characterization of Recombinant DNA-Derived Human Growth Hormone," *Journal of Chromatography*, 500, 595-606, 1990.
Branden et al., "Introduction to Protein Structure Second Edition", Garland Publishing Inc., New York, 1999, pp. 374-375.
Kierzek et al., "Models of Protein Crystal Growth", Biophysical Chemistry 1991 (2001) pp. 1-20.
Wiencek "New Strategies for Protein Crystal Growth", Annu. Rev. Biomed. Eng. 1999, 1:505-534.
Buts et al. "Impact of Natural Variation in Bacterial F17G Adhesins on Crystallization Behaviour", Acta Cryst. (2005) D61, pp. 1149-1159.
Skarzynski et al. "Industrial Perspective on X-ray Data Collection and Analysis", Acta Cryst. (2006) D62, pp. 102-107.
Kundrot et al. "Which Strategy for a Protein Crystallization Project", Cellular and Molecular Life Sciences, 61 2004, pp. 525-536.
Cudney "Protein Crystallization and Dumb Luck", Rigaku Journal, 1999, vol. 16, No. 1, pp. 1-7.
McPherson et al. "Current Approaches to Macromolecular Crystallization", Eur. J. Biochem. 189, 1-23 (1990).
Colloc'h et al., "Crystal Structure of the Protein Drug Urate Oxidase-Inhibitor complex at 2.05 A Resolution", Nature Structural Biology, vol. 4, No. 11, 1997, pp. 947-952.
Legoux et al., "Cloning and Expression in *Escherichia coli* of the Gene Encoding Aspergillus Flavus Urate Oxidase", Journal of Biological Chemistry, vol. 267, No. 12, Issue of Apr. 25, pp. 8565-8570, 1992.
GenBank Accession No. M73993, 1991.
Holmes et al., "Agricultural Use of Burkholderia (Pseudomonas) cepacia: A threat to Health?", Emerging Infectious Diseases, vol. 4, No. 2, Apr.-Jun. 1998, pp. 221-227.
Reily et al., "Therapeutic Properties of a New Glutaminase-Asparaginase Preparation and the Influence of Lactate Dehydrogenase-elevating Virus" Cancer Research vol. 34, pp. 429-438, Feb. 1974.
Brader et al., "Hypride Insulin Cocrystals for Controlled Release Delivery", Nature Biotechnology, vol. 20, No. 8, pp. 800-804, Aug. 2002.
Jen et al., "Diamonds in the Rough: Protein Crystals from a Formulation Perspective", Pharmaceutical Research, vol. 18, No. 11 pp. 1483-1488, Nov. 2001.
Maa Y-F et al., "Spray-Drying of Air-Liquid Interface Sensitive Recombinant Human Growth Hormone", Journal of Pharmaceutical Science, vol. 87, No. 2, pp. 152-159, Feb. 1998.
Cleland J L et al., "Stable Formulations of Recombinant Human Growth Hormone and Interferon-Gamma for Microencapsulation in Biodegradable Microspheres", Pharmaceutical Research, vol. 13, No. 10 pp. 1464-1475, Jan. 1996.
Govardhan Chandrika et al., Novel Long-Acting Crystal Formulation of Human Growth Hormone, Pharmaceutical Research, vol. 22, No. 9, pp. 1461-1470, Sep. 2005.
Supplementary European Search Report from corresponding EP Application No. 03808602.1 dated Feb. 3, 2009.
Caruso et al., "Enzyme encapsulation in layer-by-layer engineered polymer multilayer capsules," Langmuir, 16:1485-1488 (2000).
Dainiak et al., "Conjugates of monoclonal antibodies with polyelectrolyte complexes—an attempt to make an artificial chaperone," Biochimica et Biophysica Acta, 1381:279-285 (1998).
Ferreiro et al., "Stability of polycationic complexes of an antisense oligonucleotide in rat small intestine homogenates," European Journal of Pharmaceutics and Biopharmaceutics, 55:19-26 (2003).
Krayenbuhl et al., "Crystalline Protamine Insulin," Rep. Sten. Mem. Hosp. Nord. Insulin Lab., 1:60-73 (1946).
Kumar et al., "Spatially controlled cell engineering on biomaterials using polyelectrolytes," Langmuir, 19:10550-10556 (2003).
McPherson et al., "The growth and preliminary investigation of protein and nucleic acid crystals for x-ray diffraction analysis," Methods of Biochemical Analysis, 23:249-345 (1976).
Pridal et al., "Absorption of glucagon-like peptide-1 can be protracted by zinc or protamine," International Journal of Pharmaceutics, 136:53-59 (1996).
Vries et al., "Theory of polyelectrolyte adsorption on heterogeneously charged surfaces applied to soluble protein—polyelectrolyte complexes," Journal of Chemical Physics, 118(10):4649-4659 (2003).
Yu et al., "Thin films of polyelectrolyte-encapsulated catalase microcrystals for biosensing," Analytical Chemistry, 75(13):3031-3037 (2003).
Basu, et al., (2004). "Protein Crystals for the Delivery of Biopharmaceuticals," Expert Opin. Biol. Ther., v. 4, n. 3, pp. 301-317.
Colombia Application CO 05073929 Office Action Sep. 9, 2010.
Cudney, "Protein Crystallization and Dumb Luck," Rigaku Journal, 1999, v. 16, n. 1, pp. 1-7.
European Application EP03808602.1 Office Action mailed Dec. 18, 2009.
European Application EP03808602.1 Office Action mailed May 29, 2009.
European Application EP06846055.9 Supplemental European Search Report mailed Nov. 26, 2009.
European Application EP07869230 Office Action Dec. 11, 2009.
European Application EP03800385.1 SESR Oct. 27, 2006.
European Application EP03800385.1 Office Action May 4, 2010.
European Application EP03800385.1 Office Action Jan. 19, 2011.
Korean Patent Application 10-2005-7012348 Office Action dated Dec. 23, 2010.
Mexico Application MX2005007181 Office Action Nov. 18, 2010.
Mexico Application MX2005007182 Office Action Nov. 19, 2010.
PCT Application PCT/US06/49278 International Search Report mailed Sep. 25, 2007.
PCT Application PCT/US06/49278 International Preliminary Report on Patentability and Written Opinion.
PCT Application PCT/US07/087417 International Search Report mailed Feb. 5, 2009.
PCT Application PCT/US07/087417 International Preliminary Report on Patentability and Written Opinion.
PCT Application PCT/US03/041545 International Search Report mailed Apr. 13, 2005.
PCT Application PCT/US03/041545 International Preliminary Examination Report mailed Apr. 13, 2005.
PCT Application PCT/US2003/41691 International Search Report mailed May 17, 2004.
Singapore Application 200716575-6 Written Opinon Nov. 16, 2010.
U.S. Appl. No. 12/519,720 Non-Final Rejection mailed Oct. 22, 2010.
U.S. Appl. No. 12/519,720 Final Rejection mailed Feb. 8, 2011.
U.S. Appl. No. 11/169,956 Non-Final Rejection mailed Oct. 17, 2008.
U.S. Appl. No. 11/169,956 Final Rejection mailed Aug. 19, 2009.
Bramswig, J.H. "Long-term results of growth hormone therapy in Turner syndrome," Endocrine. Jun. 2001;15(1):5-13.

(56) References Cited

OTHER PUBLICATIONS

CA 2512052 Exam Report dated Nov. 14, 2011.
Carroll, et al. "Growthn hormone replacement in adults with growth hormone deficiency: assessment of current knowledge," Trends Endocrinol Metab. Aug. 2000;11(6):231-8.
Clark, et al., "Long-acting Growth Hormones Produced by Conjugation with Polyethylene Glycol," J. Biol. Chem., 271(36), 21696-21977 (1996).
CN200910140060.2 Office Action dated Oct. 16, 2012 (with English translation).
Eiholzer, et al. "Treatment with human growth hormone in patients with Prader-Labhart-Willi syndrome reduces body fat and increases muscle mass and physical performance," Eur J Pediatr. May 1998;157(5):368-77.
EP 11168985.7 European Search Report dated Apr. 27, 2012.
EP03808602 Search Report dated Jan. 23, 2009.
EP11168985.7 Office Action dated Apr. 16, 2013.
Fine, et al. "The impact of recombinant human growth hormone treatment during chronic renal insufficiency on renal transplant recipients," J Pediatr. Mar. 2000;136(3):376-82.
Frindik, et al. "Effects of recombinant human growth hormone on height and skeletal maturation in growth hormone-deficient children with and without severe pretreatment bone age delay," Horm Res. 1999;51(1):15-9.
Hirschfeld, "Use of human recombinant growth hormone and human recombinant insulin-like growth factor-I in patients with human immunodeficiency virus infection," Horm Res, 1996;46(4-5):215-21.
Leger, et al. "Human growth hormone treatment of short-stature children born small for gestational age: effect on muscle and adipose tissue mass during a 3-year treatment period and after 1 year's withdrawal," J Clin Endocrinol Metab. Oct. 1998;83(10):3512-6.
Mauras, et al. "High dose recombinant human growth hormone (GH) treatment of GH-deficient patients in puberty increases near-final height: a randomized, multicenter trial," Genentech, Inc., Cooperative Study Group. J Clin Endocrinol Metab. Oct. 2000;85(10):3653-60.
Mehls, et al. "Effects of recombinant human growth hormone in catabolic adults with chronic renal failure," Growth Horm IGF Res. Apr. 2000;10 Suppl B:S31-7.
Motoyama, et al. "Efficacy of Recombinant Human Growth Hormone in Pediatric Renal Transplantation Patients after Withdrawal of Steroid Therapy: Report of Two Cases," Clin. Exp. Nephrology, 2 (2), 1620165 (1998).
Mulligan, et al. "Use of growth hormone and other anabolic agents in AIDS wasting," JPEN J Farenter Enteral Nutr. Nov.-Dec. 1999;23(6 Suppl):S202-9.
Pasquino, et al. "Final Height in Turner Syndrome Patients Treated with Growth Hormone," Horm Res. 1996;4-6(6):269-72.
Ritzen, et al. Hormone Research, 56 (506), 208 (2002).
Simpson., et al. "Growth hormone replacement therapy for adults: into the new millennium," Growth Horm. IGF Res. Feb. 2002;12(1):1-33.
Tat, et al, "Microencapsulation of recombinant cells: a new delivery system for gene therapy," FASEB J. Aug. 1993;7(11):1061-9.
Torres, et al. "Potential of recombinant human growth hormone in HIV-associated adipose redistribution syndrome," BioDrugs. Aug. 2000;14(2):83-91.
Tritos, et al. "Recombinant human growth hormone: old and novel uses," Am J Med. Jul. 1998;105(1):44-57.
Ueland, et al, "Effects of 12 months of GH treatment on cortical and trabecular bone content of IGFs and OPG in adults with acquired GH deficiency: a double-blind, randomized, placebo-controlled study," J Clin Endocrirtol Metab. Jun. 2002;87(6):2760-3.
CA 2512052 $2^{nd}$ Examiner's Report dated Nov. 14, 2012.
CA 2512052 Office Action dated Aug. 9, 2013.
CA 2512052 Office Action dated Oct. 28, 2014.
CN 200910140060.2 Office Action dated Jun. 5, 2013 (with English translation).
CN 200910140060.2 Office Action dated Oct. 16, 2012 (with English translation).
CN 200910140060.2 Office action dated Nov. 26, 2013 (with English translation).
CN 200910140060.2 Final Rejection dated Apr. 1, 2014 (with English translation).
EP 03808602.1 Office Action dated Jun. 11, 2012.
EP 03808602.1 Office Action dated Apr. 3, 2014.
EP 11168985.7 Extended Search Report dated Jul. 27, 2012.
EP 11168985.7 Office Action dated Oct. 8, 2014.
Katakam et al., Controlled Release of human growth hormone in rats following parental administration of poloxamer gels. Journal of Controlled Release, 49(1), 21-26 (1997).

\* cited by examiner

SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

HUMAN GROWTH HORMONE CRYSTALS AND METHODS FOR PREPARING THEM

CROSS-REFERENCE TO RELATED APPLICATIONS

This application claims benefit under 35 U.S.C. §119(e) of U.S. provisional patent application No. 60/437,519, filed Dec. 31, 2002, and 60/517,042, filed Nov. 3, 2003, the disclosures of which are herein incorporated by reference.

SEQUENCE LISTING

The instant application contains a Sequence Listing which has been submitted in a paper copy as well as in computer readable form. The content of the paper and CFR copies are the same. The instant application contains a Sequence Listing which has been submitted in ASCII format via EFS-Web and is hereby incorporated by reference in its entirety. Said ASCII copy, created on Jan. 16, 2015 is named 38392-704-201-Seqlist.txt and is 3 Kilobytes in size.

TECHNICAL FIELD OF THE INVENTION

The present invention relates to crystals of human growth hormone or a human growth hormone derivative and compositions or formulations comprising them. In addition, the invention provides methods for producing crystals of human growth hormone or a human growth hormone derivative. The crystals of the present invention are particularly useful in methods for treating a mammal having disorders associated with human growth hormone deficiency or which are ameliorated by treatment with human growth hormone.

BACKGROUND OF THE INVENTION

Somatotropin or growth hormone ("GH") is a mammalian protein comprising a class of tropic hormones synthesized and secreted in the brain by the major gland of the endocrine system, the adenohypophysis. The secretion of GH and other tropic hormones by the adenohypophysis regulates the activity of cells in other endocrine glands and tissues throughout the body. Specifically, GH is secreted by somatotrophs of the anterior pituitary gland and functions to stimulate the liver and other tissues to synthesize and secrete IGF-1, a protein that controls cell division, regulates metabolic processes and exists in a free state or binds to one of six other proteins designated as IGFBP-1 through 6. The secretion process itself is modulated by opposing actions of somatoliberin (promoting GH release) and somatostatin (inhibiting GH release).

Human growth hormone ("hGH") is of particular interest because it serves as a critical hormone in the regulation of cell and organ growth and in physiological function upon various stages of aging. For example, overproduction of hGH results in gigantism in children and acromegaly in adults, whereas under-production leads to dwarfism in children [Mauras et al., *J. Clin. Endocrinology and Metabolism*, 85(10), 3653-3660 (2000); Frindik et al., *Hormone Research*, 51(1), 15-19 (1999); Leger et al., *J. Clin. Endocrinology and Metabolism*, 83(10), 3512-3516 (1998)], Turner's Syndrome (females only) [Bramswig, *Endocrine*, 15(1), 5-13 (2001); Pasquino et al., *Hormone Research*, 46(6), 269-272 (1996)] and chronic renal insufficiency [Carroll et al., *Trends in Endocrinology and Metabolism*, 11(6), 231-238 (2000); Ueland et al., *J. Clin. Endocrinology and Metabolism*, 87(6), 2760-2763 (2002); Simpson et al., *Growth Hormone & IGF Research*, 12, 1-33 (2002)]. In adults, hGH deficiency can affect metabolic processing of proteins, carbohydrates, lipids, minerals and connective tissue and can result in muscle, bone or skin atrophy [Mehls and Haas, *Growth Hormone & IGF Research*, Supplement B, S31-S37 (2000); Fine et al., *J. Pediatrics*, 136(3), 376-382 (2000); Motoyama et al., *Clin. Exp. Nephrology*, 2(2), 162-165 (1998)]. Other hGH deficiency disorders characterized by growth failure include AIDS wasting syndrome [Hirschfeld, *Hormone Research*, 46, 215-221 (1996); Tritos et al., *Am. J. Medicine*, 105(1), 44-57 (1998); Mulligan et al., *J. Parenteral and Enteral Nutrition*, 23(6), S202-S209 (1999); Torres and Cadman, *BioDrugs*, 14(2), 83-91 (2000)] and Prader-Willi syndrome [Ritzen, *Hormone Research*, 56(5-6), 208 (2002); Eiholzer et al., *Eur. J. Pediatrics*, 157(5), 368-377 (1998)].

To date, treatment regimens for hGH deficiency in humans focus primarily on subcutaneous injection of purified hGH made by recombinant DNA technology. That therapeutic is packaged as either a solution in a cartridge or a lyophilized powder requiring reconstitution at the time of use. The frequency of injection varies depending on the disease being treated and the commercially available product being used. For example, dwarfism is treated by daily subcutaneous injection of recombinant hGH.

The use of subcutaneous administration as a rapid delivery route for hGH is necessitated by the inherent instability of the protein in solution. That instability results from cleavage of critical intramolecular crosslinks at specific positions within the amino acid sequence of the protein, which in turn disrupts the essential three-dimensional structure recognized by and associated with cellular surfaces in the patient. The mechanism for hGH cleavage or degradation is orchestrated primarily by oxidation of methionine residues or deamidation of aspartic acid residues upon dissolution, thereby rendering the protein inactive. Due to this fragility, a need in the art exists for hGH compositions or formulations that are stable and long-acting and can be delivered not only subcutaneously but by other conventional dosage routes, such as oral, dermal and intravenous routes.

A number of commercially available hGH products have been developed in an attempt to address this need. For example, NUTROPIN DEPOT® human growth hormone is an injectable suspension of recombinant human growth hormone (rhGH) embedded in a polylactide-coglycolide (PLG) microspheres (see www.gene.com). In addition to rhGH and PLG, the microspheres also comprise zinc acetate and zinc carbonate components. Prior to administration, the solid material must be reconstituted with an aqueous solution comprising carboxymethylcellulose sodium salt, polysorbate, sodium chloride and water. This suspension, which is mostly comprised of polymer, is administered once or twice monthly and requires a 21 gauge needle for injection. Due to the size of the microspheres and the viscous nature of the product, adverse injection-site reactions can occur, resulting in nodules, erythema, pain, bruising, itching, lipoatrophy and puffiness (see www.genentech.com/gene/products/information/opportunistic/nutropin-depot/index sp).

Another hGH product in development but subsequently discontinued is ALBUTROPIN™ human growth hormone, a long acting genetically produced fusion protein of human albumin and human growth hormone (see www.hgsi.com/products/albutropin.html). This product is said to exhibit prolonged half-life in circulation, roughly a fifty percent increase over that of soluble native hGH. ALBUTROPIN™ human growth hormone is typically delivered by injection on a weekly basis and is said to stimulate IGF-1 levels long after clearance from the body. The biological effect of this product is similar to that of currently available growth hormone therapies.

Another product developed was INFITROPIN CR™ human growth hormone, a formulation of hGH comprised of polyethylene glycol-conjugated hGH molecules. This conjugated hGH required a once a week injection and was said to be released at a continuous rate, without significant burst effect [Ross et al., *J. Biol. Chem.*, 271(36), 21696-21977 (1996)]. However, this product was discontinued.

U.S. Pat. Nos. 5,981,485 and 6,448,225 refer to aqueous formulations of hGH that are said not to require a reconstitution step and are administered by daily injection. Such formulations typically contain hGH, a buffer, a non-ionic surfactant and optionally, a neutral salt, mannitol, or a preservative.

Various other drug delivery technologies, such as hydrogels [Katakam et al., *J. Controlled Release*, 49(1), 21-26 (1997)], liposomes, oil emulsions and biodegradable polymer microspheres, have been used in attempts to provide sustained drug release of hGH. However, the resulting formulations display a burst release of the drug, use harsh conditions and some are complicated to manufacture. This is especially true of hGH formulations based on DL-lactic co-glycolic acid (PLGA) microsphere technology, because the process used to produce the microspheres tends to employ conditions such as elevated temperatures, surfactant, organic solvents and aqueous/organic solvent interface, all of which cause protein denaturation [Herberger et al., Proc. Intl. *Symp. Controlled Release of Bioactive Materials*, 23, 835-836 (1996); Kim et al., *Intl. J. Pharmaceutics*, 229(1-2), 107-116 (2001)].

Some of the above-described preparations require hGH to be stored in a lyophilized state, which can be a time consuming and expensive process. U.S. Pat. Nos. 5,780,599 and 6,117,984 refer to divalent cation crystals of hGH and methods of producing divalent cation crystals of hGH, without the need for a lyophilization step.

Despite the efforts to address drawbacks of conventional hGH products, including instability upon storage and injection, short in vivo half-life, burst effects, lack of oral bioavailability, and difficulty and frequency of administration, the need for improved hGH preparations remains. To address this need, the present invention advantageously provides crystals of human growth hormone that yield stable, long-acting hGH.

SUMMARY OF THE INVENTION

The present invention is directed to stable, long-acting, convenient and patient-friendly crystals of human growth hormone or a human growth hormone derivative. The invention further provides compositions of crystals of human growth hormone or a human growth hormone derivative, including pharmaceutically acceptable compositions thereof. The invention further provides methods for preparing such crystals, as well as compositions comprising them. The crystals and compositions of this invention are advantageously used in methods for treating an individual having a disorder associated with human growth hormone deficiency or which is ameliorated by treatment by treatment with human growth hormone.

Crystals of human growth hormone or a human growth hormone derivative, or compositions or formulations comprising them, have several advantages, including: the capability of once per week dosing, ready to use crystalline suspension form, safety, efficacy, purity, stability, resuspendability and syringeability over a short period of time. Other objects of the invention, including improvements of hGH crystals and compositions or formulations comprising them, as compared with conventional hGH preparations, will be appreciated by those skilled in the art, in view of the disclosure herein.

DETAILED DESCRIPTION OF THE INVENTION

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, column chromatography, optical microscopy, UV-VIS spectroscopy, pharmacokinetic analyses, recombinant DNA methods, peptide and protein chemistries, nucleic acid chemistry and molecular biology described herein are those well known and commonly used in the art.

The following terms, unless otherwise indicated, shall be understood to have the following meanings:

The term "growth hormone (GH)" refers generally to growth hormones secreted by the pituitary gland in mammals. Although not an exhaustive list, examples of mammals include human, apes, monkey, rat, pig, dog, rabbit, cat, cow, horse, mouse, rat and goat. According to a preferred embodiment of this invention, the mammal is a human.

Figure 1:
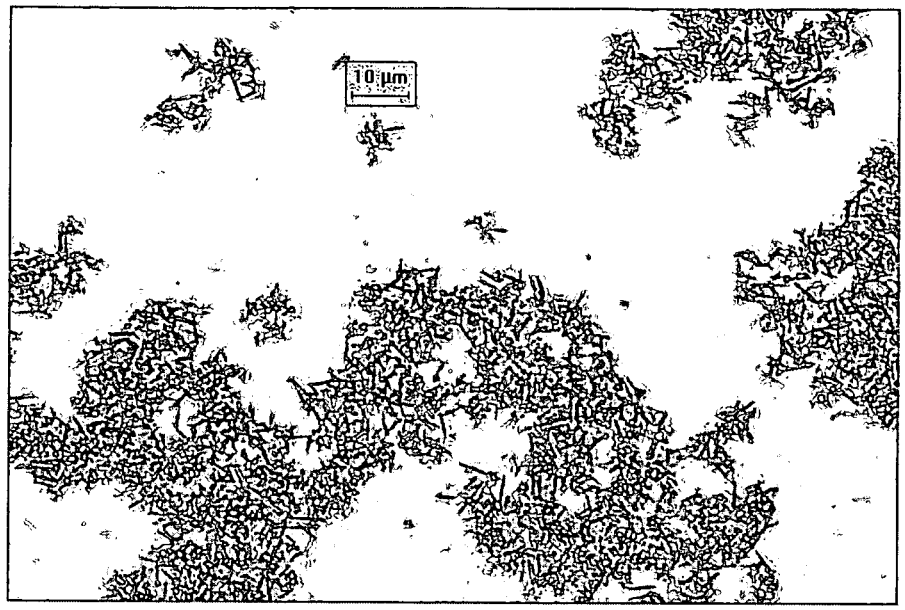
FIG. 1 illustrates hGH crystals grown in the presence of 860 mM ammonium phosphate (pH 8.9), as imaged by optical microscopy. See Example 1.
Figure 3:
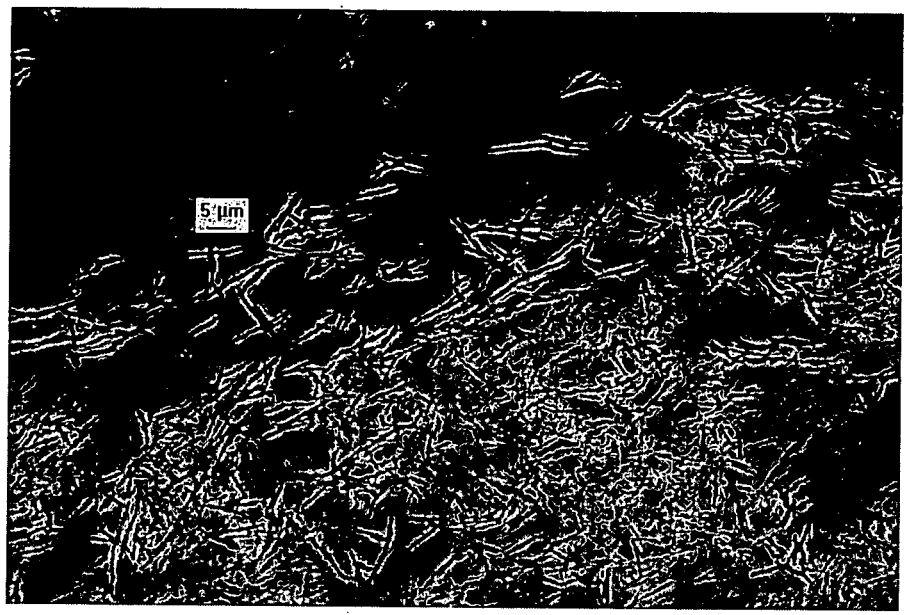
FIG. 3 illustrates hGH crystals grown in the presence of 600 mM dibasic sodium phosphate and 100 mM Tris-HCl (pH 8.6), as imaged by optical microscopy. See Example 3.

"Human growth hormone (hGH)" denotes a protein having an amino acid sequence, structure and function characteristic of native human growth hormone. As used herein, human growth hormone (hGH) also includes any isoform of native human growth hormone, including but not limited to, isoforms with molecular masses of 5, 17, 20, 22, 24, 36 and 45 kDa [Ham et al., J. Chromatography B, 720, 39-47 (1998)]. Thus, the term hGH includes the 191 amino acid sequence of native hGH, somatotropin, and the 192 amino acid sequence containing an N-terminal methionine (Met-hGH) and somatrem [U.S. Pat. Nos. 4,342,832 and 5,633,352]. As used herein, the 191 amino acid sequence of native hGH refers to the amino acid sequence shown in FIGS. 1 and 3 of U.S. Pat. No. 4,342,832, namely: "FPTIPLSRLF DNAMLRAHRL HQLAFDTYQE FEEAYIPKEQ KYSFLQNPQT SLCFS-ESIPT PSNREETQQK SNLELLRISL LLIQSWLEPV QFLRSVFANS LVYGASDSNV YDLLKDLEEG IQTLMGRLED GSPRTGQIFK QTYSKFDTNS HND-DALLKNY GLLYCFRKDM DKVETFLRIV QCRSVEG-SCG F." (SEQ ID NO:1) As used herein, hGH may be obtained by isolation and purification from a biological source or by recombinant DNA methods. If made by recombinant DNA methodology, hGH is denoted as recombinant human growth hormone (rhGH). Met-hGH is typically prepared by recombinant DNA methodology.

The term "human growth hormone derivative" refers to a protein having an amino acid sequence that is comparable to that of naturally occurring human growth hormone. The term "comparable" refers to an amino acid sequence that is between 2% and 100% homologous to the 191 amino acid sequence of hGH or the 192 amino acid-sequence of Met-hGH. In various embodiments of the present invention, human growth hormone derivatives comprise organic cations of hGH or Met-hGH, substitution, deletion and insertion variants of biologically synthesized hGH or Met-hGH proteins, post-translationally modified hGH and Met-hGH proteins, including deamidation, phosphorylation, glycoslylation, acetylation, aggregation and enzymatic cleavage reactions [Haro et al., J. Chromatography B, 720, 39-47 (1998)], chemically modified hGH or Met-hGH proteins derived from biological sources, polypeptide analogs and chemically synthesized peptides containing amino acid sequences analogous to those of hGH or Met-hGH.

Methods used to prepare hGH or Met-hGH include isolation from a biological source, recombinant DNA methodology, synthetic chemical routes or combinations thereof. To date, genes that encode for different DNA sequences of hGH include hGH-N and hGH-V [Haro et al., *J. Chromatography B,* 720, 39-47 (1998); Bennani-Baiti et al., *Genomics,* 29, 647-652 (1995)].

The term "valency" is defined as an element's ability to combine with other elements and which is dictated by the number of electrons in the outermost shell of the atom and expressed as the number of atoms of hydrogen (or any other standard univalent element) capable of uniting with (or replacing) its atoms [Webster's New World Dictionary of Science, Lindley, D. and Moore T. H., Eds., Macmillan, New York, N.Y., 1998]. The terms "monovalent cation" and "divalent cation" refer to ions carrying a positive charge that have either a valence state of one or two, respectively. Cations having different valence states can be organic or inorganic in nature. Examples of monovalent inorganic cations include ammonium ($NH_4^+$) and Group I elements of the periodic table ($H^+$, $Li^+$, $Na^+$, $K^+$, $Rb^+$, $Cs^+$, and $Fr^+$) and divalent inorganic cations include Group II elements ($Be^{2+}$, $Mg^{2+}$, $Ca^{2+}$, $Sr^{2+}$, $Ba^{2+}$, $Mn^{2+}$, $Co^{2+}$, $Ni^{2+}$, $Cu^{2+}$, $Zn^{2+}$, $Cd^{2+}$, $Mo^{2+}$ and $Ra^{2+}$).

"Calcium crystal of human growth hormone or a human growth hormone derivative" refers to human growth hormone, or a derivative thereof, that has been crystallized in the presence of a divalent calcium ion. The divalent calcium ion is introduced into the crystallization solution as a calcium salt. In a preferred embodiment, a calcium crystal of human growth hormone or a human growth hormone derivative comprises from about 1 to about 500 calcium molecules per monomer or monomer chain of human growth hormone or human growth hormone derivative. In a more preferred embodiment, a calcium crystal of human growth hormone or a human growth hormone derivative comprises from about 1 to 140 calcium molecules per monomer or monomer chain of human growth hormone or human growth hormone derivative.

The term "calcium salt" includes both inorganic and organic counterions or molecules that form an ionic bond with a calcium ion(s). Examples of different calcium salts include calcium acetate hydrate, calcium acetate monohydrate, calcium acetylacetonate hydrate, calcium L-ascorbate dihydrate, calcium bis(6,6,7,7,8,8,8-heptafluoro-2,2-dimethyl-3,5-octanedionate), calcium bis(2,2,6,6-tetramethyl-3,5-heptanedionate), calcium bromide, calcium carbonate, calcium chloride, calcium chloride dihydrate, calcium chloride hexahydrate, calcium chloride hydrate, calcium citrate tetrahydrate, calcium dihydrogenphosphate, calcium 2-ethylhexanoate, calcium fluoride, calcium gluconate, calcium hydroxide, calcium hypochlorite, calcium iodate, calcium iodide, calcium iodide hydrate, calcium Ionophore I, calcium molybdate, calcium nitrate, calcium oxalate, calcium oxalate hydrate, calcium oxide, calcium pantothenate, calcium propionate, calcium pyrophosphate and calcium sulfate. In a preferred embodiment of this invention, the calcium salt is selected from the group consisting of calcium acetate, calcium chloride, calcium sulfate, and calcium gluconate. In a more preferred embodiment, the calcium salt is calcium acetate.

"Organic cation crystal of human growth hormone or a human growth hormone derivative" refers to human growth hormone that has been crystallized in the presence of an organic cation. The term "organic cation" refers to a positively charged atom or group of atoms that contain carbon. Examples of organic cations include quaternary ammonium cations, tetraethylammonium (TEA), tributylmethylammonium (TBuMA), procainamide ethobromide (PAEB), azidoprocainamide methoiodide (APM), d-tubocurarine, metocurine vecuronium, rocuronium, 1-methyl-4-phenylpyridinium, choline and N-(4,4-axo-n-pentyl)-21-deoxyajmalinium (APDA).

hGH is commercially available in lyophilized form and is typically produced by recombinant DNA methods. According to this invention, crystallization of hGH is generally accomplished by preparing a buffered solution of hGH, purifying and/or desalting, dialyzing and concentrating the solution and adding a monovalent or divalent cation or salt to the solution. The latter step results in the formation of an organic or inorganic cation bound to hGH.

One preferred embodiment of this invention relates to monovalent cation crystals of hGH or an hGH derivative. In a more preferred embodiment, the monovalent cation is selected from the group consisting of: lithium, sodium, potassium and ammonium. In a most preferred embodiment, the monovalent cation is sodium. In a most preferred embodiment, human growth hormone or a human growth hormone derivative comprises from about 1 to about 500 monovalent cation molecules per monomer or monomer chain of human growth hormone or human growth hormone derivative.

The term "monovalent cation salt" includes both inorganic and organic counterions or molecules that from an ionic bond with the monovalent ion. In a preferred embodiment, the monovalent cation salt is a sodium salt. In a more preferred embodiment, the sodium salt is selected from the group consisting of sodium citrate, sodium phosphate and sodium acetate. In a most preferred embodiment, the sodium salt is sodium acetate.

Another preferred embodiment of this invention relates to a protamine crystal of hGH or an hGH derivative. Likewise, in yet another preferred embodiment, this invention relates to a polyarginine crystal of hGH or an hGH derivative.

A further preferred embodiment of this invention includes monovalent or divalent crystals of hGH or an hGH derivative complexed or co-crystallized with protamine or polyarginine. More preferably, the crystals are sodium crystals complexed or co-crystallized with protamine or polyarginine.

The soluble form of hGH may be characterized by a variety of methods, including reversed phase high performance liquid chromatography (RP-HPLC), size exclusion chromatography high performance liquid chromatography (SEC-HPLC) and hydrophobic interaction chromatography (HIC) [Wu et al., *J. Chromatography,* 500, 595-606 (1990); "*Hormone Drugs*", FDA publication, (1982)]. On the other hand, the crystalline form of hGH may be characterized by optical microscopy and X-ray diffraction. In general, the conditions of crystallization will determine the shape of a protein crystal, i.e., a shape selected from the group consisting of spheres, needles, rods, plates (hexagonals and squares), rhomboids, cubes, bipyramids and prisms.

Crystals of hGH or an hGH derivative according to this invention form rod-like or needle-like morphologies when imaged with optical microscopy. In one embodiment, crystals of hGH or an hGH derivative form rods or needles that are between about 0.1 and about 200 µm in length. In a preferred embodiment, crystals of hGH or an hGH derivative form rods or needles that are between about 3 and about 100 µm in length. In a more preferred embodiment, crystals of hGH or an hGH derivative form rods or needles that are between about 10 and about 25 µm in length.

Another embodiment of this invention relates to compositions comprising calcium, monovalent cation, protamine or polyarginine crystals of hGH or an hGH derivative and a pharmaceutically acceptable excipient. In yet another preferred embodiment, crystals of hGH or an hGH derivative and the excipient are present in such compositions in a molar ratio of hGH:excipient of about 1:250 to about 1:20. In an alternate preferred embodiment, the crystals of hGH or an hGH derivative and the excipient are present in a molar ratio of hGH:excipient of about 3:1 to about 1:10. In yet another preferred embodiment, the crystals of hGH or an hGH derivative and the excipient are present in a molar ratio of hGH:excipient of about 1:10 to about 1:0.125. In a preferred embodiment, crystals of hGH or hGH derivative are grown with sodium acetate that may be either crystallized with or coated with polyarginine or protamine.

Crystals of human growth hormone or a human growth hormone derivative can be combined with any pharmaceutically acceptable excipient. According to this invention, a "pharmaceutically acceptable excipient" is an excipient that acts as a filler or a combination of fillers used in pharmaceutical compositions. Preferred excipients included in this category are: 1) amino acids, such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. Salts of such compounds may also be used. A further preferred group of excipients includes sucrose, trehalose, lactose, sorbitol, lactitol, mannitol, inositol, salts of sodium and potassium, such as acetate, phosphates, citrates and borate, glycine, arginine, polyethylene oxide, polyvinyl alcohol, polyethylene glycol, hexylene glycol, methoxy polyethylene glycol, gelatin, hydroxypropyl-β-cyclodextrin, polylysine and polyarginine.

In one embodiment of this invention, the excipient is selected from the group consisting of: amino acids, salts, alcohols, carbohydrates, proteins, lipids, surfactants, polymers, polyamino acids and mixtures thereof. In a preferred embodiment, the excipient is selected from the group consisting of: protamine, polyvinylalcohol, cyclodextrins, dextrans, calcium gluconate, polyamino acids, such as polyarginine, polylysine and polyglutamate, polyethylene glycol, dendrimers, polyorthinine, polyethyleneimine, chitosan and mixtures thereof. In a more preferred embodiment, the excipient is selected from the group consisting of: protamine, polyarginine, polyethylene glycol and mixtures thereof.

Crystals of human growth hormone or a human growth hormone derivative according to this invention can also be combined with a carrier or excipient, a substance that, when added to a therapeutic, speeds or improves its action [The On-Line Medical Dictionary, cancerweb.ncl.ac.uk/omd/index.html]. Examples of carriers or excipients include, for example, buffer substances, such as phosphates, glycine, sorbic acid, potassium sorbate, partial glyceride mixtures of saturated vegetable fatty acids, waters, salts or electrolytes, such as Protamine sulfate, disodium hydrogen phosphate, sodium chloride, zinc slats, colloidal silica, magnesium, trisilicate, cellulose-based substances and polyethylene glycol. Carriers or excipients for gel base forms may include, for example, sodium carboxymethylcellulose, polyacrylates, polyoxyethylene-polyoxypropylene-block copolymers, polyethylene glycol and wood wax alcohols.

In yet a more preferred embodiment, the excipient is protamine. Furthermore, crystals of hGH or an hGH derivative and protamine are present in an hGH:protamine ratio of about 5:1 to about 1:10 (w/w). That ratio may also range between about 10:1 to about 20:1 (w/w). Most preferably, that ratio ranges between about 12:1 to about 15:1 (w/w). According to an alternate embodiment, that ratio is between about 3:1 and about 1:10 (w/w). In another embodiment, that ratio is between about 5:1 and about 40:1 (w/w). And, in a further embodiment, that ratio is about 5:1 (w/w).

In another aspect of the invention, the pharmaceutically acceptable excipient is selected from the group consisting of polyamino acids, including polylysine, polyarginine and polyglutamate. In a preferred embodiment of this invention, the excipient is polylysine. In a more preferred embodiment, polylysine has a molecular weight between about 1,500 and about 8,000 kD. In another embodiment, the crystals of hGH or an hGH derivative and polylysine are present in an hGH:polylysine ratio of about 5:1 to about 40:1 (w/w). That ratio may also range between about 10:1 to about 20:1 (w/w). Most preferably, that ratio ranges between about 12:1 to about 15:1 (w/w). According to an alternate embodiment, that ratio is about 5:1 to about 1:50 (w/w). And, in a further embodiment, that ratio is about 5:1 (w/w).

In yet another preferred embodiment of this invention, the excipient is polyarginine. In a more preferred embodiment, polyarginine has a molecular weight between about 15,000 and about 60,000 kD. In another embodiment, the crystals of hGH or an hGH derivative and polyarginine are present in an hGH:polyarginine ratio of about 5:1 to about 40:1 (w/w). That ratio may also range between about 10:1 to about 20:1 (w/w). Most preferably, that ratio ranges between about 12:1 to about 3:1 (w/w). According to an alternate embodiment, that ratio is about 5:1 to about 1:50 (w/w). In another embodiment, that ratio is between about 12:1 and about 15:1 (w/w). And, in a further embodiment, that ratio is about 5:1 (w/w).

One embodiment according to the present invention includes an injectable crystalline suspension comprising about 20 mg/ml of crystals of hGH or an hGH derivative. That suspension is characterized by easy resuspendability, slow sedimentation and a time action profile of about 7 days. It may be injected once weekly, using a 30 gauge syringe and providing an 80% level of effective loading. That suspension is pure, as reflected by parameters of 0.02% aggregation (SE-HPLC) and 2.3% related proteins (RP-HPLC). This purity is maintained for at least about 4 months under refrigerated conditions.

One embodiment of this invention relates to a crystal of hGH or an hGH derivative which is characterized as having delayed dissolution behavior when introduced into an individual, as compared to that of conventional soluble hGH or hGH formulations. According to this invention, dissolution of crystals of hGH or an hGH derivative is characterized by either in vitro or in vivo dissolution parameters. For example, in vitro dissolution is described as the concentration of soluble hGH (expressed as a percentage of total or mg of total hGH or hGH derivative crystals originally present) obtained per 15 minutes or per wash step in a sequential dissolution process (see Example 5). In one embodiment of this invention, crystals of hGH or an hGH derivative are characterized by an in vitro dissolution rate of between about 2 and about 16% of said crystal per wash step upon exposure to a dissolution buffer (50 mM HEPES (pH 7.2), 140 mM NaCl, 10 mM KCl and 0.02% (v/v) $NaN_3$) at a temperature of 37° C., wherein the concentration of hGH or an hGH derivative is present in solution at a concentration of about 2 mg/ml. In another embodiment, crystals of hGH or an hGH derivative are characterized by an in vitro dissolution rate of between about 0.04 to about 0.32 mg of said crystal per wash step in a sequential dissolution process (see Example 5). On the other hand, in vivo dissolution is described by serum levels of hGH in a mammal over time after a single injection of hGH into the mammal.

In mammals, GH stimulates tissues to synthesize and secrete IGF-1, a protein that, in turn, plays a role in cell division and metabolic processes. As will be appreciated by those of skill in the art, serum hGH and IGF-1 levels are dependent on many factors, including physiological and treatment-related factors. Such factors include, but are not limited to: physiological factors, such as: birth age and bone age, sex, body weight, developmental stage (e.g., increased level at puberty) and treatment-related factors, such as dose, rate (kinetics) of dosing and route of administration. Also, those of skill in the art will appreciate that different hGH and IGF-1 levels may be beneficial, both from the standpoint of safety and efficacy, for different patient populations.

Adults or children suffering from a variety of hGH insufficiencies, disease states or syndromes may be treated by various regimens of exogenously delivered hGH using hGH crystals or hGH derivative crystals according to this invention. For example, an endocrinologist may initiate therapy using a dose of about 0.2 mg/kg/week for a child, increasing the dose to about 0.3 mg/kg/week after several weeks or months of treatment, with the dose being further increased to about 0.7 mg/kg/week around puberty. As will be appreciated by those of skill in the art, the level of such exogenously delivered hGH dosed to adults or children requiring hGH delivery is also dependent upon the existing physiological level or concentrations of hGH.

Dosage regimens for hGH in adults or children are often expressed in terms of mg/kg or International Units (IU/kg). Such regimens are generally scheduled for either a day or a week, i.e., mg/kg/day or mg/kg/week. With such considerations in mind, according to one embodiment of this invention, a single administration of crystals of hGH or an hGH derivative, or a composition comprising such crystals, for example, a single weekly administration of about 9 mg per 30 kg child, provides an in vivo hGH serum concentration of greater than about 10 ng/ml on days 1 and 2 post-administration, greater than about 5 ng/ml on days 3 and 4 post-administration and about 0.3 ng/ml on day 5 to day 7 post-administration. Alternatively, a single administration of crystals of hGH or an hGH derivative, or a composition comprising such crystals, provides an in vivo hGH serum concentration of about 0.3 ng/ml to about 2,500 ng/ml hGH, preferably about 0.5 ng/ml to about 1,000 ng/ml hGH, most preferably about 1 ng/ml to about 100 ng/ml hGH for between about 0.5 hours and about 40 days post-administration in said mammal, preferably for between about 0.5 hours and any one of about 10 days, 7 days or 1 day post-administration. Similarly, a single administration of crystals of hGH or an hGH derivative, or a composition comprising such crystals, provides an in vivo serum concentration of above about 2 ng/ml hGH, preferably above about 5 ng/ml hGH, most preferably above about 10 ng/ml hGH for between about 0.5 hours to about 40 days post-administration in said mammal, preferably for any one of about 10, 7 or 1 days post-administration. In a more preferred embodiment of this invention, a single administration of crystals of hGH or an hGH derivative, or a composition comprising such crystals, provides an in vivo serum concentration of greater than about 0.3 ng/ml hGH for between about 0.5 hours and about 40 days in a mammal, preferably for any one period of any one of about 10, 7 or 1 days post-administration. According to one embodiment of this invention, a single weekly administration of crystals of hGH or an hGH derivative, or a composition comprising such crystals, provides an in vivo hGH serum concentration of greater than about 10 ng/ml hGH on days 1 and 2 post-administration, greater than about 5 ng/ml hGH on days 3 and 4 post-administration and above about 0.3 ng/ml hGH on day 5 to day 7 post-administration. And, in a further embodiment, a single administration of crystals of hGH or an hGH derivative, or a composition comprising such crystals, provides an in vivo serum concentration of greater than about 0.3 ng/ml hGH for between about 0.5 hours and about 10 days post-administration.

According to one embodiment of this invention, a single administration of crystals of hGH or an hGH derivative, or a composition comprising such crystals, provides an in vivo IGF-1 serum elevation over baseline IGF-1 level prior to said administration of greater than 50 ng/ml from about 10 hours to about 72 hours post-administration and between about 0.5 ng/ml to about 50 ng/ml from about 72 hours to about 15 days post-administration, preferably about 10 days post-administration. Alternatively, a single administration of crystals of hGH or an hGH derivative, or a composition comprising such crystals, provides an in vivo IGF-1 serum elevation of about 5 ng/ml to about 2,500 ng/ml, preferably about 100 ng/ml to about 1,000 ng/ml, for about 0.5 hours to about 40 days post-administration, preferably about 7 days post-administration. Alternatively, a single administration of crystals of hGH or an hGH derivative, or a composition comprising such crystals, according to the present invention may provide an in vivo IGF-1 serum elevation of above about 50 ng/ml, preferably above about 100 ng/ml, for about 0.5 hours to about 40 days post-administration, preferably about 7 days post-administration. According to one embodiment of this invention, a single administration of crystals of hGH or an hGH derivative, or a composition comprising such crystals, provides an in vivo IGF-1 serum elevation over baseline IGF-1 level prior to said administration of greater than about 50 ng/ml from about 10 hours to about 72 hours post-administration and between about 0.5 ng/ml to about 50 ng/ml from about 72 hours to about 15 days post-administration or 72 hours to about 10 days post-administration.

According to this invention, a single administration is defined as between about 0.01 mg/kg/week to about 100 mg/kg/week hGH crystals or hGH derivative crystals, or a composition comprising such crystals, wherein the volume of the administration is between 0.1 ml and about 1.5 ml. For example, pediatric growth hormone deficiency may be dosed with hGH crystals or hGH derivative crystals, or a composition comprising such crystals, at about 0.3 mg/kg/week, e.g., about 9 mg for a 30 kg child. Turner syndrome may be dosed with hGH crystals or hGH derivative crystals, or a composition comprising such crystals, at about 0.375 mg/kg/week, e.g., about 11.25 mg for a 30 kg child. Additionally, adult growth hormone deficiency may be dosed with hGH at about 0.2 mg/kg/week, e.g., about 16 mg for a 80 kg adult. AIDS wasting disease may be dosed with hGH at 6 mg/day, e.g., 42 mg/week.

In yet another embodiment of this invention, crystals of hGH or an hGH derivative, or composition comprising such crystals, display a relative bioavailability similar to that of soluble hGH in a mammal. The crystals according to this invention have a relative bioavailability of at least 50% or greater compared to that of soluble hGH, delivered by the same route (e.g., subcutaneous or intramuscular injection), wherein said bioavailability is measured by the area under curve (AUC) of total in vivo hGH serum concentration for said soluble hGH and said crystal. Crystals of hGH or an hGH derivative are thus characterized by an advantageous in vivo dissolution rate.

The present invention further provides methods of administering crystals of hGH or an hGH derivative to a mammal having a disorder associated with human growth hormone deficiency or which is ameliorated by treatment with hGH. The method comprises the step of administering to the mammal a therapeutically effective amount of a crystal of hGH or an hGH derivative. Alternatively, the method comprises the step of administering to the mammal an effective amount of a composition comprising crystals of hGH or an hGH derivative alone or with an excipient. Various embodiments of crystals of hGH or an hGH derivative according to this invention are: calcium crystals, monovalent crystals, protamine crystals or polyarginine crystals of hGH or an hGH derivative. Such crystals, or compositions comprising them, may be administered by a time regimen of about once every three days, about once a week, about once every two weeks or about once every month.

Disorders related to hGH insufficiency that may be treated according to this invention include, but are not limited to: adult growth hormone deficiency, pediatric growth hormone deficiency, Prader-Willi syndrome, Turner syndrome, short bowel syndrome, chronic renal insufficiency, idiopathic short stature, dwarfism, hypopituitary dwarfism, bone regeneration, female infertility, intrauterine growth retardation, AIDS-related cachexia, Crohn's disease, burns, as well as other genetic and metabolic disorders. In one embodiment of this invention, the disorder is pediatric growth hormone deficiency and treatment results in annualized growth velocity of between about 7 cm and about 11 cm in the child undergoing treatment.

In another embodiment of this invention, a calcium crystal of hGH or an hGH derivative may serve as a useful adjunct for bone therapy, as well as treatment of human growth hormone deficiency in a mammal.

The present invention also provides methods for inducing weight gain in a mammal, comprising the step of administering to said mammal a therapeutically effective amount of crystals of hGH or an hGH derivative. Alternatively, such methods comprise the step of administering to said mammal a therapeutically effective amount of a composition comprising crystals of hGH or an hGH derivative and an excipient. In one embodiment of such methods, the weight gain induced in a hypophysectomized rat is between about 5% and about 40% after administration of said crystals by injection once a week.

Crystals of hGH, crystals of an hGH derivative or compositions comprising them alone, or with an excipient, may be administered alone, or as part of a pharmaceutical, therapeutic or prophylactic preparation. They may be administered by any conventional administration route including, for example, parenteral, oral, pulmonary, nasal, aural, anal, dermal, ocular, intravenous, intramuscular, intraarterial, intraperitoneal, mucosal, sublingual, subcutaneous, transdermal, topical, buccal or intracranial routes.

In one embodiment of the invention, crystals of hGH or an hGH derivative, or compositions comprising them, with or without an excipient, are administered by oral route or parenteral route. In a preferred embodiment, crystals of hGH or an hGH derivative, or compositions comprising them, with or without an excipient, are administered by subcutaneous or intramuscular route.

In a preferred embodiment, the crystals or compositions of this invention, are administered by subcutaneous route, using a needle having a gauge greater than or equal to 27. In one embodiment of this invention, the needle gauge may be equal to 30. The crystals or compositions may be administered from a pre-filled syringe or a meta dose infusion pump. Alternatively, they may be administered by needle-free injection.

This invention advantageously permits sustained release of hGH into a mammal. In one embodiment, the crystals or compositions according to this invention are administered about once a week. In another embodiment, the crystals or compositions according to this invention are administered about once every two weeks. In yet another embodiment, the crystals or compositions according to this invention are administered about once every month. It will be appreciated by those of skill in the art that the specific treatment regimen will depend upon factors such as the disease to be treated, the age and weight of the patient to be treated, general physical condition of the patient and judgment of the treating physician.

According to one embodiment, compositions comprising crystals of hGH or an hGH derivative according to the present invention are characterized by an hGH concentration greater than about 0.1 mg/ml. For example, that concentration may be between about 0.1 mg/ml and about 100 mg/ml. Alternatively, those compositions may be characterized by an hGH concentration between about 1 mg/ml and about 100 mg/ml or between about 10 mg/ml and about 100 mg/ml. Such compositions also include the following components: mannitol—about 0.5 mg/ml to about 100 mg/ml; sodium acetate—about 5 mM to about 250 mM (preferably about 25 mM to about 150 mM; Tris HCl—about 5 mM to about 100 mM; pH about 6.0 to about 9.0 (preferably about 6.5 to about 8.5); PEG (MW 800-8000, preferably 3350, 4000, 6000 or 8000)-0 to about 25%; protamine, preferably a 3:1 ratio of hGH:protamine; and polyarginine, preferably a 5:1 ratio of hGH:polyarginine. Such compositions may optionally comprise: sucrose—0 mg/ml to about 100 mg/ml; amino acids (e.g., arginine and glycine)—0 mg/ml to about 50 mg/ml; preservatives (antimicrobial, phenol, metacresol, benzyl alcohol, parabenzoate (paraben))—0% to about 5% (preferably 0% to about 0.9%); and polysorbate—0 mg/ml to about 10 mg/ml. According to one embodiment, compositions according to this invention are characterized by 80% effective loading.

A preferred formulation vehicle according to the present invention comprises about 100 mM sodium acetate, about 5% PEG 6000 MW and about 25 mM Tris.HCl, pH 7.5. An hGH composition prepared using such a vehicle may comprise: about 9.35 mg/ml crystalline hGH and about 1.81 mg/ml polyarginine (or about 3.12 mg/ml protamine). As will be appreciated by those of skill in the art, given that compositions according to this invention may comprise about 1 mg/ml to about 100 mg/ml hGH concentration, the polyarginine (or protamine) concentration should be adjusted accordingly, so that it is sufficient to maintain a 5:1 rhGH:polyarginine (w/w) ratio or a 3:1 hGH:protamine (w/w) ratio and maintain low solubility and release of hGH of about 5 ng/ml. For example, for the above-described formulation, if the desired crystalline hGH concentration is about 20 mg/ml, the polyarginine (or protamine) concentration should be about 4 mg/ml.

The present invention further provides methods for preparing crystals of hGH or an hGH derivative. One such method comprises the steps of: (a) mixing a solution of human growth hormone or a human growth hormone derivative with a crystallization solution, said crystallization solution comprising a salt and an ionic polymer; and (b) incubating said solution for greater than about 12 hours at a temperature between about 4° C. and about 37° C., until crystals of human growth hormone or a human growth hormone derivative are formed. In another embodiment, the method comprises the steps of: (a) mixing a solution of human growth hormone or a human growth hormone derivative with a crystallization solution, said crystallization solution comprising a salt and a precipitant; and (b) incubating said solution for greater than about 16 hours at a temperature between about 4° C. and about 37° C., until crystals of human growth hormone or a human growth hormone derivative are formed. In another embodiment, the solution at step (b) of either method described above can be incubated for greater than about a week at a temperature of about 15° C. In a preferred embodiment, the crystals of hGH or hGH derivative are calcium crystals, monovalent cation crystals, Protamine crystals or polyarginine crystals and the ionic polymer is Protamine or polyarginine. In another embodiment, the ionic polymer is polylysine or polyorthinine. In yet another embodiment, the ionic polymer is a mixture of any two or more of protamine, polyarginine and polylysine.

The salt in step (a) of the above-described methods may be either monovalent or divalent and inorganic or organic. A preferred embodiment of a divalent salt is a calcium salt. In a more preferred embodiment, the calcium salt is selected from the group consisting of: calcium acetate, calcium chloride, calcium gluconate and calcium sulfate. In yet a more preferred embodiment, the calcium salt is calcium acetate. In another preferred embodiment, the monovalent cation is selection from the group consisting of lithium, sodium, potassium and ammonium. In a more preferred embodiment, the monovalent cation is sodium.

In an alternate preferred embodiment of this invention, the monovalent cation salt is a sodium salt. In a more preferred embodiment, the sodium salt is selected from the group consisting of: sodium citrate, sodium phosphate and sodium acetate. In a yet more preferred embodiment, the sodium salt is sodium acetate.

In the above-described method, where the salt is a calcium salt or a monovalent cation salt, it is present in the crystallization solution of step (a) at a concentration between about 0.01 mM and about 1 M. In a preferred embodiment, this concentration is between about 25 and about 205 mM. Where the salt is a calcium salt, it is present in the crystallization solution of step (a) at a concentration between about 0.01 mM and 235 mM.

In a preferred embodiment, the crystallization solution of step (a) further comprises a pH buffer. In a more preferred embodiment, the pH buffer has a pH between about pH 6 and about pH 10. In a more preferred embodiment, the pH of the buffer is between about pH 7.5 and about pH 10. In a more preferred embodiment, the pH of the buffer is between about pH 7.0 and about pH 10. In yet a more preferred embodiment, the pH of the buffer is between about pH 6 and about pH 9. In yet a more preferred embodiment, the pH of the buffer is between about pH 7.8 and about pH 8.9.

In another aspect of the above-described methods, the pH buffer in step (a) is selected from the group consisting of: Tris, HEPES, acetate, phosphate, citrate, borate, imidazole and glycine. In a preferred embodiment of the above-described methods, the pH buffer in step (a) is selected from the group consisting of: bicarbonate, imidazole-malate, glycine, 2,2-Bis(hydroxymethyl)-2,2',2"-nitrilotriethanol ("bis-tris"), carbonate, N-(2-acetamido)-iminodiacetic acid, 2-amino-2-methyl-1,3-propanediol and (N-(1-acetamido)-2-aminoethane sulfonic acid.

In one of the above-described methods, the precipitant used to prepare crystals of hGH or an hGH derivative is typically polymeric, including low molecular weight polyalcohols and protamine. In another embodiment of the invention, the precipitant in step (a) of one of the above-described methods is a non-ionic polymer. In a preferred embodiment, the non-ionic polymer is selected from the group consisting of: alcohols, polyethylene glycol (PEG) and polyvinyl alcohol or ethanol. In a more preferred embodiment, the precipitant is isopropyl alcohol or ethanol. In yet a more preferred embodiment, the PEG has a molecular weight between about 200 and about 8000. The PEG may have a molecular weight of 3350, 4000, 6000 or 8000. In a more preferred embodiment, the PEG has a molecular weight of about 6000. In yet another preferred embodiment, the PEG is present at a concentration between about 0.5% and about 12% w/v.

In another embodiment of one of the above-described methods, the precipitant in step (a) is an ionic polymer. In a preferred embodiment, the ionic polymer is selected from the group consisting of: protamine, polyarginine, polyornithine and polylysine.

The mixing step (a) of the above-described method comprises mixing a solution of hGH or an hGH derivative with a crystallization solution. In one embodiment of that method, the resulting concentration of hGH or hGH derivative in said crystallization solution is between about 1 mg/ml and about 1,000 mg/ml. In a preferred embodiment, the hGH or hGH derivative in said solution is present at a concentration between about 2 mg/ml and about 50 mg/ml. In a further embodiment, the hGH or hGH derivative in said solution is present at a concentration between about 10 mg/ml and about 25 mg/ml.

In a preferred embodiment of the above-described method for preparing crystals of hGH or an hGH derivative, the solution comprising hGH or an hGH derivative and the crystallization solution is incubated in step (b) for between about 0.25 day and about two days at a temperature of about 33° C. Alternatively, that temperature may be about 37° C. In another embodiment, the solution comprising hGH or an hGH derivative and the crystallization solution is incubated for between about 0.25 day and about two days at a temperature of about 25° C. In yet another embodiment, the solution comprising hGH or an hGH derivative and the crystallization solution is incubated for between about 0.25 day and about two days at a temperature of about 15° C.

The present invention further provides an alternate method of preparing crystals of hGH, crystals of an hGH derivative or compositions comprising such crystals and an excipient. This method comprises the steps of: (a) mixing a solution of hGH or an hGH derivative with a crystallization buffer to produce a crystallization solution; (b) adding deionized water to the crystallization solution; (c) adding an ionic small molecule or ionic polymer to said crystallization solution; (d) adding a salt to said crystallization solution; and (e) incubating the crystallization solution for between about 2 and about 168 hours at a temperature between about 10° C. and about 40° C., until crystals of hGH or an hGH derivative are formed. In a further embodiment of this invention, that incubation is carried out for between about 4 and about 48 hours. In another preferred embodiment, the crystallization solution at step (e) of the above-described method is incubated for between about 4 and about 48 hours at a temperature between about 4° C. and about 40° C., until crystals of hGH or an hGH derivative are formed. According to an alternate embodiment, the above-described method is carried out with an optional step after step (b). That optional step comprises adding a precipitant to the crystallization solution. In a further embodiment of the above-described method, step (c) is optional. Whether or not those optional steps are employed, in a preferred embodiment, the crystallization solution at step (e) is incubated for between about one and about two days at a temperature between about 15° C. and about 37° C. In another preferred embodiment, the crystallization solution at step (e) is incubated for between about one and about two days at a temperature between about 4° C. and about 37° C.

In a preferred embodiment according to this invention, in step (d) of the above-described method, the salt is calcium salt or a monovalent cation salt. In a preferred embodiment for calcium crystals, the calcium salt is selected from the group consisting of: calcium acetate, calcium chloride, calcium gluconate and calcium sulfate. In yet a more preferred embodiment, the calcium salt is calcium acetate. In a preferred embodiment, the calcium acetate is in the form of an aqueous solution having a pH between about 3 and about 9.0. In a more preferred embodiment, the aqueous solution of calcium acetate has a pH between about 7.0 and about 8.6. In another embodiment, the calcium acetate in the crystallization solution at step (e) is present at a concentration between about 0.1 mM and about 205 mM. In a more preferred embodiment, the calcium acetate in the crystallization solution at step (e) is present at a concentration between about 85 mM and about 100 mM.

In a more preferred embodiment, the monovalent cation salt is selected from the group consisting of lithium, sodium, potassium and ammonium. In yet a more preferred embodiment, the monovalent cation salt in step (d) of the above-described method is sodium. Similarly, in a more preferred embodiment, the monovalent cation salt is selected from the group consisting of: sodium citrate, sodium phosphate and sodium acetate. In yet a more preferred embodiment, the monovalent cation salt is sodium acetate. In a preferred embodiment, the sodium acetate is in the form of an aqueous solution having a pH between about 3 and about 9.0. In a more preferred embodiment, the aqueous solution of sodium acetate has a pH between about 7.0 and about 8.6. In another embodiment, the sodium acetate in the solution at step (e) is present at a concentration between about 0.5 mM and about 800 mM. In a more preferred embodiment, the sodium acetate in the crystallization solution at step (e) is present at a concentration between about 100 mM and about 500 mM. That concentration may also be between about 85 mM and about 100 mM.

In yet another preferred embodiment, the hGH or hGH derivative in the crystallization solution at step (e) of the above-described method is present at a concentration between about 2 mg/ml and about 17.5 mg/ml. In another preferred embodiment, the hGH or hGH derivative in the crystallization solution at step (e) is present at a concentration between about 14.5 mg/ml and about 15.5 mg/ml. In a further embodiment, the hGH or hGH derivative in the crystallization solution at step (e) is present at a concentration between about 2 mg/ml and about 100 mg/ml.

In a preferred embodiment, the crystallization buffer at step (a) of the above-described method is selected from the group consisting of Tris-HCl, HEPES, acetate, phosphate, citrate, borate, imidazole and glycine. Alternatively, the crystallization buffer is selected from the group consisting of: Tris-HCl, glycine, HEPES, imidazole, Bis-Tris, AMP (2-amino-2-methylpropanol), AMPD (2-amino-2-methyl-1, 3-propanediol), AMPSO (3-([1,1-dimethyl-2-hydroxyethyl] amino)-2-hydroxypropane sulfonic acid), bicine, ethanolamine, glyclglycine, TAPS, Taurin, Triane, and mixtures thereof. In another preferred embodiment, the crystallization buffer in solution at step (a) is present at a concentration between about 10 mM and about 800 mM.

In another embodiment of the above-described method, the crystallization buffer in step (a) is present at a pH between about 3 and about 10. In a preferred embodiment, the crystallization buffer is present at a pH between about 6 and about 9. In yet another preferred embodiment, the crystallization buffer is present at a pH between about 7.5 and about 10.

In another preferred embodiment, the pH of the crystallization buffer in solution at step (e) of the above-described method is between about 3 and about 10. In a more preferred embodiment, the pH of the crystallization buffer in solution is between about 6 and about 9.5. In yet a more preferred embodiment, the pH of the crystallization buffer in solution is between about 7.5 and about 9.5.

In a preferred embodiment of those methods which include the optional step following step (b) of adding a precipitant to the crystallization solution, that precipitant is a non-ionic small molecule or a non-ionic polymer. In a preferred embodiment, the non-ionic polymer is selected from the group consisting of polyethylene glycol (PEG), polyvinyl alcohol and mixtures thereof. In another preferred embodiment, the PEG has a molecular weight selected from the group consisting of between about 200 and about 8000, about 6000, about 4000 and about 3350. In yet another preferred embodiment, PEG is present in the crystallization solution at a concentration between about 0.5% and about 20% (w/v). In another preferred embodiment of the above-described method, the precipitant is selected from the group consisting of: amino acids, peptides, polyamino acids and mixtures thereof.

In another preferred embodiment, in step (c) of the above-described method, the ionic polymer is selected from the group consisting of: protamine, polyarginine, polylysine, polyornithine and octarginine. In another preferred embodiment, in step (c) of the above-described method, polyarginine is added in a ratio of hGH:polyarginine (mg:mg) ranging between 5:1 and about 1:25. The resulting crystallization solution is incubated at a temperature ranging between about 15° C. and about 37° C. for about 16 hours to about 48 hours.

The present invention provides yet another method of preparing crystals of human growth hormone, crystals of a human growth hormone derivative or compositions comprising such crystals and an excipient. This method comprises the steps of: (a) mixing a solution of human growth hormone or a human growth hormone derivative with a crystallization buffer to produce a crystallization solution; (b) adding deionized water to said crystallization solution; (c) adding a precipitant to said crystallization solution; (d) adding a salt to said crystallization solution; (e) incubating the crystallization solution for between about 2 and about 168 hours at a temperature between about 10° C. and about 40° C., until crystals of human growth hormone or a human growth hormone derivative are formed; and (f) adding an ionic polymer to said crystals of human growth hormone or a human growth hormone derivative. According to one embodiment of the above-described method, step (f) is optional. In a preferred embodiment, the crystallization solution at step (e) is incubated for between about one and about two days at a temperature between about 15° C. and about 37° C. In a another preferred embodiment, the crystallization solution at step (e) is incubated for between about one and about two days at a temperature between about 4° C. and about 37° C. In a further embodiment of this invention, that incubation is carried out for between about 2 and about 48 hours. In another preferred embodiment, the crystallization solution at step (e) of the above-described method is incubated for between about 4 and about 48 hours at a temperature between about 4° C. and about 40° C., until crystals of hGH or an hGH derivative are formed.

In a preferred embodiment according to this invention, in step (d) of the above-described method, the salt is calcium salt or a monovalent cation salt. In a more preferred embodiment, the calcium salt is selected from the group consisting of: calcium acetate, calcium chloride, calcium gluconate and calcium sulfate. In yet a more preferred embodiment, the calcium salt is calcium acetate. In a preferred embodiment, the calcium acetate is in the form of an aqueous solution having a pH between about 3 and about 9.0. In a more preferred embodiment, the aqueous solution of calcium acetate has a pH between about 7.0 and about 8.6. In another embodiment, the calcium acetate in the crystallization solution at step (e) is present at a concentration between about 0.1 mM and about 205 mM. In a more preferred embodiment, the calcium acetate in the crystallization solution at step (e) is present at a concentration between about 85 mM and about 100 mM.

In a more preferred embodiment, the monovalent cation is selected from the group consisting of lithium, sodium, potassium and ammonium. In yet a more preferred embodiment, the monovalent cation is sodium. Similarly, in a more preferred embodiment, the monovalent cation salt is selected from the group consisting of sodium citrate, sodium phosphate and sodium acetate. In yet a more preferred embodiment, the monovalent cation salt is sodium acetate. In a preferred embodiment, the sodium acetate is in the form of an aqueous solution having a pH between about 3 and about 9.0. In a more preferred embodiment, the aqueous solution of sodium acetate has a pH between about 7.0 and about 8.6. In another embodiment, the sodium acetate in the solution at step (e) is present at a concentration between about 0.5 mM and about 800 mM. In a more preferred embodiment, the calcium acetate in the crystallization solution at step (e) is present at a concentration between about 100 mM and about 500 mM. Alternatively, that concentration may also be between about 85 mM and about 100 mM.

In yet another preferred embodiment, the hGH or hGH derivative in the crystallization solution at step (e) of the above-described method is present at a concentration between about 2 mg/ml and about 17.5 mg/ml. In another preferred embodiment, the hGH or hGH derivative in the crystallization solution at step (e) is present at a concentration between about 14.5 mg/ml and about 15.5 mg/ml. In a further embodiment, the hGH or hGH derivative in the crystallization solution at step (e) is present at a concentration between about 2 mg/ml and about 100 mg/ml.

In a preferred embodiment, the crystallization buffer at step (a) of the above-described method is selected from the group consisting of: Tris-HCl, HEPES, acetate, phosphate, citrate, borate, imidazole and glycine. In another preferred embodiment, the crystallization buffer in solution at step (a) is present at a concentration between about 10 mM and about 800 mM.

In another embodiment of the above-described method, the crystallization buffer in step (a) is present at a pH between about 3 and about 10. In a preferred embodiment, the crystallization buffer is present at a pH between about 6 and about 9. In yet another preferred embodiment, the crystallization buffer is present at a pH between about 7.5 and about 10.

In another preferred embodiment, the pH of the crystallization buffer in solution at step (e) of the above-described method is between about 3 and about 10. In a more preferred embodiment, the pH of the crystallization buffer in solution is between about 6 and about 9.5. In yet a more preferred embodiment, the pH of the crystallization buffer in solution is between about 7.5 and about 9.5.

In a preferred embodiment, in step (c) of the above-described method, the precipitant is a non-ionic small molecule or a non-ionic polymer. In a preferred embodiment, the non-ionic polymer is selected from the group consisting of: polyethylene glycol (PEG), polyvinyl alcohol and mixtures thereof. In another preferred embodiment, the PEG has a molecular weight selected from the group consisting of: between about 200 and about 8000, about 6000, about 4000 and about 3350. In yet another preferred embodiment, PEG is present in the crystallization solution at a concentration between about 0.5% and about 20% (w/v). In another preferred embodiment, in step (c) of the above-described method, the precipitant is selected from the group consisting of: amino acids, peptides, polyamino acids and mixtures thereof.

In another preferred embodiment, in step (f) of the above-described method, the ionic polymer is selected from the group consisting of: protamine, polyarginine, polylysine, polyornithine and octarginine. In another preferred embodiment, in step (f) of the above-described method, polyarginine is added in a ratio of hGH:polyarginine (mg:mg) ranging between about 5:1 and about 1:25. In an alternate embodiment, polyarginine is added in a ratio of hGH:polyarginine (mg:mg) ranging between about 1:5 and about 1:25. The resulting solution in step (f) is incubated at a temperature ranging between about 15° C. and about 37° C. for about 16 hours to about 48 hours. The effect of the polymer on the rate of dissolution of the crystals of hGH or an hGH derivative is reflected by the number of washes required for complete dissolution. A control crystal requires about 7 to about 13 washes for complete dissolution, while a crystal prepared with polyarginine requires between about 30 to 90 identical washes of dissolution buffer for complete dissolution. Washes are wash steps in a sequential dissolution process (see Example 5).

In alternate embodiments of any of the above-described methods, the calcium salt or the monovalent cation salt may be present in the crystallization solution at a concentration between about 0.01 M and about 1 M or between about 25 mM and about 205 mM. In alternate embodiments of any of the above-described methods, the crystallization solution is incubated for a time and a temperature selected from the group consisting of: between about 0.25 day and about two days at a temperature of about 33° C.; between about 0.25 day and about two days at a temperature of about 25° C. and between about 0.25 day and about two days at a temperature of about 15° C.

The present invention also includes methods for screening crystals of hGH or an hGH derivative for use in a therapeutic formulation. The steps of such methods include: (1) washing said crystals of hGH or an hGH derivative with a dissolution buffer at a temperature of about 37° C. (for example, 2 mg of crystals and 1 ml of dissolution buffer) and (2) measuring the in vitro dissolution rate of said crystals of hGH or an hGH derivative per wash in said dissolution buffer, wherein said in vitro dissolution rate of said crystals is between about 2% and about 16% of said crystals for between about 10 minutes and about 1500 minutes, with about 2 minutes and 32 minutes per wash step in a sequential dissolution process (see Example 5). The in vitro dissolution rate of said crystals may also be between about 4% and about 10% of said crystals over about 15 minutes or between about 0.04 and about 0.32 mg of said crystals over about 15 minutes.

In order that this invention may be better understood, the following examples are set forth. These examples are for the purpose of illustration only and are not to be construed as limiting the scope of the invention in any manner.

EXAMPLES

The following materials were used in the examples set forth below.

Materials

Commercially available recombinant human growth hormone (rhGH) was from BresaGen Ltd. (Thebarton, Australia), polyethylene glycol with average molecular weight of 4000 or 6000 (PEG-4000 or PEG-6000) was from Hampton Research (Laguna Niguel, Calif.) and protamine sulfate was purchased through Fisher from ICN Biomedicals Inc. (Pittsburgh, Pa.). Ammonium phosphate, Tris-HCl, sodium citrate, dibasic sodium phosphate, calcium acetate, calcium chloride, zinc acetate, HEPES, sodium chloride, potassium chloride, sodium azide, isopropanol (IPA), ethanol and polyethylene glycol monomethyl ether were each obtained from Fisher (Pittsburgh, Pa.). Sprague-Dawley rats were obtained from Charles River Laboratories (Worcester, Mass.) or from Biomedical Research Laboratories, Inc. (Worcester, Mass.). Polyarginine was obtained from Sigma (St. Louis).

Analytical Techniques and Assays

Reversed Phase High Performance Liquid Chromatography. Reversed phase high performance liquid chromatograms (RP-HPLC) were acquired on an Agilent 1100 series HPLC (Palo Alto, Calif.) equipped with a C5, 5 cm×4.6 mm, 3 μm column (Supelco, Bellefonte, Pa.). Samples were dissolved in dissolution buffer (50 mM HEPES pH 7.2, 140 mM NaCl, 10 mM KCl and 0.02% (v/v) $NaN_3$) and filtered (0.2 μm) prior to injection. Elution profiles were monitored at 214 and 280 nm using gradient method of solvents A and B. Solvent A consisted of 99.9% deionized water/0.1% TFA. Solvent B consisted of 99.9% Acetonitrile/0.1% TFA. All chemicals were HPLC grade obtained from Fisher. Elutions were performed over 15 min., using a gradient design of 0-2 min 40-50% B, 2-12 min 50-60% B, and 12-15 60-85% B. A flow rate of 1 ml/min and a column temperature of 35° C. was maintained throughout the run. Data was analyzed using Agilent Chemstation software (Palo Alto, Calif.).

The concentration of either protamine or polyarginine in sample preparations was determined using a gradient method of solvents A (99.9% deionized water/0.1% TFA) and B (99.9% acetonitrile/0.1% TFA). Elutions were performed over 20 minutes at a flow rate of 1 ml/min, using a gradient design of 0-2.5 min 95:5 (A:B), 2.5-7.5 min 65:35 (A:B), 7.5-15.5 min 25:75 (A:B), 15.5-17.0 min 25:75 (A:B), 17-17.1 min 95:5 (A:B). Typical elution of either Protamine or polyarginine was obtained at 6.2 min with intact hGH eluting at 14 min. AUC calculations were determined at 213 nm. Content of Protamine and/or polyarginine (mg/ml) additives was calculated from calibration curves generated from each of the respective additives. This same method may be used to analyze excipient released from the complexes.

Associated degraded hGH was determined with a separate but similar reversed-phase method. For example, the analysis was performed on C5 Supelco Discovery Bio Wide Pore Column (5 cm×4.6 mm, 3 μm particle size, 30 nm pore size) with a thermostat temperature of 37° C. being maintained throughout the run. The elution profiles were monitored using a gradient method having a mobile phase A (20% ACN, 80% $H_2O$, 0.1% TFA) and mobile phase B (20% ACN, 80% 2-propanol, 01.% TFA). The gradient system changed from 20% to 45% B over 0 to 5 min, from 45% to 55% B over 5 to 15 min, from 55% to 90% over 15 to 15.1 min, 90% B static until 17 min and immediately following this step, 20% B was re-established until 20 min was reached.

Size Exclusion Chromatography. High performance size exclusion chromatograms (SEC-HPLC) were acquired on an Agilent 1100 series HPLC (Palo Alto, Calif.) equipped with a TSK-Gel G2000SWXL column (part# 08450, Tosoh Biosep LLC, Montgomeryville, Pa.) (7.8 mm×30 cm, 5 μm) and an Agilent 1100 series MWD (UV). Samples were dissolved in 0.2 ml of dissolution buffer and 0.2 μm filtered prior to injection into Agilent 1100 series temperature controlled Autosampler. Elution profiles were monitored at 214 and 280 nm, with a mobile phase of 50 mM Tris-HCl, 150 mM Nacl, 0.05% $NaN_3$, pH 7.5. Column temperature was maintained at 25° C., solvents were degassed using an Agilent 1100 series degasser.

UV-VIS absorption and Optical Microscopy. UV-VIS spectrophotographs were obtained on a Beckman DU 7400 spectrophotometer, Beckman Coulter Inc., Fullerton, Calif. Optical micrographs were obtained by bright field imaging using an Olympus BX-51 microscope and captured by a Sony DXC-970MD 3CCD color digital video camera using Image-Pro software, Media Cybernetics L. P., Silver Springs, Md., under the magnifications of 40× to 400×.

Transmission Electron Microscopy (TEM). TEM analysis was carried out as follows. Suspensions of hGH crystals in mother liquor were washed twice with water to remove excess mother liquor and then negatively stained with 0.5% uranyl acetate for 1 hour. The stained hGH crystal suspensions (1-5 μL) were transferred onto copper TEM grids. Excess liquid was wicked away and the sample grid briefly air-dried. The TEM grid was transferred to the sample stage of a JEOL 1210 transmission electron microscope and images were collected using an 80 KV electron beam. A very well organized lattice structure was observed inside the crystals, with the orientation in alignment with the crystal prism axis.

Example 1

Crystallization of hGH with ammonium phosphate. Commercially available hGH (50 mg) was first dissolved in 15 ml Tris-HCl (10 mM, pH 8.0) and dialyzed against 2×4000 ml Tris-HCl (10 mM, pH 8.0) using a Pierce Dialyzer cartridge having a molecular weight cutoff (MWCO) of 10,000. Protein concentration was adjusted by centrifugation using a Millipore concentrator (MWCO 10,000) at 4000 rpm for 20-30 minutes. The concentration of hGH was found in a range of 30-45 mg/ml, as measured by absorbance at 280 nm/0.813 (1 mg/ml hGH $A_{280}$=0.813 absorbance units) Deionized water was added to the solution to yield a final protein concentration of 10-20 mg/ml. Crystals of hGH were grown by adding ammonium phosphate ($NH_4H_2PO_4$) (2.5 M; pH 8.9) to the solution, so that a final concentration of 860 mM $NH_4H_2PO_4$ was obtained. The solution was then incubated for 16 hours at 25° C. Needle-like crystals were obtained and imaged by optical microscopy. The crystals obtained were found to be approximately 8 to 15 μm in length, with a crystallization yield of greater than 90%. See FIG. 1.

Example 2

Figure 2:
FIG. 2 illustrates hGH crystals grown in the presence of 390 mM sodium citrate, as imaged by optical microscopy. See Example 2.

Crystallization of hGH with sodium citrate. Commercially available hGH was purified and concentrated as described in Example 1. Deionized water was added to the concentrated solution of hGH to yield a final protein concentration of 17.5 mg/ml. Crystals of hGH were grown by adding sodium citrate (Na-Citrate) (1.5 M) to the solution so that a final concentration of 390 mM Na-Citrate was obtained. No pH adjustment was required, aside from hGH already in 10 mM Tris-HCl. The solution was then incubated for 16 hours at 25° C. Needle-like crystals were obtained and imaged by optical microscopy. The crystals obtained were found to be less than 8 µm in length with a crystallization yield of greater than 85%. See FIG. 2.

Example 3

Crystallization of hGH with sodium phosphate. Commercially available hGH was purified and concentrated as described in Example 1. Deionized water was added to the concentrated hGH solution to yield a final protein concentration of 12.5-17.5 mg/ml. Tris-HCl (1 M, pH 8.6) was added to a final concentration of 100 mM. Crystals of hGH were grown by adding dibasic sodium phosphate ($Na_2HPO_4$) (1 M) to the solution so that a final concentration of 600 mM $Na_2HPO_4$ was obtained. The solution was then incubated for 16 hours at 25° C. Needle-like crystals were obtained and imaged by optical microscopy. The crystals obtained were found to be between 5 and 25 µm in length with a crystallization yield of greater than 75%. See FIG. 3.

Example 4

Figure 4:
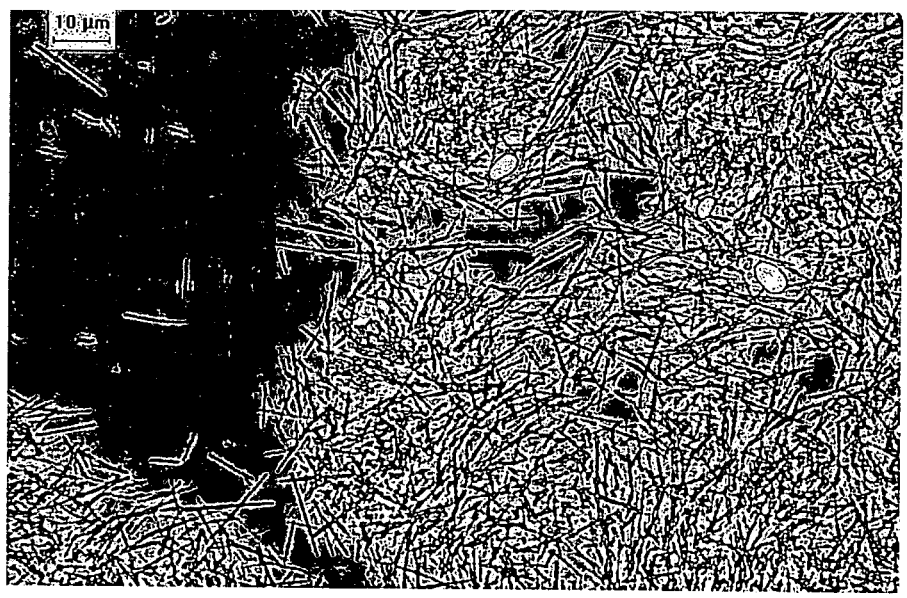
FIG. 4 illustrates hGH crystals grown in the presence of 85 mM calcium acetate and 100 mM Tris-HCl (pH 8.6) and co-crystallized with Protamine sulfate (1 mg/ml), as imaged by optical microscopy. See Example 4.

Crystallization of hGH with calcium acetate and Protamine sulfate. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. To this solution, Protamine sulfate was added to final concentration of 1 mg/ml. Crystals of hGH were grown by adding calcium acetate (Ca-Acetate) (1 M) to the solution so that a final concentration of 85 mM Ca-Acetate was obtained. The solution was then incubated for 8 hours at 37° C. Needle-like crystals were obtained and imaged by optical microscopy. The crystals obtained were found to be less than 20 µm in length with a crystallization yield of greater than 70%. See FIG. 4.

Example 5

Solubility profile of hGH crystals prepared by salt induced crystallization. After the incubation of the crystallization solutions in Examples 1-4, the crystals were pelleted and the remaining supernatant removed. The crystal pellets (0.4 mg) were resuspended in 0.200 ml of dissolution buffer (50 mM HEPES (pH 7.2), 140 mM NaCl, 10 mM KCl and 0.02% (v/v) $NaN_3$) by either pipetting or vortexing before being equilibrated for approximately 15 minutes at 37° C. The samples were then centrifuged at 10,000×g for 2 minutes and the supernatant was completely removed for determination of protein concentration measured at 280 nm by RP-HPLC, SEC-HPLC or UV-VIS. The crystalline pellets were further resuspended in 0.200 ml of dissolution buffer and the process repeated until no detectable protein was measured in the supernatant. This process is referred to as sequential dissolution.

Figure 5:
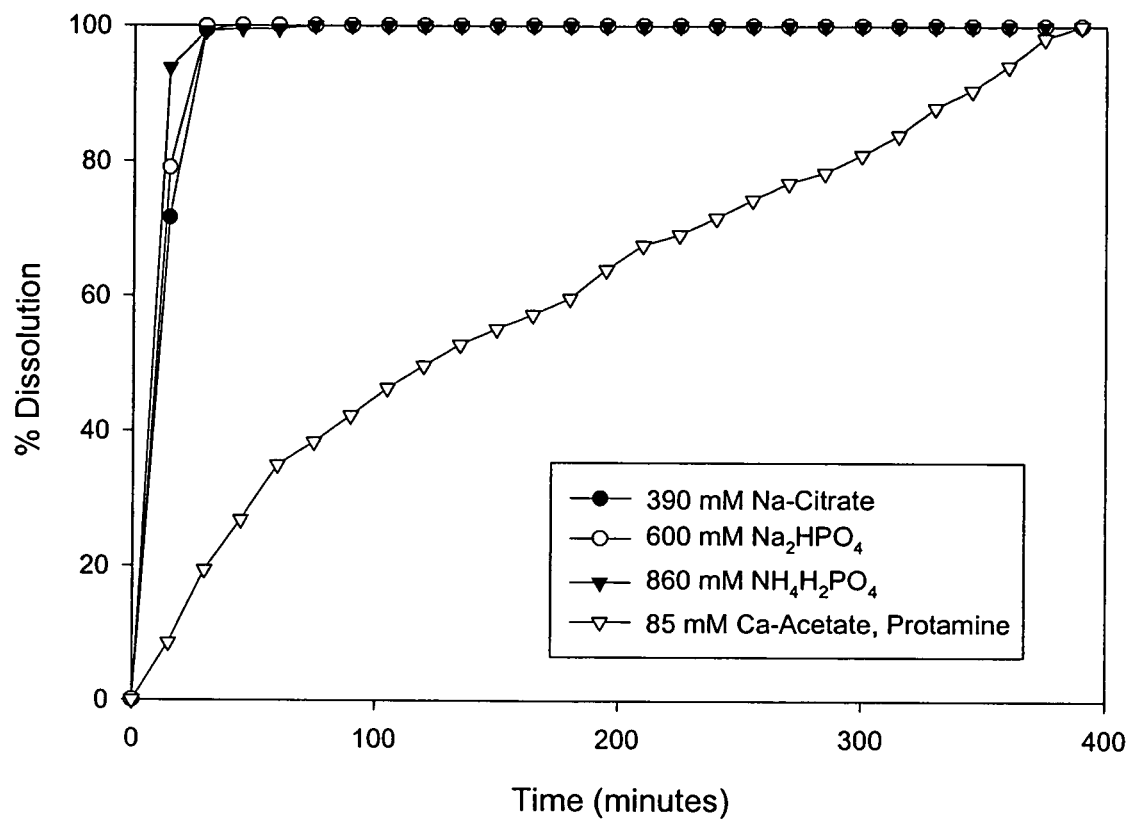
FIG. 5 shows solubility of hGH crystals generated from ammonium phosphate, sodium citrate, dibasic sodium phosphate and calcium acetate/Protamine precipitants as a function of time and monitored at 280 nm. See Example 5.

FIG. 5 shows the solubility behavior of various hGH crystals prepared with monovalent (Na or $NH_4$) or divalent (Ca) salts in Examples 1-4 above as a function of time in minutes. hGH dissolution was plotted as a cumulative percent release derived from RP-HPLC, wherein AUC values for protein samples were measured in mg/ml using a UV-VIS spectrophotometer. The data illustrates that hGH crystals prepared by the addition of 390 mM Na-Citrate are completely dissolved after 60 minutes. In addition, hGH crystals prepared by the addition of 600 mM $Na_2HPO_4$ or 860 mM $NH_4H_2PO_4$ are completely dissolved after 60 or 75 minutes, respectively. On the other hand, hGH crystals prepared by the addition of 85 mM Ca-Acetate and protamine sulfate dissolved completely after 390 minutes (see Table 1 below).

TABLE 1

Sequential dissolution test measured at 280 nm for salts of hGH in dissolution buffer-protein concentration was expressed as percent of total released

| Time (minutes) | 390 mM Na-Citrate (Ex. 2) | 600 mM $Na_2HPO_4$ (Ex. 3) | 860 mM $NH_4H_2PO_4$ (Ex. 1) | 85 mM Ca-Acetate + Protamine (Ex. 4) |
|---|---|---|---|---|
| 0 | 0.00 | 0.00 | 0.00 | 0.00 |
| 15 | 71.59 | 78.99 | 93.77 | 8.53 |
| 30 | 99.36 | 99.85 | 99.18 | 19.39 |
| 45 | 99.99 | 99.99 | 99.50 | 26.81 |
| 60 | 100.00 | 100.00 | 99.50 | 34.92 |
| 75 | 100.00 | 100.00 | 100.00 | 38.31 |
| 90 | 100.00 | 100.00 | 100.00 | 42.22 |
| 105 | 100.00 | 100.00 | 100.00 | 46.26 |
| 120 | 100.00 | 100.00 | 100.00 | 49.62 |
| 135 | 100.00 | 100.00 | 100.00 | 52.73 |
| 150 | 100.00 | 100.00 | 100.00 | 55.08 |
| 165 | 100.00 | 100.00 | 100.00 | 57.20 |
| 180 | 100.00 | 100.00 | 100.00 | 59.65 |
| 195 | 100.00 | 100.00 | 100.00 | 63.95 |
| 210 | 100.00 | 100.00 | 100.00 | 67.57 |
| 225 | 100.00 | 100.00 | 100.00 | 69.17 |
| 240 | 100.00 | 100.00 | 100.00 | 71.63 |
| 255 | 100.00 | 100.00 | 100.00 | 74.35 |
| 270 | 100.00 | 100.00 | 100.00 | 76.85 |
| 285 | 100.00 | 100.00 | 100.00 | 78.39 |
| 300 | 100.00 | 100.00 | 100.00 | 81.06 |
| 315 | 100.00 | 100.00 | 100.00 | 83.97 |
| 330 | 100.00 | 100.00 | 100.00 | 87.97 |
| 345 | 100.00 | 100.00 | 100.00 | 90.57 |
| 360 | 100.00 | 100.00 | 100.00 | 94.20 |
| 375 | 100.00 | 100.00 | 100.00 | 98.28 |
| 390 | 100.00 | 100.00 | 100.00 | 100.00 |

Example 6

Figure 6:
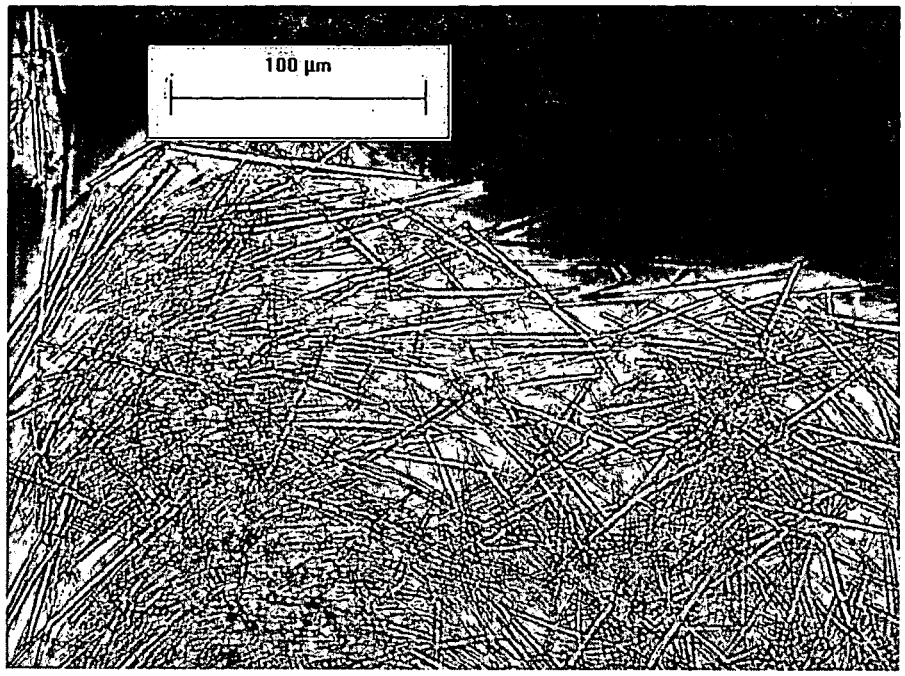
FIG. 6 illustrates hGH crystals grown in the presence of 10% (v/v) isopropanol, 85 mM calcium acetate and 100 mM Tris-HCl (pH 8.6), as imaged by optical microscopy. See Example 6.

Crystallization of hGH with calcium acetate and 10 isopropanol. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. Crystals of hGH were grown by adding Ca-Acetate (1 M) to the solution so that a final concentration of 85 mM Ca-Acetate was obtained. To this solution, 10% (v/v) isopropanol (IPA) was added. The solution was then incubated for 16 hours at 25° C. Rod-like crystals were obtained and imaged by optical microscopy. The crystals obtained were found to be greater than 100 µm in length with a crystallization yield of greater than 85%. See FIG. 6.

Example 7

Figure 7:
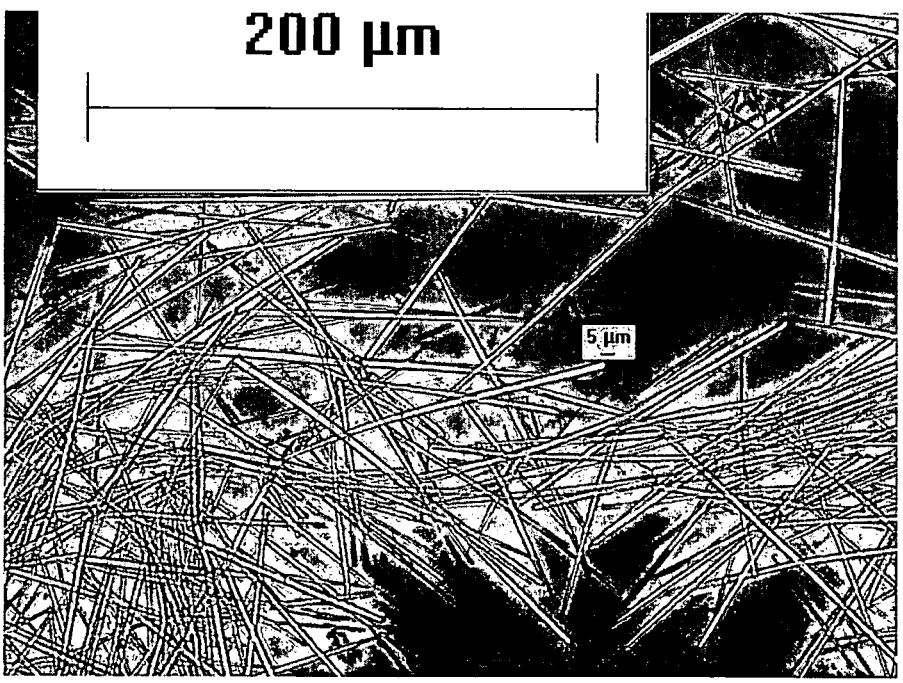
FIG. 7 illustrates hGH crystals grown in the presence of 5% (v/v) isopropanol, 85 mM calcium chloride and 100 mM Tris-HCl (pH 8.6), as imaged by optical microscopy. See Example 7.

Crystallization of hGH with calcium chloride and 5% isopropanol. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. Crystals of hGH were grown by adding calcium chloride ($CaCl_2$) (1 M) to the solution so that a final concentration of 85 mM $CaCl_2$ was obtained. To this solution, 5% (v/v) IPA was added. The solution was then incubated for 16 hours at 25° C. Rod-like needles were obtained and imaged by optical microscopy. The crystals obtained were found to be greater than 200 µm in length with a crystallization yield of greater than 85%. See FIG. 7.

Example 8

Figure 8:
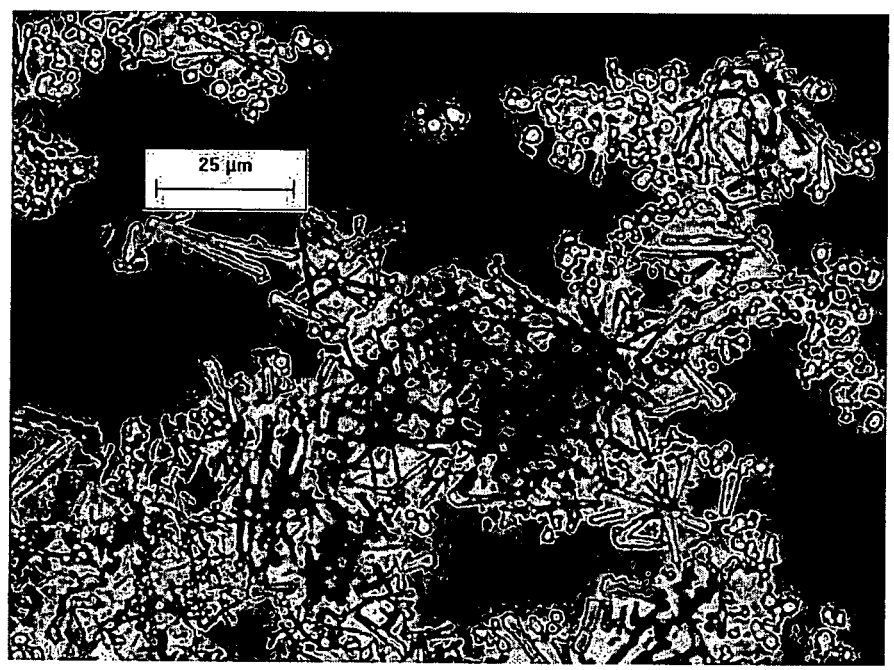
FIG. 8 illustrates hGH crystals grown in the presence of 10% (v/v) ethanol, 10% (v/v) PEG-6000 and 100 mM Tris-HCl (pH 8.6), as imaged by optical microscopy. See Example 8.

Crystallization of hGH with 10% PEG-6000 and 10% ethanol. Commercially available hGH was purified and concentrated as described in Example 1. Deionized water was added to the concentrated hGH solution to yield a final protein concentration of 25 mg/ml. Tris-HCl (1 M, pH 8.6) was added to a final concentration of 100 mM. Crystals of hGH were grown by adding 10% (v/v) PEG-6000 and 10% (v/v) ethanol (EtOH) to the solution. The solution was then incubated for 16 hours at 37° C. Rod-like crystals were obtained and imaged by optical microscopy. The crystals obtained were found to be less than 25 µm in length with a crystallization yield of greater than 70%. See FIG. 8.

Example 9

Solubility profile of hGH crystals prepared with alcohol. After the incubation of the crystallization solutions prepared in Examples 6-8, the crystals were pelleted and the remaining supernatant removed. The crystal pellets were resuspended in 0.200 ml of dissolution buffer (see Example 5) by either pipetting or vortexing before being equilibrated for approximately 15 minutes at 37° C. The samples were then centrifuged at 10,000×g for 2 minutes and the supernatant was removed for determination of protein concentration measured at 280 nm by RP-HPLC, SEC-HPLC or UV-VIS. hGH dissolution was measured as a cumulative percentage and derived from AUC values or UV-VIS mg/ml measurements. The crystalline pellets were further resuspended in dissolution buffer and the process repeated until no detectable protein was measured in the supernatant.

Figure 9:
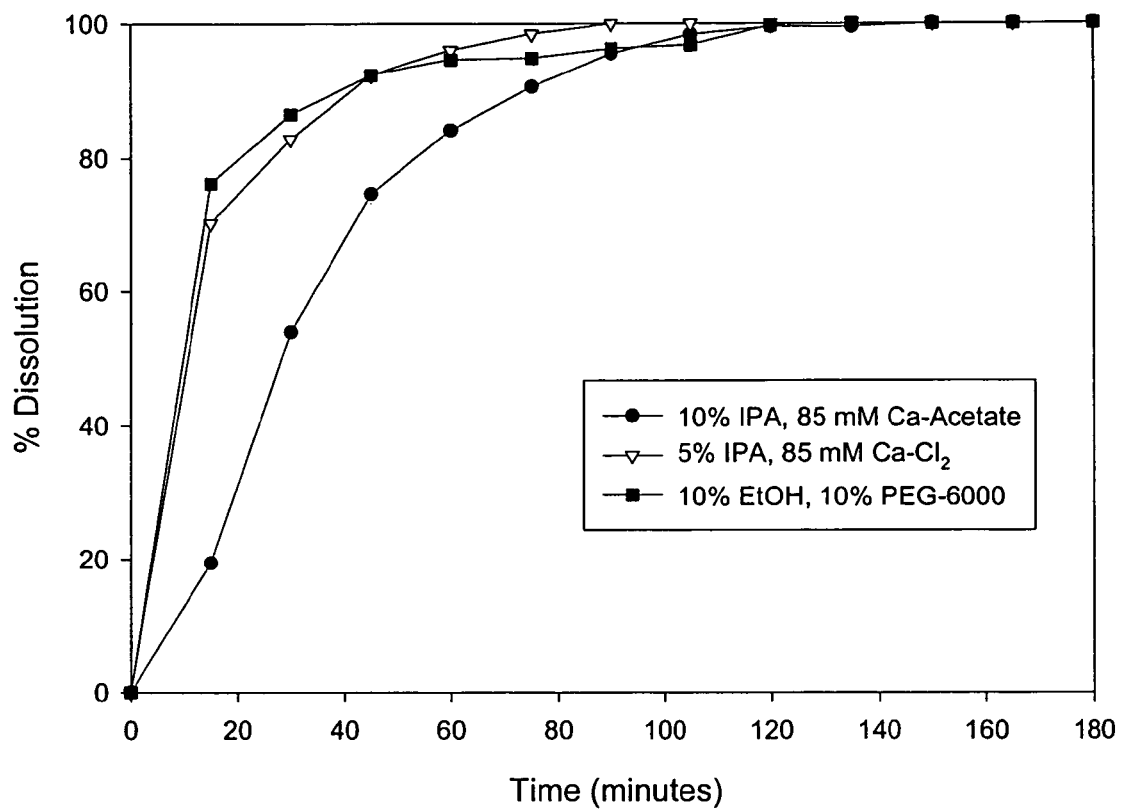
FIG. 9 shows solubility of hGH crystals grown according to Examples 6-8 monitored at 280 nm as a function of time in minutes. See Example 9.

FIG. 9 and Table 2 illustrate the solubility behavior of hGH crystals prepared with 10% IPA/85 mM Ca-Acetate, 5% IPA/ 85 mM $CaCl_2$ and 10% EtOH/10% PEG-6000 as a function of time in minutes. The results demonstrate that hGH crystals prepared by the addition of 10% IPA/85 mM Ca-Acetate were completely dissolved after 150 minutes, whereas hGH crystals prepared by the addition of 5% IPA/85 mM $CaCl_2$ and 10% EtOH/10% PEG-6000 completely dissolved at 120 minutes and 135 minutes, respectively.

TABLE 2

In vitro dissolution results of hGH crystals prepared with alcohol (Examples 6–8)-protein concentration was measured at 280 nm and expressed as percent of total released

| Time (minutes) | 10% IPA, 85 mM Ca-Acetate (Ex. 6) | 5% IPA, 85 mM $CaCl_2$ (Ex. 7) | 10% EtOH, 10% PEG-6000 (Ex. 8) |
|---|---|---|---|
| 0 | 0.00 | 0.00 | 0.00 |
| 15 | 19.39 | 70.16 | 76.12 |
| 30 | 53.88 | 82.84 | 86.50 |
| 45 | 74.59 | 92.33 | 92.33 |
| 60 | 84.13 | 96.03 | 94.62 |
| 75 | 90.64 | 98.48 | 94.87 |
| 90 | 95.47 | 99.91 | 96.28 |
| 105 | 98.32 | 99.94 | 96.82 |
| 120 | 99.51 | 100.00 | 99.68 |
| 135 | 99.51 | 100.00 | 100.00 |
| 150 | 100.00 | 100.00 | 100.00 |
| 165 | 100.00 | 100.00 | 100.00 |
| 180 | 100.00 | 100.00 | 100.00 |

Example 10

Figure 10:
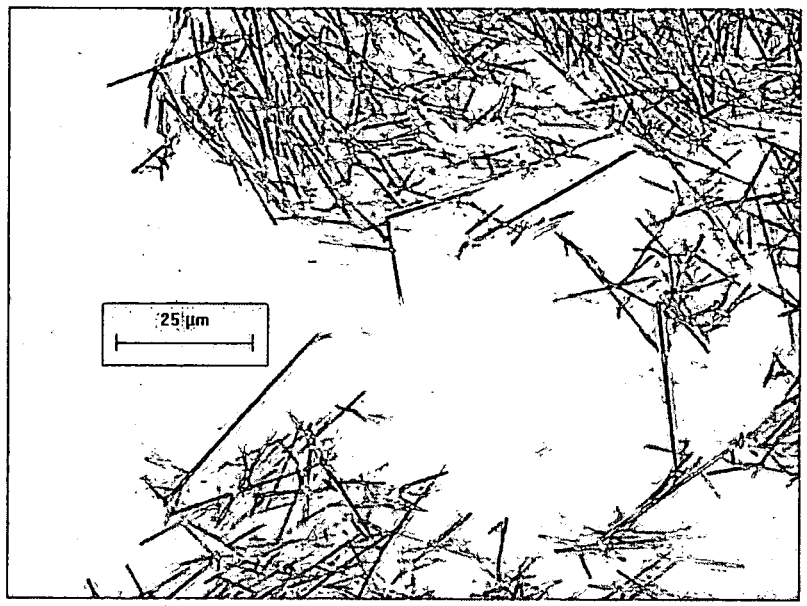
FIG. 10 illustrates hGH crystals grown in the presence of 85 mM calcium acetate, 2% (v/v) PEG-6000 and 100 mM Tris-HCl (pH 8.6), as imaged by optical microscopy. See Example 10.

Crystallization of hGH with calcium acetate and 2% PEG-6000. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. To this solution, 2% (v/v) PEG-6000 was added. Crystals of hGH were grown by adding Ca-Acetate (1 m) to the solution so that a final concentration of 85 mM Ca-Acetate was obtained. The solution was then incubated for 16 hours at 25° C. Needle-like crystals were obtained and image by optical microscopy. The crystals obtained were found to be between about 25 and about 75 µm in length with a crystallization yield of greater than 85%. See FIG. 10.

Example 11

Figure 11:
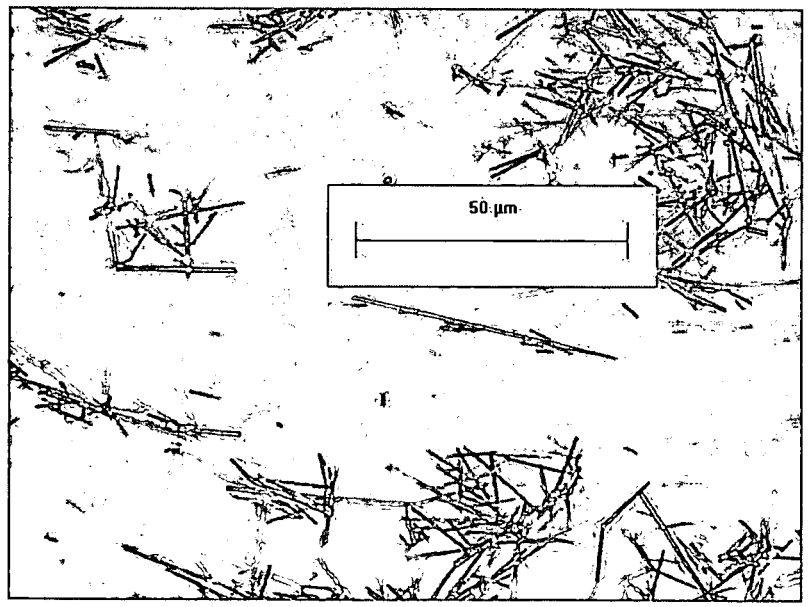
FIG. 11 illustrates hGH crystals grown in the presence of 500 mM sodium acetate, 6% (v/v) PEG-6000 and 100 mM Tris-HCl (pH 8.6), as imaged by optical microscopy. See Example 11.

Crystallization of hGH with sodium acetate and 6% PEG-6000. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. To this solution, 6% (v/v) PEG-6000 was added. Crystals of hGH were grown by adding sodium acetate (Na-Acetate) (2 M) to the solution so that a final concentration of 500 mM Na-Acetate was obtained. The solution was then incubated for 16 hours at 25° C. Needle-like crystals were obtained and imaged by optical microscopy. The crystals obtained were found to be between about 25 and about 75 µm in length with a crystallization yield of greater than 85%. See FIG. 11.

Example 12

Figure 12:
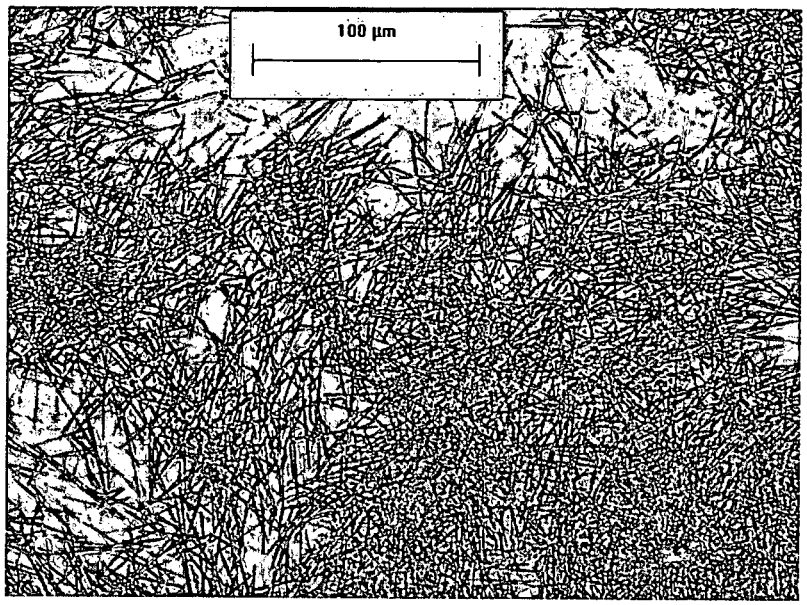
FIG. 12 illustrates hGH crystals grown in the presence of 85 mM calcium chloride, 6% (v/v) PEG-6000 and 100 mM Tris-HCl (pH 8.6) as imaged by optical microscopy. See Example 12.

Crystallization of hGH with calcium chloride and 6% PEG-6000. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. To this solution, 6% (v/v) PEG-6000 was added. Crystals of hGH were grown by adding $CaCl_2$ (1 M) to the solution, so that a final concentration of 85 mM $CaCl_2$ was obtained. The solution was then incubated for 16 hours at 25° C. Needle-like crystals were obtained and imaged by optical microscopy. The crystals obtained were found to be between greater than 100 µm in length with a crystallization yield of greater than 90%. See FIG. 12.

Example 13

Figure 13:
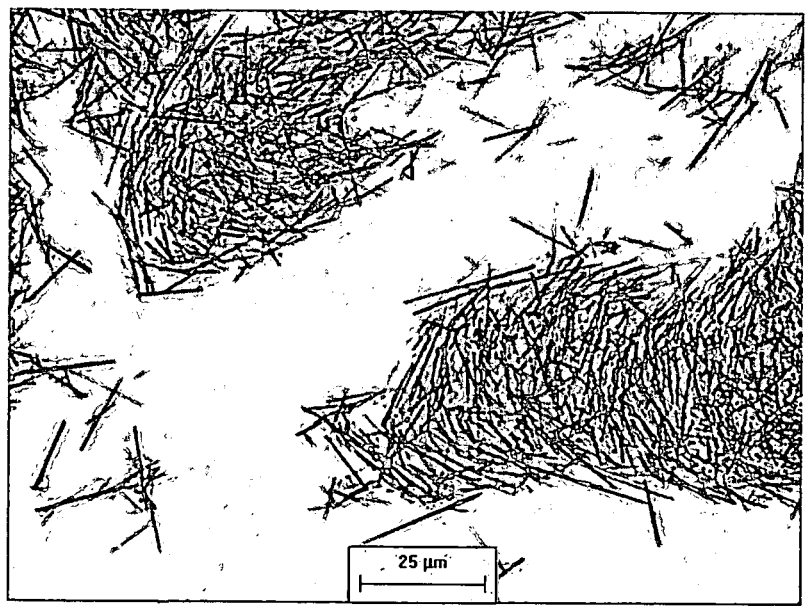
FIG. 13 illustrates hGH crystals grown in the presence of 85 mM calcium acetate, 6% (v/v) PEG-6000, 100 mM Tris-HCl (pH 8.6) and co-crystallized with Protamine sulfate (1 mg/ml) as imaged by optical microscopy. See Example 13.

Crystallization of hGH with calcium acetate, 6% PEG-6000 and protamine sulfate. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. To this solution, protamine sulfate (1 mg/ml) and 6% PEG-6000 (v/v) was added. Crystals of hGH were grown by adding Ca-Acetate (1 M) to the solution so that a final concentration of 85 mM Ca-Acetate was obtained. The solution was then incubated for 16 hours at 37° C. Needle-like crystals were obtained and imaged by optical microscopy. The crystals obtained were found to be less than 25 μm in length with a crystallization yield of greater than 70%. See FIG. 13.

Example 14

Figure 14:
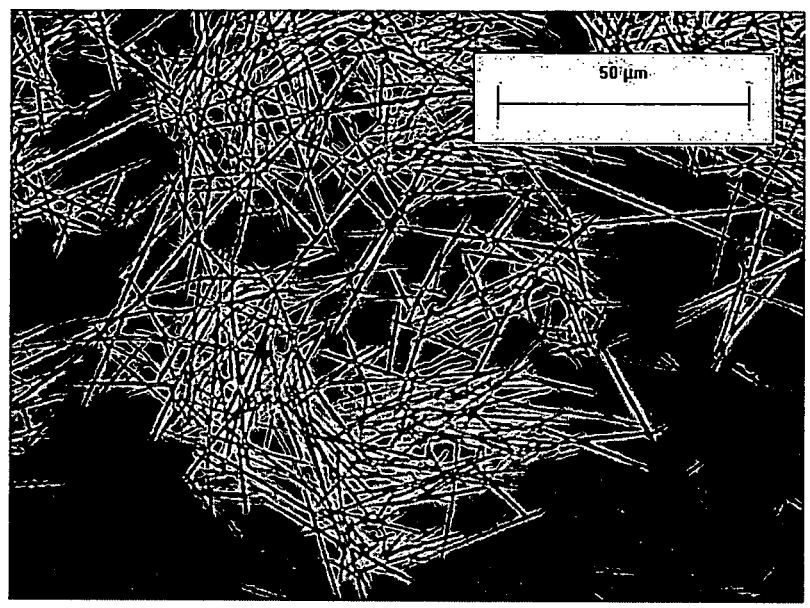
FIG. 14 illustrates hGH crystals grown in the presence of 125 mM calcium acetate, 6% (v/v) PEG-MME-6000 and 100 mM Tris-HCl (pH 8.6), as imaged by optical microscopy. See Example 14.

Crystallization of hGH with calcium acetate and 6% PEG-MME-5000. Commercially available hGH was purified and concentrated as described in Example 1. Deionized water was added to the concentrated hGH solution to yield a final protein concentration of 15 mg/ml. Tris-HCl (1 M, pH 8.6) was added to a final concentration of 100 mM. To this solution, 6% (v/v) polyethylene glycol mono methyl ether-5000 (PEG-MME-5000) was added. Crystals of hGH were grown by adding Ca-Acetate (1 M) to the solution so that a final concentration of 125 mM Ca-Acetate was obtained. The solution was then incubated for 16 hours at 25° C. Needle-like crystals were obtained and imaged by optical microscopy. The crystals obtained were found to be less than 50 μm in length with a crystallization yield of greater than 90%. See FIG. 14.

Example 15

Solubility profile of hGH crystals prepared with polyethylene glycol. After the incubation of the crystallization solutions prepared in Examples 10-14, the crystals were pelleted and the remaining supernatant removed. The crystal pellets were resuspended in 0.2 ml of dissolution buffer (see Example 5) by either pipetting or vortexing before being equilibrated for approximately 15 minutes at 37° C. The samples were then centrifuged at 10,000×g for 2 minutes and the supernatant was removed for determination of protein concentration measured at 280 nm by RP-HPLC, SEC-HPLC or UV-VIS. The crystalline pellets were further resuspended in dissolution buffer and the process repeated until no detectable protein was measured in the supernatant.

Figure 15:
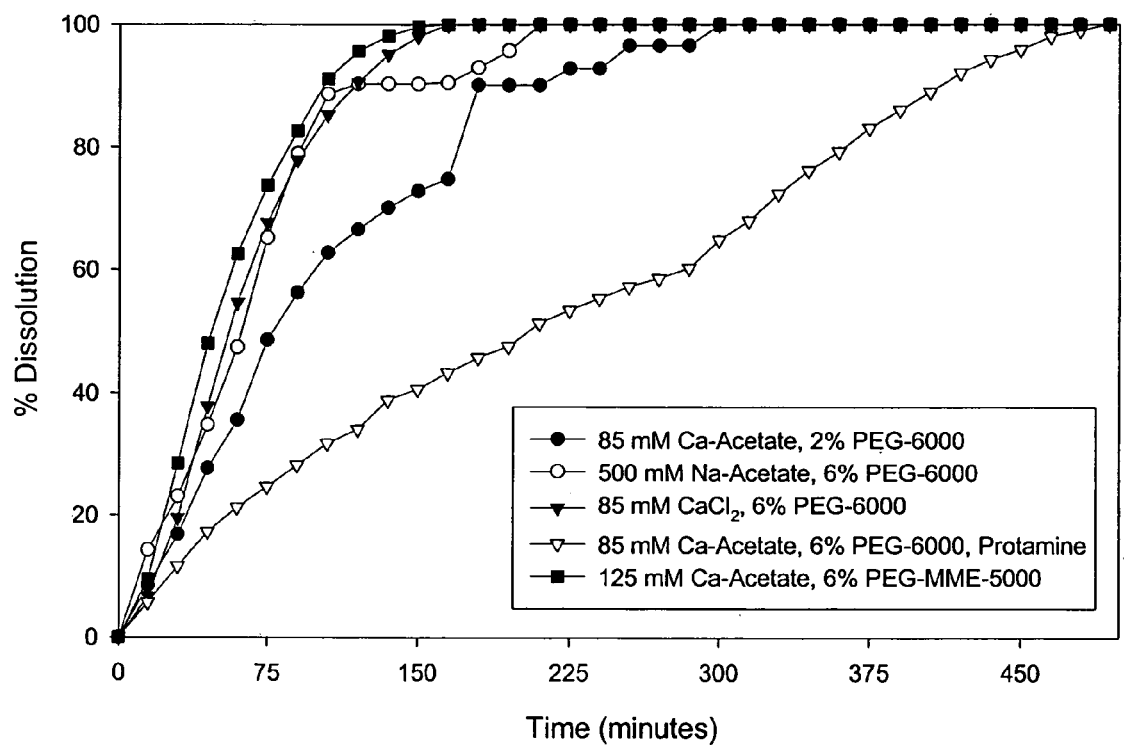
FIG. 15 shows solubility of hGH crystals grown according to Examples 10-14, monitored at 280 nm as a function of time in minutes. See Example 15.

FIG. 15 and Table 3 illustrate the solubility behavior of hGH crystals prepared with 2% PEG-6000/85 mM Ca-Acetate, 6% PEG-6000/500 mM Na-Acetate, 6% PEG-6000/85 mM $CaCl_2$, 6% PEG-6000/85 mM Ca-Acetate/protamine and 6% PEG-MME-5000/125 mM Ca-Acetate as a function of time in minutes. hGH dissolution was measured as a cumulative percentage and derived from AUC values or UV-VIS mg/ml measurements. The results demonstrate that the hGH crystals prepared by the addition of 6% PEG-6000/85 mM Ca-Acetate/Protamine were the slowest to dissolve, with complete dissolution occurring after 495 minutes. The other crystals dissolved at 300 minutes for 2% PEG-6000/85 mM Ca-Acetate crystals or less for the other hGH crystals.

TABLE 3

Sequential dissolution test measured at 280 nm for PEG and salts of hGH in dissolution buffer - protein concentration was expressed as percent of total released

| Time (minutes) | 2% PEG-6000/85 mM Ca-Acetate (Ex. 10) | 6% PEG-6000/500 mM Na-Acetate (Ex. 11) | 6% PEG-6000/85 mM Ca-Chloride (Ex. 12) | 6% PEG-6000/85 mM Ca-Acetate/Protamine sulfate (Ex. 13) | 6% PEG-MME-5000/125 mM Ca-Acetate (Ex. 14) |
|---|---|---|---|---|---|
| 0 | 0.00 | 0.00 | 0.00 | 0.00 | 0.00 |
| 15 | 8.41 | 14.23 | 6.63 | 5.66 | 9.50 |
| 30 | 16.80 | 23.03 | 19.50 | 11.58 | 28.46 |
| 45 | 27.64 | 34.74 | 37.74 | 17.22 | 48.04 |
| 60 | 35.57 | 47.34 | 54.60 | 21.25 | 62.61 |
| 75 | 48.57 | 65.16 | 67.67 | 24.63 | 73.76 |
| 90 | 56.18 | 78.86 | 77.90 | 28.15 | 82.70 |
| 105 | 62.70 | 88.66 | 85.26 | 31.77 | 91.15 |
| 120 | 66.49 | 90.36 | 90.59 | 34.05 | 95.70 |
| 135 | 70.07 | 90.36 | 95.18 | 38.83 | 98.18 |
| 150 | 72.87 | 90.36 | 98.04 | 40.60 | 99.60 |
| 165 | 74.82 | 90.58 | 100.00 | 43.28 | 100.00 |
| 180 | 90.23 | 93.06 | 100.00 | 45.69 | 100.00 |
| 195 | 90.23 | 95.80 | 100.00 | 47.52 | 100.00 |
| 210 | 90.23 | 100.00 | 100.00 | 51.27 | 100.00 |
| 225 | 92.90 | 100.00 | 100.00 | 53.38 | 100.00 |
| 240 | 92.90 | 100.00 | 100.00 | 55.31 | 100.00 |
| 255 | 96.61 | 100.00 | 100.00 | 57.24 | 100.00 |
| 270 | 96.61 | 100.00 | 100.00 | 58.61 | 100.00 |
| 285 | 96.61 | 100.00 | 100.00 | 60.28 | 100.00 |
| 300 | 100.00 | 100.00 | 100.00 | 64.90 | 100.00 |
| 315 | 100.00 | 100.00 | 100.00 | 68.04 | 100.00 |
| 330 | 100.00 | 100.00 | 100.00 | 72.46 | 100.00 |
| 345 | 100.00 | 100.00 | 100.00 | 76.26 | 100.00 |
| 360 | 100.00 | 100.00 | 100.00 | 79.36 | 100.00 |
| 375 | 100.00 | 100.00 | 100.00 | 83.20 | 100.00 |
| 390 | 100.00 | 100.00 | 100.00 | 86.17 | 100.00 |
| 405 | 100.00 | 100.00 | 100.00 | 89.15 | 100.00 |
| 420 | 100.00 | 100.00 | 100.00 | 92.25 | 100.00 |

TABLE 3-continued

Sequential dissolution test measured at 280 nm for PEG and salts of hGH in dissolution buffer - protein concentration was expressed as percent of total released

| Time (minutes) | 2% PEG-6000/85 mM Ca-Acetate (Ex. 10) | 6% PEG-6000/500 mM Na-Acetate (Ex. 11) | 6% PEG-6000/85 mM Ca-Chloride (Ex. 12) | 6% PEG-6000/85 mM Ca-Acetate/ Protamine sulfate (Ex. 13) | 6% PEG-MME-5000/125 mM Ca-Acetate (Ex. 14) |
|---|---|---|---|---|---|
| 435 | 100.00 | 100.00 | 100.00 | 94.40 | 100.00 |
| 450 | 100.00 | 100.00 | 100.00 | 95.96 | 100.00 |
| 465 | 100.00 | 100.00 | 100.00 | 98.07 | 100.00 |
| 480 | 100.00 | 100.00 | 100.00 | 99.07 | 100.00 |
| 495 | 100.00 | 100.00 | 100.00 | 100.00 | 100.00 |

Example 16

Pharmacokinetic study using Sprague-Dawley rats. A 2.5 mg/kg dose of soluble (commercially available) or crystalline (85 mM Ca-Acetate/2% PEG-6000) hGH, prepared as set forth in Example 10, suspension was administered subcutaneously into 24 female Sprague-Dawley rats. The average weight-of-each rat was 200 grams. The 24 rats were separated into two groups. Each group included a subset of 3 groups, each containing 4 rats. Bleedings were collected via a jugular vein duct implant at three specified time points within each subset. Due to the limited amount of blood able to be drawn at a given time point, a leap frog design was used. In order to maintain animal stability, subsets of animals within groups were bled at noted time points. Serum samples were then compiled to form a linear progressive timeline. Standard deviations were determined by the variance of serum levels within subsets at a given time point from the mean of that subset. See Tables 4-6. In Tables 4-5, animals designated 1-12 received soluble hGH and animals 13-24 received crystallized hGH at a dose of 500 μg each animal.

Figure 16:
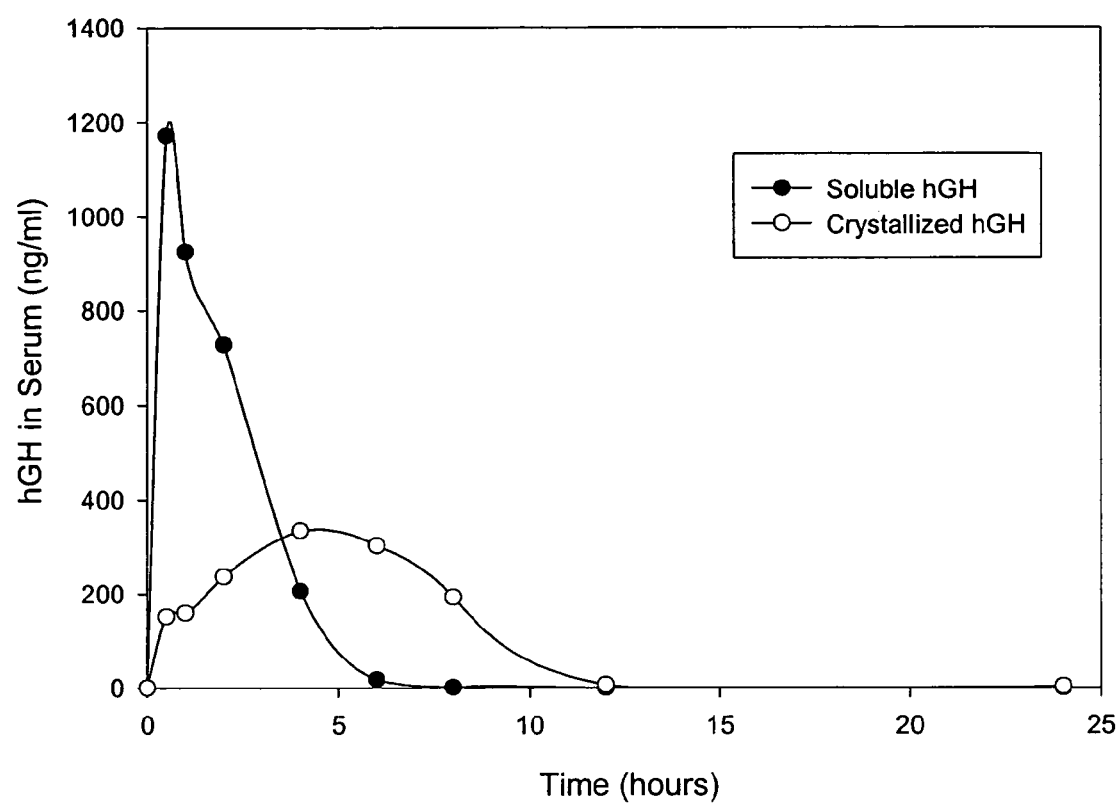
FIG. 16 shows serum levels (ng/ml) of commercial hGH (hGH soluble) and hGH prepared according to Example 10 (hGH crystalline) in female Sprague-Dawley rats sampled over 24 hours after a single subcutaneous administration of 2.5 mg/kg dose of soluble or crystalline hGH per rat. Serum levels were measured at t=0, 0.5, 1, 2, 4, 6, 8, 12 and 24 hours. See Example 16.

FIG. 16 illustrates the level of hGH in serum as a function of time for the soluble and crystallized hGH. The half-life of the crystallized hGH was almost 19 fold higher than that of soluble hGH. The time at which maximum hGH appeared in the serum was 4 hours for the crystallized hGH and 0.5 hours for the soluble hGH. Given that groups and subsets of rats were treated with soluble hGH or crystal hGH at a concentration of 5.5 mg/ml, dose equal to 2.2 mg/kg, the $C_{max}$ values, listed below in Table 6, show that hGH when delivered in crystalline form significantly reduced the maximum serum concentration compared to an identical soluble dose. Also, the AUC of total serum level for hGH soluble versus hGH crystal was similar, indicating that bioavailability was not significantly affected by crystallization. A $T_{90\%}$ value was calculated for both the soluble and crystalline results. This parameter indicates the time at which 90% of the total AUC has occurred. Higher values of $T_{90\%}$ indicate that the drug remains in the serum for longer. The $T_{90\%}$ results contained in Table 6 clearly show that the crystalline form results in elevated hGH levels for significantly longer than the soluble form.

TABLE 4 hGH animal pharmacokinetic study results for soluble hGH

| Animals | Bleed Time (hr) | Average hGH in serum (ng/ml) | Standard Deviation |
|---|---|---|---|
| 1–4 | 0 | 0.00 | 0.00 |
| 5–8 | 0.5 | 1171.65 | 116.03 |
| 9–12 | 1 | 924.49 | 67.90 |
| 1–4 | 2 | 726.84 | 163.83 |
| 5–8 | 4 | 205.90 | 29.40 |
| 9–12 | 6 | 17.48 | 6.66 |
| 1–4 | 8 | 1.14 | 1.68 |
| 5–8 | 12 | 0.00 | 0.00 |
| 9–12 | 24 | 0.00 | 0.00 |
| | Total = | 3047.50 | |

TABLE 5 hGH animal pharmacokinetic study results for crystallized hGH (85 mM Ca-Acetate/2% PEG-6000)

| Animals | Time (hr) | Average hGH in serum (ng/ml) | Standard Deviation |
|---|---|---|---|
| 13–16 | 0 | 0.00 | 0.00 |
| 17–20 | 0.5 | 151.39 | 60.30 |
| 21–24 | 1 | 159.19 | 69.50 |
| 13–16 | 2 | 236.64 | 75.70 |
| 17–20 | 4 | 334.08 | 63.86 |
| 21–24 | 6 | 302.69 | 73.09 |
| 13–16 | 8 | 193.22 | 23.10 |
| 17–20 | 12 | 6.50 | 6.39 |
| 21–24 | 24 | 2.69 | 0.74 |
| | Total = | 1386.379 | |

TABLE 6

Pharmacokinetic parameters based on data in Tables 4 and 5

| | Soluble | Crystallized |
|---|---|---|
| Dose Amount (μg) | 500 | 500 |
| Dosage (mg/kg) | 2.5 | 2.5 |
| Half life (hr) | 0.5 | 9.4 |
| $C_{max}$ (ng/ml) | 1172 | 334 |
| $T_{max}$ (hr) | 0.5 | 4 |

TABLE 6-continued

Pharmacokinetic parameters based on data in Tables 4 and 5

|  | Soluble | Crystallized |
|---|---|---|
| AUC (0-t) (ng/hr/ml) | 2819 | 2472 |
| AUC (2) | 2819 | 2508 |
| $T_{90\%}$ (hr) | 4 | 10 |

Example 17

Figure 17:
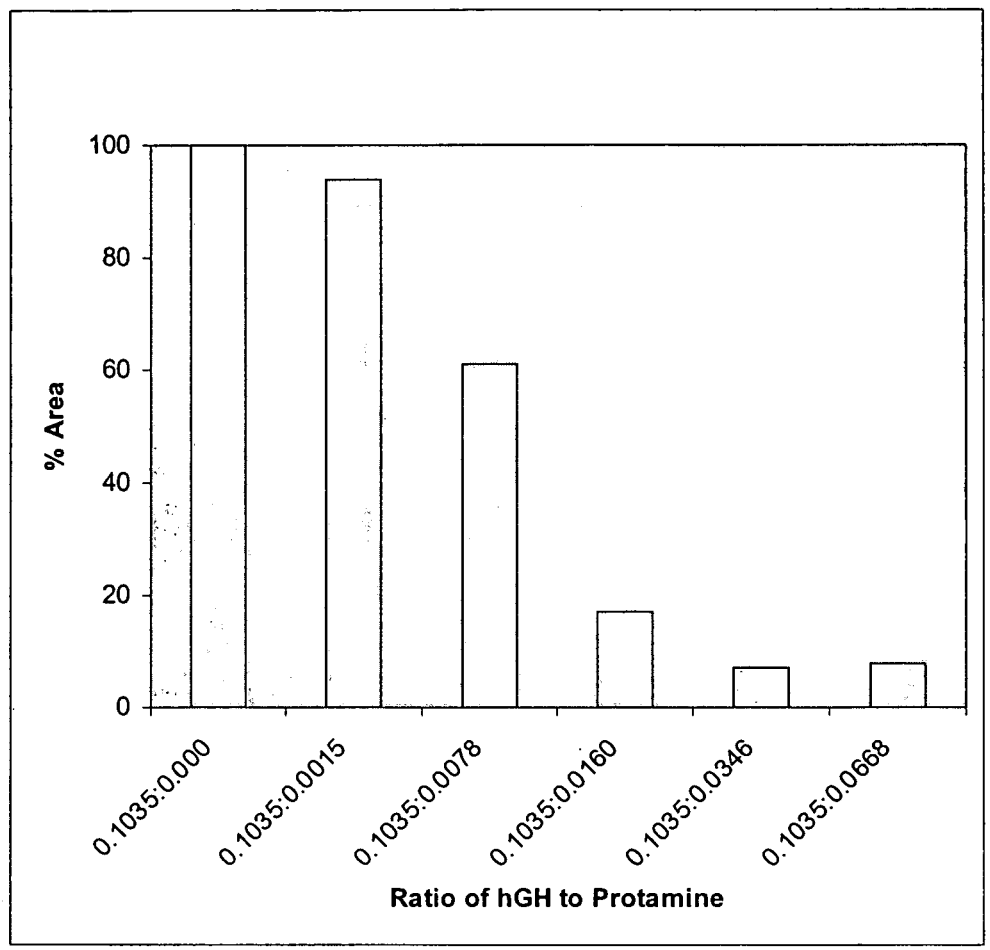
FIG. 17 illustrates the dissolution characteristics of hGH crystals (formed in the presence of 85 mM calcium acetate, 2% (v/v) PEG-6000 and 100 mM Tris-HCl (pH 8.6)) upon the addition of varying amounts of Protamine sulfate. These various formulations of hGH crystals were then added to dissolution buffer and allowed to sit for 1 hour before the concentration of soluble hGH in the supernatant was measured by RP-HPLC (Area). See Example 17.

Effect of Protamine sulfate on dissolution characteristics of hGH crystals. FIG. 17 illustrates the amount of hGH crystals prepared according to Example 10 (85 mM calcium acetate, 2% (v/v) PEG-6000 and 100 mM Tris-HCl (pH 8.6)) dissolved after 1 hour incubation in dissolution buffer at 37° C. after adding a given amount of protamine sulfate to the pre-existing calcium hGH crystal solution. The ratios of hGH to protamine (mg:mg) ratios are indicated in FIG. 17. The graph illustrates that protamine significantly affects dissolution of hGH crystals.

Example 18

Figure 18A:
FIG. 18A illustrates hGH crystals grown in the presence of 500 mM sodium acetate, 6% v/v PEG-6000 and 100 mM Tris-HCl (pH 8.6), as imaged lengthwise by TEM. See Example 18.
Figure 18B:
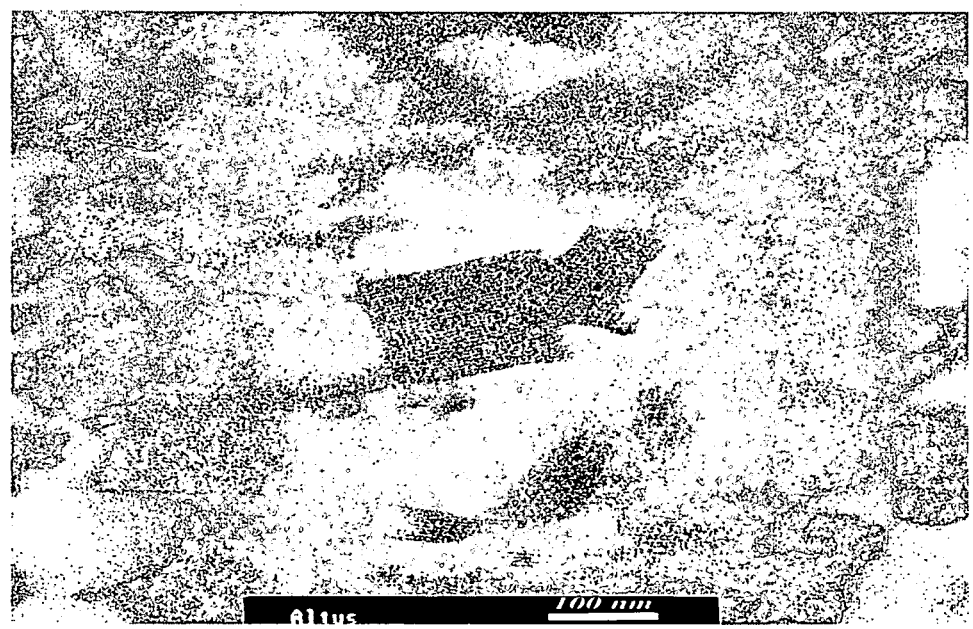
FIG. 18B illustrates hGH crystals grown in the presence of 500 mM sodium acetate, 6% v/v PEG-6000 and 100 mM Tris-HCl (pH 8.6), as imaged cross-sectionally by TEM. See Example 18.

Crystallization of hGH with sodium acetate. Here, a frozen bulk feed solution of soluble recombinantly-produced hGH (rhGH) was obtained from two stocks—one derived from *E. coli* (Novartis) and the other from yeast (Lucky Gold). Separate analyses of rhGH derived from *E. coli* and yeast stock solutions resulted in rhGH having the same crystallization and solubility characteristics irrespective of its source. Approximately 3.3 ml (10-20 mg/ml rhGH as supplied in unknown buffer) of thawed rhGH feed solution was purified using a 10DG-desalting column supplied by BioRad. Prior to sample loading, the column was conditioned by washing the column with 30 ml of Tris-HCl (10 mM, pH 8.0). The rhGH sample was then loaded and allowed to enter the column by gravity. After discarding the first three ml of eluant, another 5.0 ml of 10 mM Tris-HCl pH 8.0 was then added. 4.5 ml of the desalted rhGH was eluted and collected. Concentration by centrifugation was then performed using a Millipore concentrator (MWCO 10,000) at 3500 rpm for 20-30 min. The concentration of hGH was in range of 30 mg/ml, as measured by absorbance at 280 nm/0.813 (1 mg/ml hGH A280=0.813 absorbance units). Crystals were grown by adding deionized water, Tris-HCl (pH 8.6), PEG-6000 and Na-acetate to final concentrations of 100 mM, 6% (v/v) and 500 mM, respectively in the total solution with a final protein concentration of 15 mg/ml. The solution was then mixed gently and incubated at 33° C. for 12-16 hours. Needle- or rod-like crystals were obtained and imaged with TEM (FIGS. 18A and 18B). The crystals ranged in length from approximately 2 to 25 μm. After centrifuging and pelleting the crystals the supernatant was extracted and, crystallization yield was measured as greater than 85%. The crystals can also be formed at temperatures between 33° C. and 15° C. but require increased crystallization time and possibly result in reduced yield.

Example 19

Complexation of sodium hGH crystals with ionic polymer additive. After crystallization yield was determined (see Example 18), sodium rhGH crystals were re-suspended in mother liquor (250 mM NaOAc, 25 mM Tris-HCl (pH 8.6), 6% PEG-6000, and either 7 mg/ml protamine sulfate or 4.2 mg/ml polyarginine) so that a final concentration of 21 mg/ml of sodium rhGH crystals was achieved. The protein to additive ratio for rhGH to protamine sulfate was approximately 3:1 (mg:mg) and for rhGH to polyarginine was 5:1 (mg:mg). These ratios are calculated to be mole ratios of approximately 1:1.715 for rhGH:protamine and approximately 1:0.587 for rhGH:polyarginine. The above rhGH pellets were homogenously re-suspended in the appropriate mother liquor and incubated overnight at 2-8° C. before being centrifuged to obtain a condensed pellet. The supernatants were removed and the pellets were re-suspended in the same mother liquor (without ionic polymer additive) and stored at 4° C.

Additional rhGH:ionic polymer additive ratios may be obtained by varying the additive concentration (mg/ml) of the mother liquor while still resuspending to 21 mg/ml of rhGH. For example, increased concentrations of protamine sulfate (10.5 mg/ml) in the mother liquor can be used to obtain a ratio upon resuspension of rhGH:additive of 2:1.

Example 20

Crystallization of hGH with zinc acetate. Crystallization of rhGH with Zinc-acetate and acetone. Approximately 3.3 ml (10-20 mg/ml) of thawed rhGH feed solution was purified using a 10DG-desalting column supplied by BioRad. Prior to sample loading, the column was conditioned by washing with 30 ml of $Na_2HPO_4/NaH_2PO_4$ (10 mM, pH 6.1). The rhGH sample was then loaded and allowed to enter the column by gravity. After discarding the first three ml of eluant, another 5.0 ml of 10 mM $Na_2HPO_4/NaH_2PO_4$ pH 6.1 was added. A 4.5 ml aliquot of the desalted rhGH was eluted and collected. Concentration by centrifugation was then performed using a Millipore concentrator (MWCO 10,000) at 3500 rpm for 5-10 min. The concentration of hGH was in range of 15 mg/ml as measured by absorbance at 280 nm/0.813 (1 mg/ml hGH A280=0.813 absorbance units). Crystals were grown by adding 400 Ml of mother liquor containing deionized water, 8.91 mM $Na_2HPO_4/NaH_2PO_4$ pH 6.1, 0.88 mg/ml Zinc-acetate, 9.89% Acetone, to 100 μl of prepared 15 mg/ml protein in 10 mM $Na_2HPO_4/NaH_2PO_4$ (pH 6.1). The solution was then mixed gently and incubated at 15° C. for 24-48 hours. Hexagon-like crystals were obtained ranging in width from approximately 2 to 25 μm. After centrifuging and pelleting the crystals the supernatant was extracted and, crystallization yield was measured as roughly 55%.

Example 21

Crystallization of hGH with calcium acetate and complexation of calcium hGH with ionic polymer additive (polyarginine). Here, a frozen bulk feed solution of soluble recombinantly-produced hGH (rhGH) was obtained from two stocks—one derived from *E. coli* (Novartis) and the other from yeast (Lucky Gold). Approximately 3.5 ml (12 mg/ml rhGH in Tris-HCl (10 mM, pH 8.0)) of thawed rhGH feed solution was purified using a 10DG-desalting column supplied by Biorad. Prior to sample loading, the column was conditioned by washing the column with 30 ml of Tris-HCl (10 mM, pH 8.0). The rhGH sample was then loaded and allowed to enter the column by gravity. After discarding the first three ml of eluant, another 5.0 ml of 10 mM Tris-HCl pH 8.0 was then added. 4.5 ml of the desalted rhGH was eluted and collected. Concentration by centrifugation was then performed using a Millipore concentrator (MWCO 10,000) at 3500 rpm for 20-30 min. The concentration of hGH was in the range of 30 mg/ml as measured by absorbance at 280 nm/0.813(1 mg/ml hGH A280=0.813 absorbance units). Crystals were grown by adding 1M Tris-HCl (pH 8.6), 50% PEG-6000 and 1M Ca-acetate to the rhGH 30 mg/ml stock preparation so that a final concentration of 15 mg/ml rhGH, 100 mM Tris-HCl (pH 8.6), 2% (v/v) PEG-6000 and 85 mM Ca-acetate was obtained. The solution was then mixed gently and incubated at 33° C. for 12-16 hours. Needle-like-crystals were obtained ranging in length from approximately 2 to 25

μm. After extracting the supernatant and centrifuging and pelleting the crystals, crystallization yield was measured as greater than 85%. The crystals could also be formed at temperatures between 33° C. and 15° C. but required increased crystallization time and reduced yield. After crystallization yield was determined (see Example 18), calcium rhGH crystals were re-suspended in formulation vehicle (5 mM CaOAc, 100 mM Tris-HCl (pH 8.6), 6% PEG-6000, and 4.2 mg/ml polyarginine) so that a final concentration of 21 mg/ml of calcium rhGH crystals was achieved. The protein to additive ratio for rhGH to polyarginine was 5:1 (mg:mg). These ratios are calculated to be mole ratios of approximately 1:0.587 for rhGH:polyarginine. The above rhGH pellets were homogenously re-suspended in the appropriate mother liquor and incubated overnight at 2-8° C. before being centrifuged to obtain a condensed pellet. The supernatants were removed and the pellets were re-suspended in the same mother liquor without ionic additive and stored at 4° C.

Example 22

Pharmacokinetic and pharmacodynamic study of subcutaneously administered hGH using Sprague-Dawley rats and divalent cation crystals of hGH. The goal of this study was to assess the controlled release of hGH from hGH crystal suspensions and the weight gained upon subcutaneous implantation of hGH crystal suspensions in hypophysectomized Sprague-Dawley rats. The study design was as follows:

TABLE 7

Study Design

| Group # or Test Compound | Sample[a] | Sample Description | # of Rats | Dose Level (mg/rat/week) | Dose Regimen |
|---|---|---|---|---|---|
| 1 | Soluble Vehicle | Buffer in Water for Injection (WFI)[b] | 3 | — | 100 μl once daily over 7 days |
| 2 | Daily Soluble | Commercially available hGH[c] in WFI (1.5 mg/ml) | 9 | 1.05 | 100 μl once daily over 7 days |
| 3 | Ca-Acetate, PEG | See Example 10 - (21 mg/ml, dilution and gentle mixing with Mother Liquor 1[d] 1:1 prior to injection | 9 | 1.05 | 100 μl once on day 1 |
| 4 | Ca-Acetate, PEG, Protamine | See Example 13 (21 mg/ml, dilution and gentle mixing with Mother Liquor 1[d] 1:1 prior to injection, ratio of rhGH:protamine = 5:1) | 9 | 1.05 | 100 μl once on day 1 |
| 5 | Zn-Acetate | See Example 20 (21 mg/ml, dilution and gentle mixing Mother Liquor 2[e] 1:1 prior to injection) | 3 | 1.05 | 100 μl once on day 1 |
| 7 | Vehicle | Mother Liquors from Groups 3, 4, & 5[f] | 3 | — | 100 μl once on day 1 |
| 8 | Vehicle | Mother Liquor from Group 9 | 3 | — | 100 μl once on day 1 |
| 9 | Ca-Acetate, PEG, Polyarginine | See Example 21 (21 mg/ml, dilution and gentle mixing with Mother Liquor 1[d] 1:1 prior to injection, ratio of rhGH:polyarginine = 12:1) | 9 | 1.05 | 100 μl once on day 1 |

[a]All samples were stored at 4° C. and warmed to room temperature for 30 minutes prior to dilution with formulation vehicle defined in d, if required, and injection into the indicated number of rats.
[b]Buffer comprises 7.5 mg/ml D-mannitol, 12 mg/ml sucrose.
[c]Commercially-available hGH obtained from BesaGen Ltd., Australia.
[d]5 mM CaOAc, 4% PEG-6000, 0.025 M glycine (pH 8.6), 15 mg/ml D-mannitol, 60 mg/ml sucrose.
[e]Zinc-acetate, NaH$_2$PO$_4$ (pH 6.1), Ethanol.
[f]A single formulation vehicle defined in d was used as a vehicle control for all of these groups.

Upon arrival, 80 female Sprague-Dawley rats, weighing approximately 150 grams±25 g and being approximately 4-6 weeks old, were individually housed under controlled conditions (approximate temperature 21±3° C., relative humidity 50±20%, 12 hours light and 12 hours darkness in each 24-hour period, 10-15 air changes per hour) and given access to purified water and laboratory chow ad libitum throughout the study. The rats were allowed to acclimate to the environment for one week prior to testing.

Out of the 80 rats, 48 were administered hGH suspensions according to Table 7. The test compounds were administered once on day one or once daily for seven consecutive days as a single bolus injection subcutaneously in the dorsum area. The site of injection was shaved and marked up to 3 days prior to dosing and thereafter as required to facilitate injection. The test compounds were administered using a 30-gauge×8 mm needle attached to a 300 µl syringe. Test compounds were carefully inverted in order to ensure suspension or solution uniformity without causing foaming prior to withdrawal into the syringe and again prior to administration. The injection volume was approximately 0.1 ml per rat.

Blood samples from rats in groups 1, 5, 7 and 8 (each having 3 rats per group) were collected at 4, 32, 96 and 168 hours following injection on Day 1. Blood samples from rats in groups 2, 3, 4 and 9 (each having 9 rats per group) were further subdivided into 3 groups of 3 rats. Here, blood samples were collected from the first subset of rats at 0.5, 24, 72, and 168 hours, from the second subset at 4, 32, 96 and 168 hours and from the third subset at 8, 48, 120 and 168 hours following injection on Day 1. Bleedings were typically collected on unanesthetized or $CO_2/O_2$ anesthetized rats through the orbital sinus and collected in BD Microtainer tubes with serum separators. Samples were then centrifuged at approximately 4° C. and serum recovered and stored frozen (approx. −80° C.) prior to determination of hGH and IGF-1 levels.

Figure 19A:
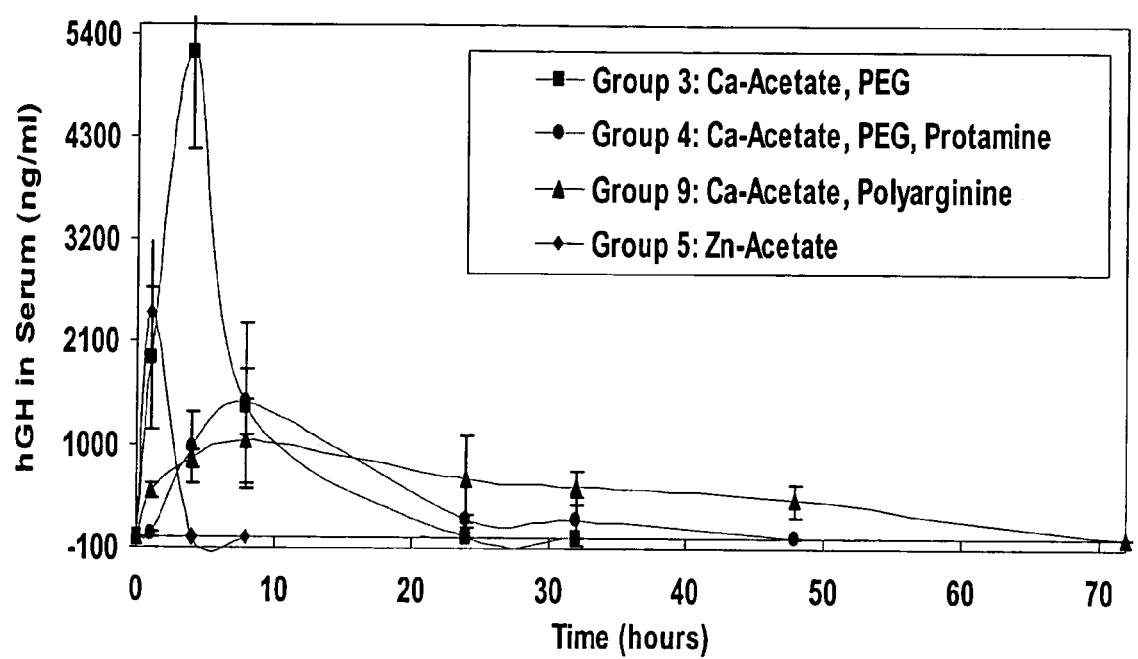
FIG. 19A shows serum levels (ng/ml) of hGH in Groups 3-5 and 9 of female Sprague-Dawley rats sampled over 168 hours (0-72 hours shown) after either daily subcutaneous administration over 7 days or a single subcutaneous administration over 7 days of 6.7 mg/kg dose of hGH per rat. See Example 22 and Tables 7-12.

Serum samples were then compiled and in the case of groups 2, 3, 4 and 9, a linear progressive timeline was formed. Standard deviations were determined by the variance of serum levels within subsets at a given time point from the mean of that subset. See Tables 8-14 and FIG. 19A. Serum levels (ng/ml) of rhGH are shown when administered in a particular crystalline formulation. Animals were bled according to the study protocol at specific time points relative to dosing. The results clearly indicate that a difference exists between the absorption of complexed crystalline material (e.g., protamine and poly-arginine) and non-complexed crystalline formulations (e.g., CaOAC and ZnOAC).

TABLE 8 hGH animal pharmacokinetic study results for Group 2: Daily Soluble

| Animals | Bleed Time (hr) | Average hGH in serum (ng/ml) | Standard Deviation |
|---|---|---|---|
| All | 0 | 0 | 0 |
| 1–3 | 1 | 1262 | 18 |
| 4–6 | 4 | 234 | 45 |
| 7–9 | 8 | 2 | 2 |
| 1–3 | 24 | 1218 | 258 |
| 4–6 | 32 | 3 | 1 |
| 7–9 | 48 | 0 | 0 |
| 1–3 | 72 | 1098 | 40 |
| 4–6 | 96 | 0 | 0 |
| 7–9 | 120 | 1355 | 337 |
| All | 168 | 0 | 0 |
| Total = | | 5174 | |

TABLE 9 hGH animal pharmacokinetic study results for Group 3: Ca-Acetate, PEG

| Animals | Bleed Time (hr) | Average hGH in serum (ng/ml) | Standard Deviation |
|---|---|---|---|
| All | 0 | 0.00 | 0.00 |
| 1–3 | 0.5 | 1927 | 771 |
| 4–6 | 4 | 5204 | 1040 |
| 7–9 | 8 | 1409 | 881 |
| 1–3 | 24 | 1 | 0.49 |
| 4–6 | 32 | 0.00 | 0.00 |
| 7–9 | 48 | 0.00 | 0.00 |
| 1–3 | 72 | 0.00 | 0.00 |
| 4–6 | 96 | 0.00 | 0.00 |
| 7–9 | 120 | 0.00 | 0.00 |
| All | 168 | 0.00 | 0.00 |
| Total = | | 8542 | |

TABLE 10 hGH animal pharmacokinetic study results for Group 4: Ca-Acetate, PEG, Protamine

| Animals | Bleed Time (hr) | Average hGH in serum (ng/ml) | Standard Deviation |
|---|---|---|---|
| All | 0 | 0.00 | 0.00 |
| 1–3 | 0.5 | 0.00 | 0.00 |
| 4–6 | 4 | 38 | 27 |
| 7–9 | 8 | 961 | 385 |
| 1–3 | 24 | 1468 | 357 |
| 4–6 | 32 | 192 | 73 |
| 7–9 | 48 | 190 | 266 |
| 1–3 | 72 | 0 | 0 |
| 4–6 | 96 | 0 | 0 |
| 7–9 | 120 | 0 | 0 |
| All | 168 | 0 | 0 |
| Total = | | 2849 | |

TABLE 11 hGH animal pharmacokinetic study results for Group 5: Zn-Acetate

| Animals | Bleed Time (hr) | Average hGH in serum (ng/ml) | Std Dev. |
|---|---|---|---|
| All | 0 | 0.00 | 0.00 |
| 1 | 4 | 2417 | 767 |
| 2 | 32 | 1 | 1 |
| 3 | 96 | 0 | 0 |
| All | 168 | 0 | 0 |
| | Total = | 2418 | |

TABLE 12 hGH animal pharmacokinetic study results for Group 9: Ca-Acetate, Polyarginine

| Animals | Bleed Time (hr) | Average hGH in serum (ng/ml) | Standard Deviation |
|---|---|---|---|
| All | 0 | 0.00 | 0.00 |
| 1–3 | 1 | 502 | 75 |
| 4–6 | 4 | 846 | 102 |
| 7–9 | 8 | 1036 | 448 |
| 1–3 | 24 | 634 | 462 |
| 4–6 | 32 | 543 | 168 |
| 7–9 | 48 | 407 | 169 |
| 1–3 | 72 | 9 | 0 |
| 4–6 | 96 | 0.00 | 0.00 |
| 7–9 | 120 | 0.00 | 0.00 |
| All | 168 | 0.00 | 0.00 |
| | Total = | 3980 | |

TABLE 13

Pharmacokinetic parameters based on data in Tables 8–12

| Groups | Dosage per 7 Days | $C_{max}$ (ng/ml) | $T_{max}$ (hr) |
|---|---|---|---|
| 2: Daily Soluble | 6.7 mg/kg | 1262.70 | 1 |
| 3: Ca-Acetate, PEG | 6.7 mg/kg | 5203.80 | 4 |
| 4: Ca-Acetate, PEG, Protamine | 6.7 mg/kg | 1468.47 | 8 |
| 5: Zn-Acetate | 6.7 mg/kg | 2416.97 | 4 |
| 9: Ca-Acetate, Polyarginine | 6.7 mg/kg | 1036.63 | 8 |

The weight of each rat was measured and recorded prior to injection Day 1 of the study and again on each subsequent morning of the study prior to bleed time. Accordingly, weight gain or loss of each rat within each group was calculated by subtracting the weight of Day 1 (prior to injection) from each subsequent day (prior to injection). Weight averages for all rats within a group were calculated for each day. These results are provided in Table 14.

TABLE 14

Weight gain or loss per day for Sprague-Dawley rats (grams)

| Group | Day 1 | Day 2 | Day 3 | Day 4 | Day 5 | Day 6 | Day 7 | Day 8 |
|---|---|---|---|---|---|---|---|---|
| 1 | 0 | −3.31 | 1.00 | −0.02 | −4.78 | −6.82 | −9.02 | −7.45 |
| 2 | 0 | 1.68 | 6.82 | 3.55 | 5.07 | 7.06 | 7.86 | 12.69 |
| 3 | 0 | 3.09 | 3.97 | 2.08 | 1.55 | 2.07 | 0.33 | 2.02 |
| 4 | 0 | 6.10 | 9.25 | 5.80 | 1.15 | 3.95 | 5.01 | 6.20 |
| 5 | 0 | −0.09 | 1.40 | −0.48 | 0.01 | −1.41 | −2.22 | −0.95 |
| 7 | 0 | −3.96 | 0.62 | 1.39 | 1.70 | 2.09 | 1.24 | 2.13 |
| 8 | 0 | −2.18 | −0.27 | −1.42 | 0.85 | −0.82 | −1.16 | 0.61 |
| 9 | 0 | 4.17 | 8.45 | 8.81 | 8.09 | 9.10 | 7.31 | 10.00 |

Figure 19B:
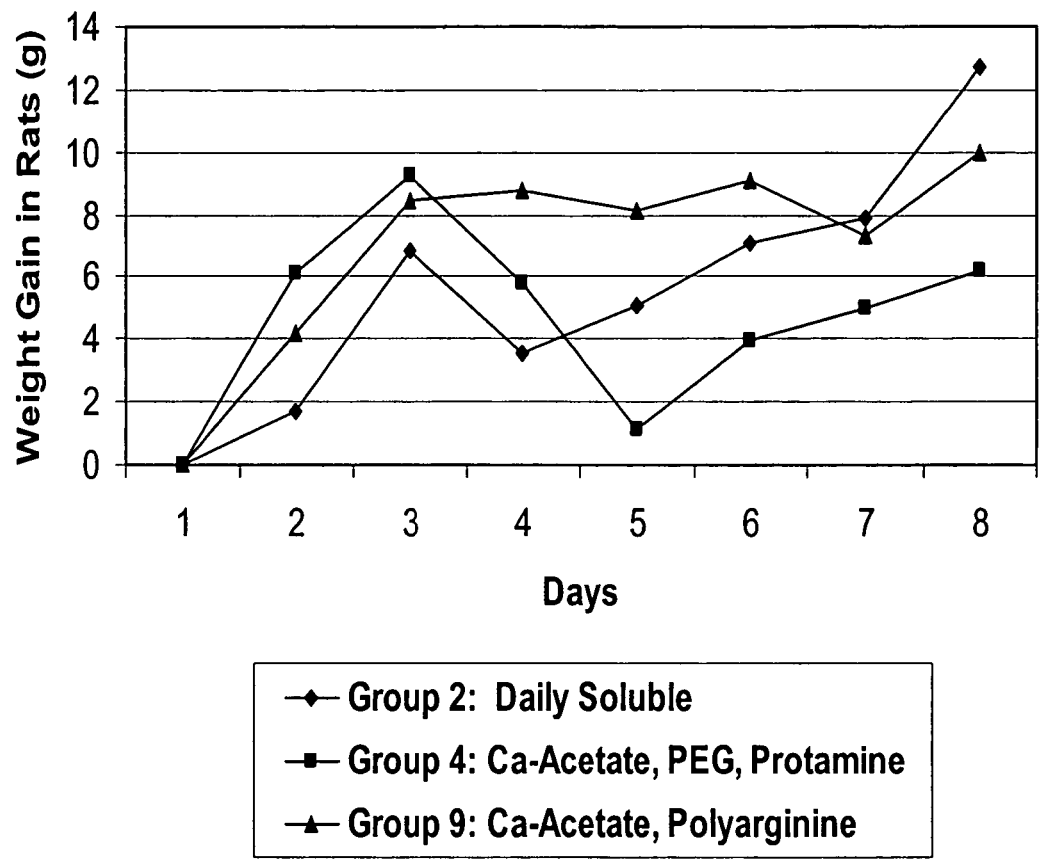
FIG. 19B shows weight gain (g) of female Sprague-Dawley rats of selected formulations (Groups 2, 4 and 9) over 8 days after either daily subcutaneous administration over 7 days (Group 2) or a single subcutaneous administration on day 1 of 7 days (Groups 4 and 9) of 6.7 mg/kg dose of hGH per rat. See Example 22 and Table 13.

Table 14 and FIG. 19B illustrate the seven-day effect of administering a single dose (Day 1) of crystals according to this invention as compared with that of administering a daily dose of commercially-available hGH. For example, FIG. 19B demonstrates that calcium crystals of hGH complexed with polyarginine achieves a weight gain comparable to that of the daily soluble dose with only one dosage over the same time period. In comparing the weight gained and the respective release profiles of rhGH in serum, it is evident that the longer-releasing polyarginine formulation correlates with a more sustained velocity of weight gain.

Example 23

Comparative pharmacodynamic studies in female juvenile cynomologous monkeys. The goal of this study was to assess the in vivo pharmacokinetic profile of crystalline recombinant human growth hormone (rhGH) when administered subcutaneously to female cynomologous monkeys. These data were generated in order to establish a model for controlled release of crystalline rhGH in blood serum and for weight gain as a function of crystalline rhGH release.

TABLE 15

Study Design for Primate Studies I

| Group # | Sample | Administration of Dose[c] (hour) | Dose Level (mg/kg) | Dose Concentration (mg/ml) | Dose Volume (ml/kg) | Number of Animals (Female) |
|---|---|---|---|---|---|---|
| 1 | Daily Soluble[a] | 0, 24, 48, 72, 96, 120, 144 | 0.8 | 3.2 | 0.25 | 4 |
| 2 | Na-Acetate, PEG, polyarginine[b] | 0 | 5.6 | 22.4 | 0.25 | 4 |
| 3 | Na-Acetate, PEG, protamine[b] | 0 | 5.6 | 22.4 | 0.25 | 4 |

[a]Commercially-available hGH (soluble, uncrystallized form) was obtained from Novartis and diafiltered in WFI. Group 1 (positive control) received soluble hGH on each of the administration days.
[b]See Examples 18 and 19 for preparation.
[c]All doses were delivered after daily bleed.

Twelve female juvenile cynomologous monkeys were divided into three groups, each having four animals per group, and were administered either soluble rhGH (Group 1), sodium crystals of rhGH with PEG and polyarginine (Group 2, according to Examples 18 and 19) or sodium crystals of rhGH with PEG and protamine (Group 3, according to Examples 18 and 19). The monkeys, ranging from 2-6 kg in weight and 4-7 years of age at the onset of treatment, were individually housed in stainless steel cages equipped with an automatic watering system or water bottles. The animal room environment was controlled (approximately 21±3° C., 30-70% humidity, 12 hours light and 12 hours darkness in each 24-hour period, and 12-20 air changes per hour) and twice daily, the monkeys were fed a standard certified commercial primate chow (Harlan Teklad Certified Primate Diet #2055C).

This primate study was conducted in order to measure and compare serum concentrations of hGH and IGF-1 after the administration of soluble rhGH (Group 1), sodium crystals of rhGH with PEG and polyarginine (Group 2) and sodium crystals of rhGH with PEG and protamine (Group 3). Body weights were recorded for all animals at transfer and prior to dosing on the times indicated in Table 15 above. Blood samples (approximately 1 ml) were collected from each animal via the femoral, brachial or saphenous vein on the mornings of days −216, −120, 0, 2, 4, 6, 8, 10, 24, 48, 72, 96, 120, 144, 168, 192, 216, 240, 264, 288 and 312. Blood was collected into serum separating tubes, left at room temperature for 30-45 minutes to allow clotting, and centrifuged at 2-8° C. for 10 minutes at 3000 rpm. Each serum sample was split into a 100 μl aliquot and remaining aliquot, both of which were stored at −70±10° C. prior to analysis. Typically, the smaller 100 μl aliquot was used for rhGH determination and the larger remainder was used for IGF-1 determination. There were some exceptions, due to volume of replicates needed.

Collected serum samples were then analyzed for hGH concentration (see Table 16). Appropriate dilutions were made to rhGH concentrations that fell outside the standard value range. All values were used to obtain an individual per animal-average background level of primate GH. This per animal average was subtracted from the serum levels measured at each time point for that test subject. The corrected values per time point were then averaged to obtain a corrected mean of rhGH in serum. Standard errors were then calculated by using standard deviation of the corrected mean and divided by the square root of N=4.

TABLE 16 rhGH levels for groups 1 (daily soluble), 2 (sodium rhGH/polyarginine) and 3 (sodium rhGH/protamine)

| Time in hrs | Group 1 - Average daily soluble rhGH (ng/ml) | Std. Err. | Group 2 - Average sodium rhGH/polyarginine, (ng/ml) | Std. Err. | Group 3 - Average sodium rhGH/protamine, (ng/ml) | Std. Err. |
|---|---|---|---|---|---|---|
| −216 | 4 | 7 | −4 | 7 | −2 | 1 |
| −120 | 8 | 9 | 7 | 5 | 7 | 9 |
| 0 | 343 | 65 | −4 | 3 | −5 | 9 |
| 2 | 372 | 48 | −6 | 6 | 1 | 13 |
| 4 | 262 | 37 | 11 | 9 | 20 | 12 |
| 6 | 205 | 45 | 85 | 45 | 94 | 35 |
| 8 | 132 | 29 | 186 | 93 | 159 | 57 |
| 10 | 18 | 37 | 409 | 202 | 381 | 189 |
| 24 | −14 | 7 | 404 | 17 | 333 | 37 |
| 48 | −7 | 8 | 178 | 33 | 216 | 43 |
| 72 | −3 | 10 | 77 | 35 | 86 | 18 |
| 96 | −9 | 9 | 12 | 14 | 21 | 13 |
| 120 | −11 | 6 | 6 | 13 | 2 | 11 |
| 144 | −3 | 13 | −6 | 10 | 3 | 13 |
| 168 | 10 | 11 | −2 | 4 | −1 | 11 |
| 192 | −11 | 10 | 3 | 2 | 0 | 7 |
| 216 | −13 | 9 | 18 | 12 | 9 | 6 |
| 240 | 1 | 5 | 18 | 14 | 31 | 12 |
| 264 | 8 | 3 | 20 | 5 | 17 | 11 |

TABLE 16-continued rhGH levels for groups 1 (daily soluble), 2 (sodium rhGH/polyarginine) and 3 (sodium rhGH/protamine)

| Time in hrs | Group 1 - Average daily soluble rhGH (ng/ml) | Std. Err. | Group 2 - Average sodium rhGH/polyarginine, (ng/ml) | Std. Err. | Group 3 - Average sodium rhGH/protamine, (ng/ml) | Std. Err. |
|---|---|---|---|---|---|---|
| 288 | −15 | 8 | 1 | 4 | 17 | 11 |
| 312 | 4 | 7 | 1 | 5 | 8 | 17 |

Note:
rhGH value is the average value from 4 animals that has been baseline adjusted, i.e., value minus baseline. Baseline is the average of values at t = −216, −120 and 0 hours.

Figure 20A:
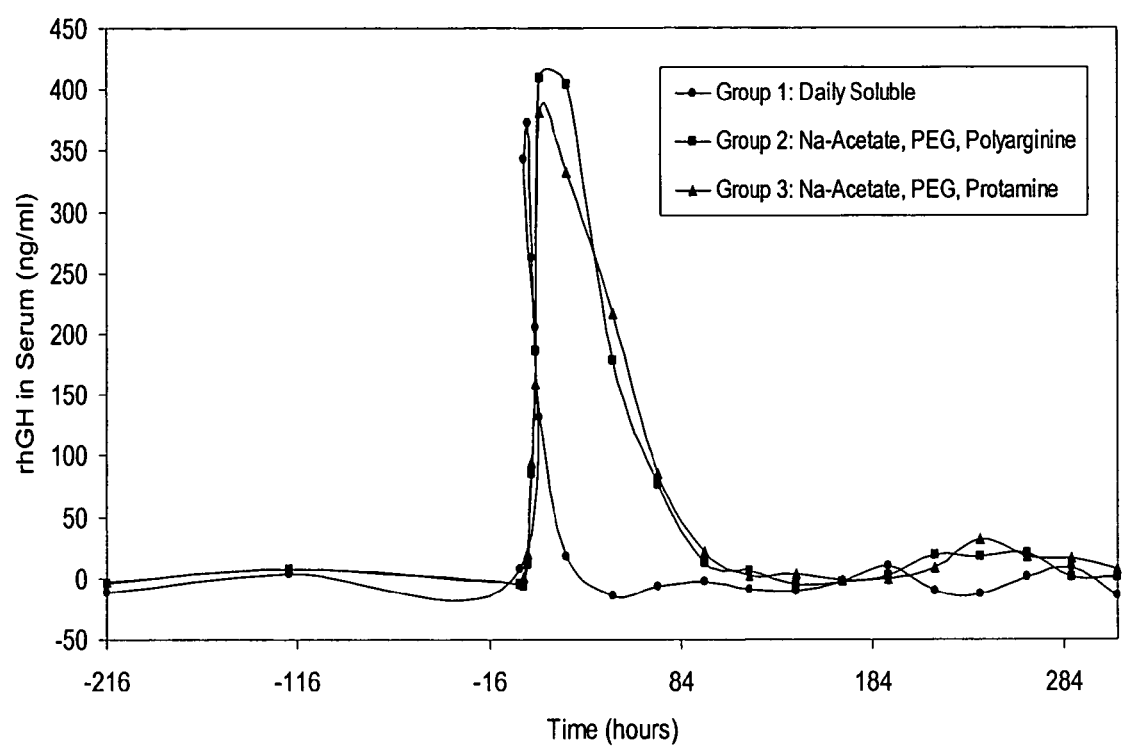
FIG. 20A shows the concentration of hGH in blood serum as a function of time for female juvenile cynomologous monkeys subcutaneously administered daily soluble hGH (Group 1), sodium crystals of hGH complexed with polyarginine (Group 2) and sodium crystals of hGH complexed with protamine (Group 3) according to Table 16. See Example 23.

FIG. 20A illustrates the level of rhGH in serum, after baseline adjustment, as a function of time in hours for Groups 1, 2 and 3.

TABLE 17

Summary of pharmacokinetic parameters based on data in Table 16

|  | Group 1[a] | Group 2 | Group 3 |
|---|---|---|---|
| Dose Amount (mg) | 3.2 | 22.4 | 22.4 |
| Dosage (mg/kg) | 0.8 | 5.6 | 5.6 |
| $C_{max}$ (ng/ml) | 372 | 409 | 381 |
| $T_{max}$ (hr) | 2 | 10 | 10 |
| AUC (0-t) (ng · hr · kg/ml · mg) | 4570 | 3503 | 3455 |
| $T_{90\%}$ (hr) | 20 | 74 | 77 |

[a]Commercially-available hGH (soluble, uncrystallized form) was diafiltered in WFI. Group 1 (positive control) received soluble hGH on each of the 7 administration days.

The data above demonstrates that the time at which maximum hGH appeared in the serum ($T_{max}$) was 10 hours for the polyarginine complexed sodium crystal hGH, 10 hours for the protamine complexed sodium crystal hGH and 2 hours for the soluble hGH. Even though the soluble hGH was delivered at 1/7th the dose of the crystal administrations, the $C_{max}$ values listed above in Table 17 show that hGH when delivered in either of the complexed crystalline forms significantly reduce the initial serum concentration spike. In addition, a $T_{90\%}$ value has been calculated for the soluble and crystalline groups. The $T_{90\%}$ for Group 1, the soluble form, was 20 hours, whereas the $T_{90\%}$ for Groups 2 and 3, the complexed crystalline forms, were 74 and 77 hours, respectively. These results clearly show that the complexed crystalline forms result in elevated hGH levels for significantly longer times than that of the soluble form.

Figure 20B:
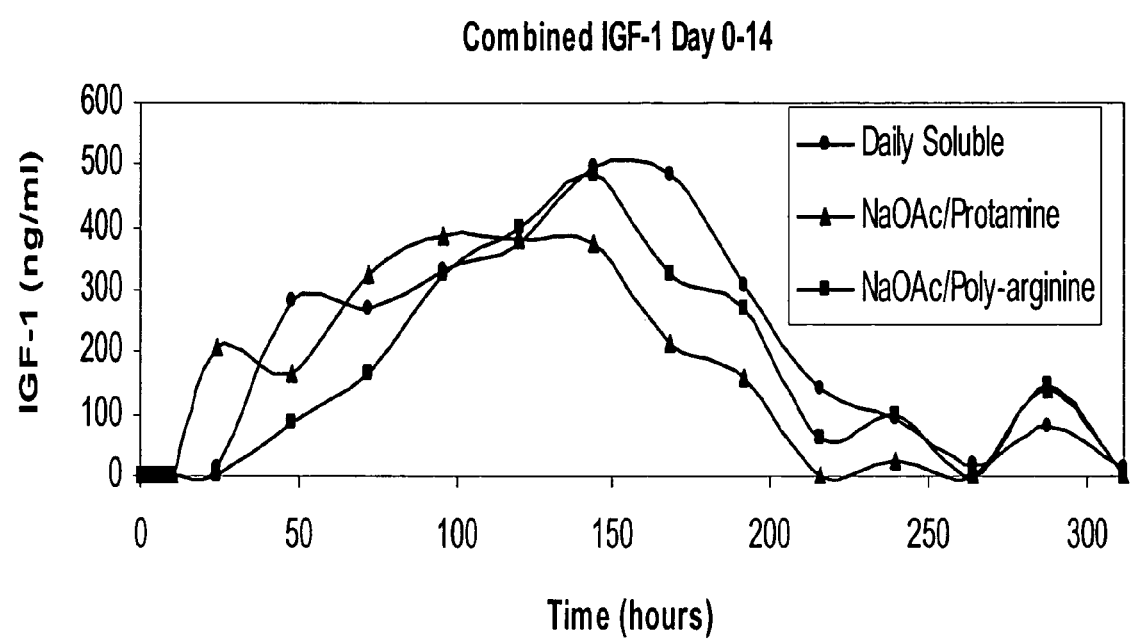
FIG. 20B shows the concentration of IGF-1 in blood serum as a function of time for female juvenile cynomologous monkeys subcutaneously administered daily soluble hGH (Group 1), sodium crystals of hGH complexed with polyarginine (Group 2) and sodium crystals of hGH complexed with protamine (Group 3) according to Table 18. See Example 23.

In addition to determination of serum concentrations of hGH, the level of IGF-1 was also measured as a function of time. By measuring the production of IGF-1, the efficacy of rhGH was ascertained. Table 18 below reports the IGF-1 concentrations for animals in Groups 1-3. FIG. 20B illustrates that following baseline subtraction of endogenous IGF-1 levels, complexed crystalline formulations have demonstrated the ability to stimulate IGF-1 release comparable to daily soluble administrations. These results, in non-human primates, indicate that formulations according to this invention may be advantageously used to achieve similar efficacy in humans.

TABLE 18.

IGF-1 levels for Group, Daily soluble, sodium rhGH/polyarginine and Sodium rhGH/protamine

| Time in hrs | Group 1 - Average daily soluble IGF-1 (ng/ml) | Std. Err. | Group 2 - Average sodium rhGH/polyarginine, IGF-1 (ng/ml) | Std. Err. | Group 3 - Average sodium rhGH/protamine, IGF-1 (ng/ml) | Std. Err. |
|---|---|---|---|---|---|---|
| −216 | −48 | 54 | 263 | 148 | 31 | 94 |
| −120 | −0.63 | 22 | 4 | 34 | 218 | 115 |
| 0 | 48 | 73 | −268 | 158 | −249 | 86 |
| 2 | 39 | 32 | −160 | 146 | −56 | 104 |
| 4 | 22 | 52 | −344 | 191 | −120 | 114 |
| 6 | 37 | 45 | −244 | 189 | −19 | 96 |
| 8 | −22 | 9 | −464 | 170 | −66 | 119 |
| 10 | 106 | 63 | −491 | 219 | 4 | 86 |
| 24 | 130 | 130 | −106 | 278 | 223 | 214 |
| 48 | 446 | 59 | 164 | 244 | 191 | 164 |
| 72 | 414 | 95 | 248 | 224 | 340 | 207 |
| 96 | 485 | 114 | 402 | 67 | 416 | 243 |
| 120 | 524 | 73 | 484 | 126 | 392 | 216 |
| 144 | 636 | 63 | 574 | 189 | 397 | 187 |
| 168 | 636 | 82 | 415 | 191 | 240 | 176 |
| 192 | 438 | 71 | 356 | 136 | 227 | 153 |
| 216 | 288 | 87 | 155 | 108 | 117 | 146 |
| 240 | 210 | 69 | 197 | 57 | 93 | 144 |
| 264 | 161 | 67 | 88 | 82 | 85 | 167 |
| 288 | 222 | 113 | 243 | 95 | 201 | 208 |
| 312 | 178 | 175 | 79 | 120 | 86 | 149 |

Note:
IGF-1 values are reported as the average values calculated from 4 animals that have been baseline adjusted, i.e., value minus baseline. Baseline is the average of values at t = −216, −120 and 0 hours.

Example 24

Comparative pharmacodynamic studies in female juvenile cynomologous monkeys with different protamine ratios. The goal of this study was to assess the in vivo pharmacokinetic profile of crystalline recombinant human growth hormone (rhGH) when administered subcutaneously to female cynomologous monkeys. These data were generated in order to study the effect that the ratio of sodium hGH to protamine has on the controlled release of crystalline rhGH in blood serum and for weight gain as a function of crystalline rhGH release.

This primate study was conducted in order to measure and compare serum concentrations of hGH and IGF-1 after administration of soluble rhGH (Group 1), sodium crystals of rhGH with PEG and protamine (3:1 rhGH:protamine) (Group 2) and sodium crystals of rhGH with PEG and protamine (2:1 rhGH:protamine) (Group 3). Body weights were recorded for all animals at transfer and prior to dosing on the times indicated in Table 19 above. Blood samples (approximately 1 ml) were collected from each animal via the femoral, brachial or saphenous vein on the mornings of days −144, −120, −96, −72, −48, −24, 0, 2, 4, 6, 8, 10, 24, 48, 72, 96, 120, 144, 168,

TABLE 19

Experimental Study for Primate Studies II

| Group # | Sample | Administration of Dose[c] (hour) | Dose Level (mg/kg) | Dose Concentration (mg/ml) | Dose Volume (ml/kg) | Number of Animals (Female) |
|---|---|---|---|---|---|---|
| 1 | Daily Soluble[a] | 0, 24, 48, 72, 96, 120, 144 | 0.8 | 3.2 | 0.25 | 4 |
| 2 | Na-Acetate, PEG, protamine (3:1)[b] | 0 | 5.6 | 22.4 | 0.25 | 4 |
| 3 | Na-Acetate, PEG, protamine (2:1)[b] | 0 | 5.6 | 22.4 | 0.25 | 4 |

[a]Commercially-available hGH (soluble, uncrystallized form) was obtained from Novartis and diafiltered in WFI. Group 1 (positive control) received soluble hGH on each of the administration days.
[b]See Examples 18 and 19 for preparation.
[c]All doses were delivered after daily bleed.

In Primate Study II, the twelve female juvenile cynomologous monkeys described in Primate Study I were divided into three groups, each having four animals per group, and were administered either soluble rhGH (Group 1), sodium crystals of rhGH with PEG and protamine (3:1 rhGH:protamine) (Group 2) (Examples 18 and 19) or sodium crystals of rhGH with PEG and protamine (2:1 rhGH:protamine) (Group 3) (Examples 18 and 19). The monkeys, ranging from 2-6 kg in weight and 4-7 years of age at the onset of treatment, were individually housed in stainless steel cages equipped with an automatic watering system or water bottles. The animal room environment was controlled (approximately 21±30° C., 30-70% humidity, 12 hours light and 12 hours darkness in each 24-hour period, and 12-20 air changes per hour) and twice daily, the monkeys were fed a standard certified commercial primate chow (Harlan Teklad Certified Primate Diet #2055C).

192, 216, 240, 264, 288, and 312. Blood was collected into serum separating tubes, left at room temperature for 30-45 minutes to allow clotting, and centrifuged at 2-8° C. for 10 minutes at 3000 rpm. Each serum sample was split into a 100 µl aliquot and a remaining aliquot, both of which were stored at −70±10° C. prior testing.

Concentrations of hGH (ng/ml) in the collected serum samples were analyzed and baseline corrected (see data in Table 20). Note that appropriate dilutions were made to rhGH concentrations that fell outside the standard value range. All values were then used to obtain an individual per animal average background level of primate hGH. This per animal average was subtracted from the serum levels measured at each time point for that test subject. The corrected values per time point were then averaged to obtain a corrected mean of rhGH in serum. Standard errors were then calculated by using standard deviation of the corrected mean and divided by the square root of N=4.

TABLE 20 rhGH levels for Groups 1 (daily soluble), 2 (sodium rhGH/protamine (3:1)) and 3 (sodium rhGH/protamine (2:1))

| Time in hrs | Group 1 - Average daily soluble rhGH (ng/ml) | Std. Err. | Group 2 - Average sodium rhGH/protamine (3:1), (ng/ml) | Std. Err. | Group 3 - Average sodium rhGH/protamine, (2:1) (ng/ml) | Std. Err. |
|---|---|---|---|---|---|---|
| −144 | −14 | 6 | −13 | 6 | 34 | 22 |
| −120 | −14 | 5 | −9 | 5 | 10 | 6 |
| −96 | 18 | 12 | 48 | 23 | 28 | 43 |
| −72 | −1 | 5 | −5 | 6 | 3 | 9 |
| −48 | −9 | 5 | −2 | 5 | 14 | 6 |
| −24 | −2 | 9 | −14 | 7 | −3 | 10 |
| 0 | 21 | 9 | −4 | 9 | 1 | 5 |
| 2 | 312 | 47 | 8 | 10 | −29 | 16 |
| 4 | 401 | 57 | 77 | 32 | 13 | 8 |
| 6 | 186 | 16 | 172 | 62 | 89 | 52 |

TABLE 20-continued rhGH levels for Groups 1 (daily soluble), 2 (sodium rhGH/protamine (3:1)) and 3 (sodium rhGH/protamine (2:1))

| Time in hrs | Group 1 - Average daily soluble rhGH (ng/ml) | Std. Err. | Group 2 - Average sodium rhGH/protamine (3:1), (ng/ml) | Std. Err. | Group 3 - Average sodium rhGH/protamine, (2:1) (ng/ml) | Std. Err. |
|---|---|---|---|---|---|---|
| 8   | 157   | 29 | 330 | 104 | 222  | 108 |
| 10  | 172   | 24 | 456 | 109 | 364  | 142 |
| 24  | 3     | 4  | 316 | 29  | 372  | 74  |
| 48  | 8     | 7  | 153 | 47  | 128  | 15  |
| 72  | 6     | 6  | 116 | 81  | 30   | 23  |
| 96  | −2    | 5  | 42  | 15  | 13   | 21  |
| 120 | 14    | 3  | 22  | 22  | 22   | 14  |
| 144 | 16    | 16 | 8   | 12  | −13  | 11  |
| 168 | 14    | 8  | 7   | 6   | −21  | 13  |
| 192 | 2     | 7  | −4  | 7   | 3    | 22  |
| 216 | 11    | 9  | 6   | 14  | −29  | 19  |
| 240 | 27    | 19 | 14  | 9   | −4   | 8   |
| 264 | −1    | 6  | 35  | 21  | −19  | 18  |
| 288 | −2    | 9  | 2   | 5   | −32  | 18  |
| 312 | −0.58 | 9  | 10  | 6   | −21  | 18  |

Note:
rhGH values are reported as the average values from 4 animals that have been baseline adjusted, i.e., value minus baseline. Baseline is the average of values at t = −144, −120, −96, −72, −48, −24 and 0 hours.

Figure 21A:
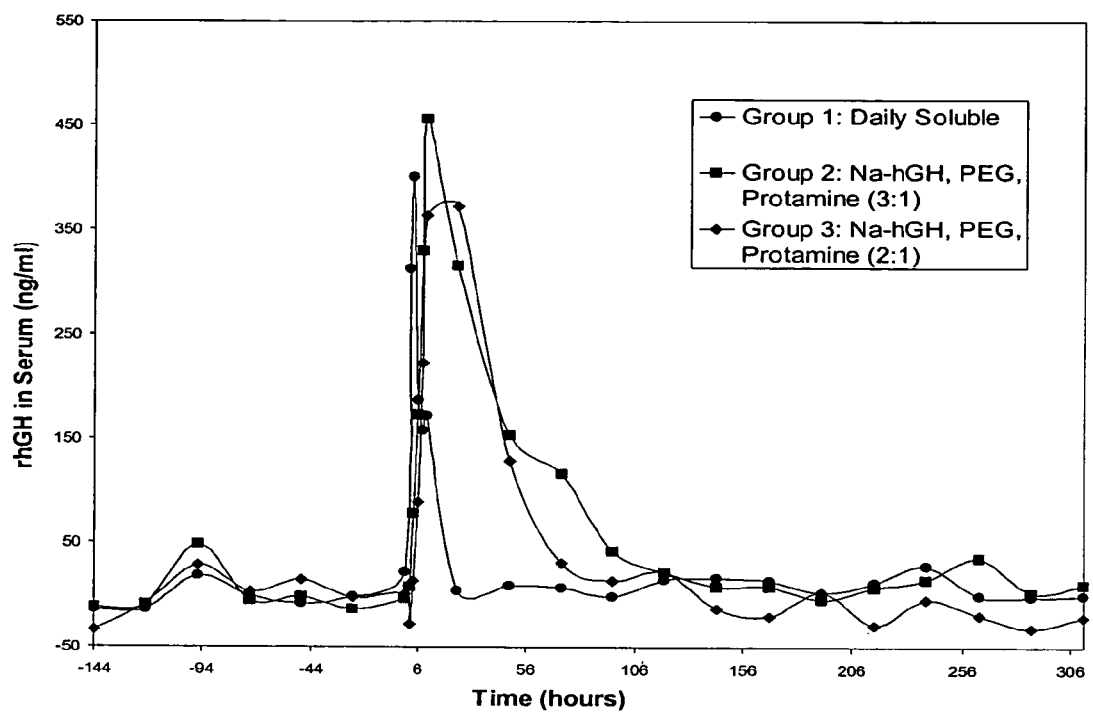
FIG. 21A shows the concentration of hGH in blood serum as a function of time for female juvenile cynomologous monkeys subcutaneously administered daily soluble hGH (Group 1), sodium crystals of hGH complexed with protamine (3:1 ratio of hGH:protamine) (Group 2) and sodium crystals of hGH complexed with protamine (2:1 ratio of hGH:protamine) (Group 3) according to Table 20. See Example 24.

FIG. 21A illustrates the level of rhGH in serum, after baseline adjustment, as a function of time in hours for Groups 1, 2 and 3.

TABLE 21

Summary of pharmacokinetic parameters based on data in Table 20

|  | Group 1[a] | Group 2 | Group 3 |
|---|---|---|---|
| Dose Amount (mg) | 3.2 | 22.4 | 22.4 |
| Dosage (mg/kg) | 0.8 | 5.6 | 5.6 |
| $C_{max}$ (ng/ml) | 401 | 456 | 380 |
| $T_{max}$ (hr) | 4 | 10 | 24 |
| AUC (0-t) (ng · hr · kg/ml · mg) | 4432 | 3669 | 2893 |
| $T_{90\%}$ (hr) | 20 | 119 | 72 |

[a] Commercially-available hGH (soluble, uncrystallized form) diafiltered in WFI. Group 1 (positive control) received soluble hGH on each of the 7 administration days.

These data demonstrate that the time at which maximum hGH appeared in the serum was 10 hours for the protamine (3:1) complexed crystal hGH, 24 hours for the protamine (2:1) complexed crystal hGH and 4 hours for the soluble hGH. Given that soluble hGH was delivered at 1/7th the dose of the crystal administrations, the $C_{max}$ values listed above in Table 22 show that hGH, when delivered in either complexed crystalline form significantly reduced the maximum serum concentration. The $T_{90\%}$ for Group 1, the soluble form, was 20 hours, whereas the $T_{90\%}$ for Groups 2 and 3, the complexed crystalline form, were 119 and 72, respectively. These results clearly indicate that the complexed crystalline forms result in elevated hGH levels for significantly longer than the soluble form.

Figure 21B:
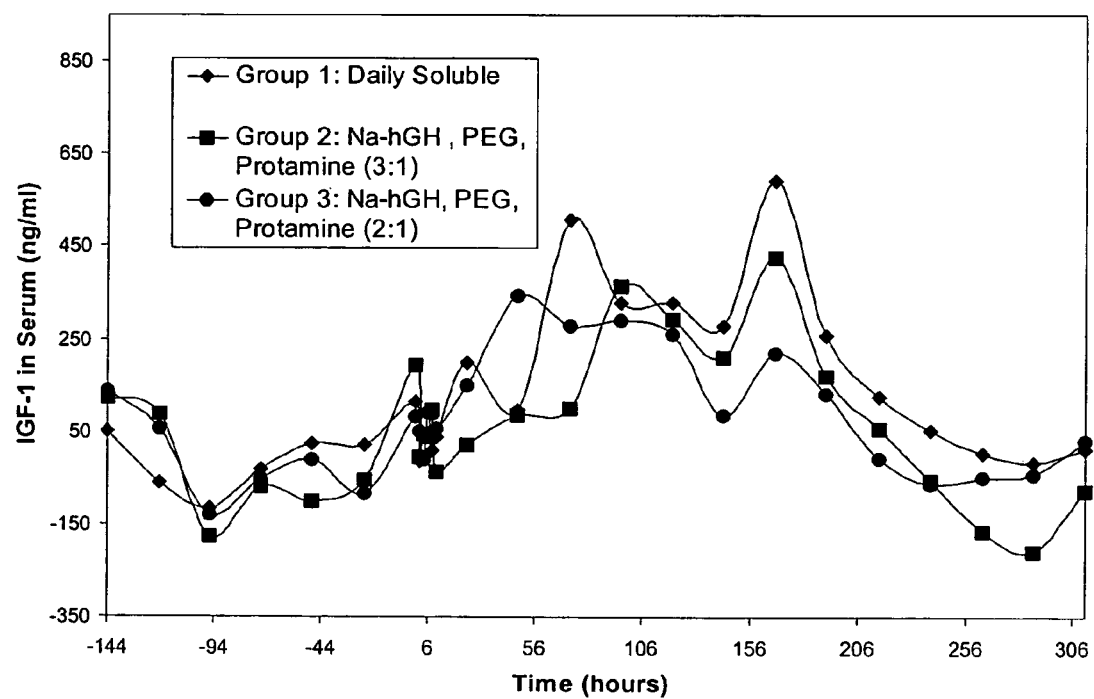
FIG. 21B shows the concentration of IGF-1 in blood serum as a function of time for female juvenile cynomologous monkeys subcutaneously administered daily soluble hGH (Group 1), sodium crystals of hGH complexed with protamine (3:1 ratio of hGH:protamine) (Group 2) and sodium crystals of hGH complexed with protamine (2:1 ratio of hGH:protamine) (Group 3) according to Table 22. See Example 24.

In addition to determination of serum concentrations of hGH, the level of IGF-1 was also measured as a function of time. By measuring the production of IGF-1, the efficacy of rhGH was ascertained. Table 22 below reports the IGF-1 concentrations for animals in Groups 1-3. FIG. 21B illustrates that following baseline subtraction of endogenous IGF-1 level, complexed crystalline formulations are capable of stimulating IGF-1 release comparable to daily soluble administrations. These non-human primate results indicate that formulations according to this invention may be advantageously used to elicit similar efficacy in humans.

TABLE 22

IGF-1 levels for groups 1 (daily soluble), 2 (sodium rhGH/protamine (3:1)) and 3 (sodium rhGH/protamine (2:1))

| Time in hrs | Group 1 - Average daily soluble, IGF-1 (ng/ml) | Std. Err. | Group 2 - Average sodium rhGH/protamine (3:1), IGF-1 (ng/ml) | Std. Err. | Group 3 - Average sodium rhGH/protamine (2:1), IGF-1 (ng/ml) | Std. Err. |
|---|---|---|---|---|---|---|
| −144 | 49   | 92  | 123  | 60  | 137  | 134 |
| −120 | −61  | 19  | 88   | 42  | 57   | 98  |
| −96  | −116 | 27  | −178 | 11  | −130 | 13  |
| −72  | −33  | 59  | −69  | 40  | −52  | 43  |
| −48  | 24   | 47  | −102 | 100 | −10  | 64  |
| −24  | 22   | 46  | −56  | 85  | −83  | 78  |
| 0    | 115  | 71  | 194  | 106 | 82   | 107 |
| 2    | −15  | 71  | −6   | 79  | 51   | 95  |
| 4    | −6   | 96  | 45   | 42  | −10  | 94  |
| 6    | 48   | 106 | 38   | 63  | 91   | 74  |
| 8    | 10   | 119 | 97   | 47  | 88   | 78  |
| 10   | 38   | 106 | −37  | 56  | 57   | 75  |
| 24   | 200  | 160 | 20   | 48  | 150  | 107 |

TABLE 22-continued

IGF-1 levels for groups 1 (daily soluble), 2 (sodium rhGH/protamine (3:1)) and 3 (sodium rhGH/protamine (2:1))

| Time in hrs | Group 1 - Average daily soluble, IGF-1 (ng/ml) | Std. Err. | Group 2 - Average sodium rhGH/protamine (3:1), IGF-1 (ng/ml) | Std. Err. | Group 3 - Average sodium rhGH/protamine (2:1), IGF-1 (ng/ml) | Std. Err. |
|---|---|---|---|---|---|---|
| 48  | 99   | 90  | 85   | 68  | 342 | 97  |
| 72  | 505  | 391 | 100  | 155 | 278 | 105 |
| 96  | 328  | 202 | 363  | 161 | 289 | 122 |
| 120 | 329  | 224 | 294  | 89  | 261 | 136 |
| 144 | 279  | 282 | 210  | 81  | 86  | 103 |
| 168 | 591  | 266 | 424  | 184 | 219 | 104 |
| 192 | 259  | 185 | 169  | 163 | 131 | 50  |
| 216 | 127  | 152 | 55   | 107 | −8  | 67  |
| 240 | 54   | 153 | −54  | 141 | −64 | 72  |
| 264 | 4    | 132 | −165 | 103 | −50 | 49  |
| 288 | −16  | 105 | −208 | 122 | −43 | 75  |
| 312 | 11   | 100 | −77  | 207 | 30  | 77  |

Note:
IGF-1 values are reported as the average values from 4 animals that have been baseline adjusted, i.e., value minus baseline. Baseline is the average of values at t = −144, −120, −96, −72, −48, −24 and 0 hours.

Example 25

Pharmcocodynamic study of human growth hormone administered by single or daily subcutaneous injection to hypophysectomized male rats. The goal of this study was to compare the efficacy of different formulations of hGH when administered once or daily for seven consecutive days subcutaneously to hypophysectomized male Wistar rats. The study design was as follows:

TABLE 23

Study Design - Sample Description

| Group # or Test Compound | Sample[a] | Sample Description |
|---|---|---|
| 1 | Daily Soluble Vehicle - Sham Hypophysectomy | (no hGH) 16.7 mg/ml D-mannitol, 26.7 mg/ml sucrose, 50 mM $NaH_2PO_4$ (pH 6.5) |
| 2 | Daily Soluble Vehicle - Low Dose | (no hGH) 16.7 mg/ml D-mannitol, 26.7 mg/ml sucrose, 50 mM $NaH_2PO_4$ (pH 6.5) |
| 3 | Daily Soluble Vehicle - High Dose | (no hGH) 16.7 mg/ml D-mannitol, 26.7 mg/ml sucrose, 50 mM $NaH_2PO_4$ (pH 6.5) |
| 4 | Daily Soluble - Low Dose | 0.71 mg/ml rhGH, 16.7 mg/ml D-mannitol, 26.7 mg/ml sucrose, 50 mM $NaH_2PO_4$ (pH 6.5) |
| 5 | Daily Soluble - High Dose | 1.0 mg/ml rhGH, 16.7 mg/ml D-mannitol, 26.7 mg/ml sucrose, 50 mM $NaH_2PO_4$ (pH 6.5) |
| 6 | Soluble Single Bolus High Dose | 3.5 mg/ml rhGH, 16.7 mg/ml D-mannitol, 26.7 mg/ml sucrose, 50 mM $NaH_2PO_4$ (pH 6.5) |
| 7 | Polyarginine Crystals - High Dose | 18.7 mg/ml crystalline rHGH, 250 mM NaOAc, 6% PEG-6000, 25 mM Tris-HCl (pH 8.6), 3.6 mg/ml polyarginine HCl (molar ratio of rhGH:polyarginine is 1:0.587 |
| 8 | Vehicle Control- Protamine Crystals | 250 mM NaOAc, 6% PEG-6000, 25 mM Tris-HCl (pH 8.6), 0.75 mg/ml protamine sulfate |
| 9 | Protamine Crystals - Low Dose | 3.3 mg/ml crystalline rHGH, 250 mM NaOAc, 6% PEG-6000, 25 mM Tris-HCl (pH 8.6), 0.75 mg/ml protamine sulfate (molar ratio of rhGH:polyarginine is 1:1.715 |
| 10 | Protamine Crystals - High Dose | 18.7 mg/ml crystalline rHGH, 250 mM NaOAc, 6% PEG-6000, 25 mM Tris-HCl (pH 8.6), 4 mg/ml protamine sulfate (molar ratio of rhGH:polyarginine is 1:1.715. |
| 11 | Vehicle Control- Polyarginine Crystals | 250 mM NaOAc, 6% PEG-6000, 25 mM Tris-HCl (pH 8.6), 3.6 mg/ml polyarginine-HCl |
| 12 | Vehicle Control- Single Bolus | 16.7 mg/ml D-mannitol, 26.7 mg/ml sucrose, 50 mM $NaH_2PO_4$ (pH 6.5) |

[a]All samples were prepared using WFI under sterile conditions. The vehicle and soluble hGH samples were filtered with 0.22 μm filter after bringing the solutions to their respective final volumes.

TABLE 24

Study Design - Administration

| Group # or Test Compound | Dose Level (mg/kg) | Dose Conc. (mg/ml) | Dose Volume (µl) | Dose Regimen | Number of Animals (males) |
|---|---|---|---|---|---|
| 1 | 0 | 0 | 200 | 7 daily doses | 13 |
| 2 | 0 | 0 | 20 | 7 daily doses | 11 |
| 3 | 0 | 0 | 80 | 7 daily doses | 11 |
| 4 | 0.143 | 0.71 | 20 | 7 daily doses | 11 |
| 5 | 0.8 | 1 | 80 | 7 daily doses | 12 |
| 6 | 5.6 | 3.5 | 160 | Day 1 | 11 |
| 7 | 5.6 | 18.7 | 30 | Day 1 | 12 |
| 8 | 0 | 0 | 30 | Day 1 | 11 |
| 9 | 1 | 3.3 | 30 | Day 1 | 12 |
| 10 | 5.6 | 18.7 | 30 | Day 1 | 12 |
| 11 | 0 | 0 | 30 | Day 1 | 11 |
| 12 | 0 | 0 | 30 | Day 1 | 11 |

Upon arrival, 138 male Wistar rats, weighing approximately 90-100 grams and being approximately 25-30 days old, were group-housed under controlled conditions (approximate temperature 23±3° C., relative humidity 30-70%, 12 hours light and 12 hours darkness in each 24-hour period, 10-15 air changes per hour) and given access to purified water and laboratory chow ad libitum throughout the study. The rats were allowed to acclimate to the environment for two weeks prior to testing.

The 138 rats were administered samples according to the concentration, volume and dosing regimen in Table 24. The test compounds were administered once or once daily for seven consecutive days as a single bolus injection subcutaneously in the dorsum area. The site of injection was shaved and marked up to 3 days prior to dosing and thereafter as required to facilitate injection. The test compounds were administered using a 30-gauge×8 mm needle attached to a 300 µl syringe. Test compounds were carefully inverted in order to ensure suspension or solution uniformity without causing foaming prior to withdrawal into the syringe and again prior to administration.

Figure 22:
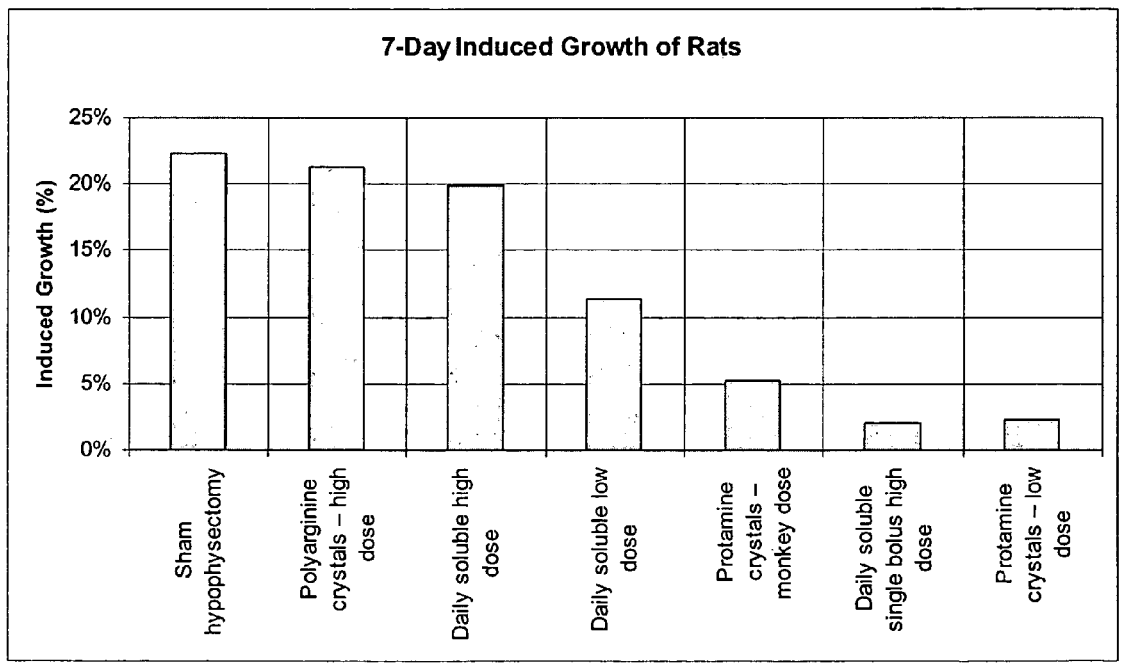
FIG. 22 illustrates the seven-day growth of male Wistar rats that had been subcutaneously administered control (Group 1, once daily over seven days), soluble hGH (Groups 4 and 5, once daily over seven days) and crystalline hGH (Groups 6, 7, 9 and 10, once over seven days) according to Table 25. See Example 25.
Figure 23:
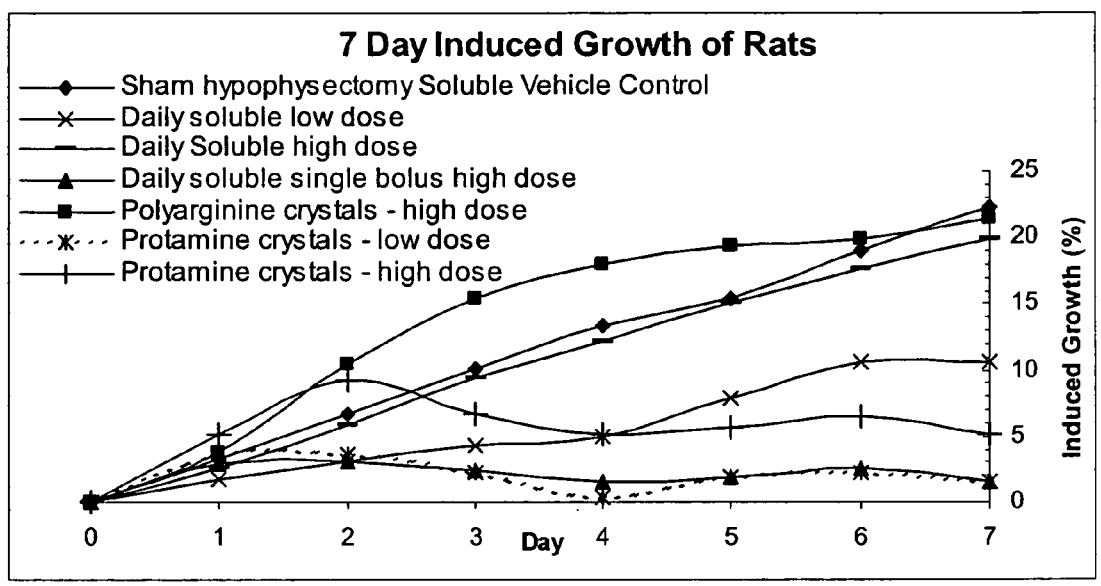
FIG. 23 illustrates the daily induced weight gain (grams) over a seven day period for male Wistar rats that had been subcutaneously administered control (Group 1, once daily over seven days), soluble hGH (Groups 4 and 5, once daily over seven days) and crystalline hGH (Groups 6, 7, 9 and 10, once over seven days) according to Table 26. See Example 25.

Weight gain was measured and recorded twice weekly during weeks −3 and −2 and daily from days −7 through 14. Rat weights were approximately 100 g±10% at dosing. The results of percent induced growth are presented in FIGS. 22 and 23 and summarized in Tables 25 and 26. In Table 25 "high dose" represents 5.6 mg/kg/week. The data illustrates the comparison of the weight gain of rats having a single injection of rhGH:polyarginine (Group 7, Examples 18 and 19) or rhGH:protamine (Groups 9 and 10, Examples 18 and 19) crystals over a seven day period versus a daily injection of control (Group 1, no hGH) or soluble hGH samples (Groups 4 and 5) over the same seven day period. Group 1, Sham Hypophysectomy rats, shows the normal growth over a seven day period. Moreover, rats having been administered rhGH:polyarginine (Group 7) had a higher percent induced growth with one injection over seven days than those rats that were administered soluble hGH (Group 5) each day for seven days. These results illustrate that hGH crystals and formulations according to the present invention are as efficacious as daily soluble rhGH administered over one week.

TABLE 25

8 Day Induced Weight Gain in Hypophysectomized Rats

| Group # or Test Compound | Sample Description | Day 8 Induced Growth |
|---|---|---|
| 1 | Sham hypophysectomy | 22% |
| 7 | Polyarginine crystals - high dose | 21% |
| 5 | Daily Soluble high dose | 20% |
| 4 | Daily soluble low dose | 11% |
| 10 | Protamine crystals - high dose | 5% |
| 6 | Daily soluble single bolus high dose | 2% |
| 9 | Protamine crystals - low dose | 2% |

TABLE 26

Daily Induced Weight Gain (grams) in Hypophysectomized Rats

| Group | Day 0 | 1 | 2 | 3 | 4 | 5 | 6 | 7 |
|---|---|---|---|---|---|---|---|---|
| 1 | 0 | 3 | 7 | 10 | 13 | 15 | 19 | 22 |
| 7 | 0 | 4 | 10 | 15 | 18 | 19 | 20 | 21 |
| 4 | 0 | 2 | 3 | 4 | 5 | 8 | 11 | 11 |
| 5 | 0 | 3 | 6 | 10 | 12 | 15 | 18 | 20 |
| 10 | 0 | 5 | 9 | 7 | 5 | 6 | 6 | 5 |
| 6 | 0 | 3 | 3 | 2 | 2 | 2 | 3 | 2 |
| 9 | 0 | 4 | 4 | 2 | 0 | 2 | 2 | 2 |

Example 26

Crystallization of hGH with sodium acetate and protamine sulfate. Here, a frozen bulk feed solution of soluble recombinantly-produced hGH (rhGH) was obtained from two stocks—one derived from *E. coli* (Novartis) and the other from yeast (Lucky Gold). Separate analyses of rhGH derived from *E. coli* and yeast stock solutions resulted in rhGH having the same crystallization and solubility characteristics irrespective of its source. Approximately 3.3 ml (10-20 mg/ml) of thawed rhGH feed solution was purified using a 10DG-desalting column supplied by BioRad. Prior to sample loading, the column was conditioned by washing the column with 30 ml of Tris-HCl (10 mM, pH 8.0). The rhGH sample was then loaded and allowed to enter the column by gravity. After discarding the first three ml of eluant, another 5.0 ml of 10 mM Tris-HCl pH 8.0 was added. 4.5 ml of the desalted rhGH was eluted and collected. Concentration by centrifugation was then performed using a Millipore concentrator (MWCO 10,000) at 3500 rpm for 20-30 min. The concentration of hGH was in range of 30 mg/ml as measured by absorbance at 280 nm/0.813 (1 mg/ml hGH A280=0.813 absorbance units). Crystals were grown by adding deionized water, Tris-HCl (pH 8.6), PEG-4000, Protamine sulfate and Na-acetate to final concentrations of 100 mM, 6% (v/v), 2 mg/ml and 500 mM, respectively, in the total solution with a final protein concentration of 15 mg/ml. The solution was then mixed gently and incubated at 33° C. for 12-16 hours. Needle-like crystals were obtained ranging in length from approximately 2 to 25 µm. After centrifuging and pelleting the crystals the supernatant was extracted and, crystallization yield was measured as greater than 90%.

Example 27

Crystallization of hGH with sodium acetate and polyarginine HCl. Here, a frozen bulk feed solution of soluble recombinantly-produced hGH (rhGH) was obtained from two stocks—one derived from *E. coli* (Novartis) and the other from yeast (Lucky Gold). Separate analyses of rhGH derived from *E. coli* and yeast stock solutions resulted in rhGH having the same crystallization and solubility characteristics irrespective of its source. Approximately 3.3 ml (10-20 mg/ml) of thawed rhGH feed solution was purified using a 10DG-desalting column supplied by BioRad. Prior to sample loading, the column was conditioned by washing the column with 30 ml of Tris-HCl (10 mM, pH 8.0). The rhGH sample was then loaded and allowed to enter the column by gravity. After discarding the first three ml of eluant, another 5.0 ml of 10 mM Tris-HCl pH 8.0 was added. 4.5 ml of the desalted rhGH was eluted and collected. Concentration by centrifugation was then performed using a Millipore concentrator (MWCO 10,000) at 3500 rpm for 20-30 min. The concentration of hGH was in range of 30 mg/ml as measured by absorbance at 280 nm/0.813 (1 mg/ml hGH A280=0.813 absorbance units). Crystals were grown by adding deionized water, Tris-HCl (pH 8.6), PEG-4000, polyarginine HCl and Na-acetate to final concentrations of 100 mM, 2% (v/v), 2 mg/ml and 500 mM, respectively, in the total solution with a final protein concentration of 15 mg/ml. The solution was then mixed gently and incubated at 33° C. for 12-16 hours. Needle-like crystals were obtained ranging in length from approximately 2 to 25 μm. After centrifuging and pelleting the crystals the supernatant was extracted and, crystallization yield was measured as greater than 90%.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein, including the appended embodiments.

---

---

We claim:

1. A composition comprising a crystal of human growth hormone (hGH), and polyarginine wherein said crystal of hGH is crystallized from a solution free of polyarginine and is soaked in polyarginine, and wherein said crystal of hGH comprises at least one cation and hGH which is selected from the group consisting of:

(a) the 191 amino acid sequence of native hGH (SEQ ID NO:1); and (b) the 192 amino acid sequence of somatrem consisting of said 191 amino acid sequence of native hGH (SEQ ID NO:1) and an additional N-terminal methionine, and wherein said hGH is present in a hGH:polyarginine ratio of 5:1 (w/w) to 40:1 (w/w).

2. The composition according to claim 1, wherein said cation is a calcium ion.

3. The composition according to claim 1, wherein said cation is a sodium ion.

4. A composition comprising a crystal of human growth hormone (hGH), and polyarginine wherein said crystal of hGH is crystallized from a solution free of polyarginine and is soaked in polyarginine, and wherein said crystal of hGH comprises at least one cation and hGH which is selected from the group consisting of:
(a) the 191 amino acid sequence of native hGH (SEQ ID NO:1); and
(b) the 192 amino acid sequence of somatrem consisting of said 191 amino acid sequence of native hGH (SEQ ID NO:1) and an additional N-terminal methionine; and
wherein said hGH is present in a hGH:polyarginine ratio of 5:1 (w/w) to 40:1 (w/w); and
wherein a single administration of said composition to a mammal provides an in vivo human growth hormone (hGH) serum concentration profile in said mammal having a $T_{90\%}$ value higher than that provided by a single administration of the same amount of soluble human growth hormone, and wherein $T_{90\%}$ is the time required to reach 90% of the total desired solubilized hGH level in a serum in vivo from the single administration hGH crystal has been achieved and wherein said higher $T_{90\%}$ represents slower in vivo dissolution rate.

5. The composition according to claim 4, wherein said cation is a calcium ion.

6. The composition according to claim 4, wherein said cation is a sodium ion.

7. A composition comprising a crystal of human growth hormone (hGH), and polyarginine wherein said crystal of hGH is crystallized from a solution free of polyarginine, and is soaked in polyarginine, and wherein said crystal of hGH comprises at least one cation and hGH which is selected from the group consisting of:
(a) the 191 amino acid sequence of native hGH (SEQ ID NO:1); and
(b) the 192 amino acid sequence of somatrem consisting of said 191 amino acid sequence of native hGH (SEQ ID NO:1) and an additional N-terminal methionine;
wherein a single administration of said composition to a mammal provides an in vivo insulin-like growth factor-I (IGF-1) serum elevation over baseline IGF-1 level in said mammal at similar levels compared to those provided by the same amount of soluble human growth hormone (hGH) administered in more than one administration; and
wherein said hGH is present in a hGH:polyarginine ratio of 5:1 (w/w) to 40:1 (w/w).

8. The composition according to claim 7, wherein said cation is a calcium ion.

9. The composition according to claim 7, wherein said cation is a sodium ion.

10. A composition comprising a crystal of human growth hormone (hGH), and polyarginine wherein said crystal of hGH is crystallized from a solution free of polyarginine, and is soaked in polyarginine, and wherein said crystal of hGH comprises at least one cation and hGH which is selected from the group consisting of
(a) the 191 amino acid sequence of native hGH (SEQ ID NO:1); and
(b) the 192 amino acid sequence of somatrem consisting of said 191 amino acid sequence of native hGH (SEQ ID NO:1) and an additional N-terminal methionine;
wherein a single administration of said composition has a bioavailability of at least 50% or more, as compared to that of an identical dose of soluble human growth hormone (hGH) delivered via the same administrative route, wherein said bioavailability is measured by area under curve (AUC) of total in vivo hGH serum concentration for said soluble hGH and said hGH crystal;
and wherein said hGH is present in a hGH:polyarginine ratio of 5:1 (w/w) to 40:1 (w/w).

11. The composition according to claim 4 or 7, wherein said mammal is a human.

12. The composition according to claim 1, 4, 7, or 10, further comprising an additional excipient.

13. The composition according to claim 12, wherein said additional excipient is selected from the group consisting of amino acid, a salt, an alcohol, a carbohydrate, a protein, a lipid, a surfactant, a polymer, a polyamino acid wherein said polyamino acid is not polyarginine, and mixtures thereof.

14. The composition according to claim 12, wherein said additional excipient is selected from the group consisting of protamine, polyvinylalcohol, cyclodextrin, dextran, calcium gluconate, polyamino acid wherein said polyamino acid is not polyarginine, polyethylene glycol, a dendrimer, polyorthinine, polyethyleneimine, chitosan and mixtures thereof.

15. The composition according to claim 14, wherein said additional excipient is selected from the group consisting of: protamine, polyethylene glycol and mixtures thereof.

16. The composition according to claim 12, wherein the concentration of human growth hormone (hGH) in said composition is between 0.1 and 100 mg/ml.

17. The composition according to claim 1, 4, 7 or 10, produced by:
(a) crystallizing the hGH with a cation, in a buffer with a pH between about 6 and 9, said buffer free of polyarginine; and then
(b) adding polyarginine to the crystal of hGH with a cation formed in step (a).

18. A pharmaceutical composition comprising the composition of claim 1.

19. A pharmaceutical composition comprising the composition of claim 2.

20. A pharmaceutical composition comprising the composition of claim 4.

21. A pharmaceutical composition comprising the composition of claim 17.

22. A pharmaceutical composition comprising the composition of claim 7.

23. A pharmaceutical composition comprising the composition of claim 10.

* * * * *